(12) United States Patent
Hongo et al.

(10) Patent No.: US 8,150,635 B2
(45) Date of Patent: Apr. 3, 2012

(54) METHOD AND AN APPARATUS FOR DETERMINING NUCLEOTIDE SEQUENCE, AND A COMPUTER PROGRAM PRODUCT TO BE EXECUTED BY THE APPARATUS

(75) Inventors: Sadato Hongo, Yokohama (JP); Shinji Yanaga, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/949,411

(22) Filed: Nov. 18, 2010

(65) Prior Publication Data

US 2011/0127171 A1 Jun. 2, 2011

Related U.S. Application Data

(63) Continuation of application No. 11/377,265, filed on Mar. 17, 2006, now abandoned.

(30) Foreign Application Priority Data

Mar. 18, 2005 (JP) .................. 2005-078977

(51) Int. Cl.
*G06F 19/00* (2006.01)
*G01N 33/48* (2006.01)
*G01N 31/00* (2006.01)
*C12Q 1/68* (2006.01)

(52) U.S. Cl. ................ 702/20; 702/19; 702/22; 435/6.1

(58) Field of Classification Search .................. None
See application file for complete search history.

(56) References Cited

U.S. PATENT DOCUMENTS

| 6,261,780 B1 | 7/2001 | Ogawa et al. |
| 6,399,305 B1 | 6/2002 | Makino et al. |
| 2003/0148332 A1 | 8/2003 | Taylor et al. |
| 2005/0158787 A1 | 7/2005 | Hongo et al. |

FOREIGN PATENT DOCUMENTS

| JP | 9-288080 | 11/1997 |
| JP | 2002-195997 | 7/2002 |
| JP | 2004-61426 | 2/2004 |
| JP | 2004-125777 | 4/2004 |

*Primary Examiner* — Russell S Negin

(74) *Attorney, Agent, or Firm* — Oblon, Spivak, McClelland, Maier & Neustadt, L.L.P.

(57) ABSTRACT

A method for determining nucleotide sequence encompasses: injecting a solution containing a sample DNA into a chip cartridge provided with a detecting electrode, to which a probe DNA is immobilized; introducing an intercalator solution in the chip cartridge; obtaining a current-voltage characteristic curve by measuring a current in the solution due to an electrochemical reaction of the intercalator through the detecting electrode; obtaining a baseline by linearly approximating the current-voltage characteristic curve; obtaining a net current value by subtracting, from a peak current value of the current-voltage characteristic curve, a baseline current value obtained from the baseline at a peak voltage value defining the peak current value; and identifying a nucleotide sequence in the sample DNA, using the net current value.

10 Claims, 28 Drawing Sheets

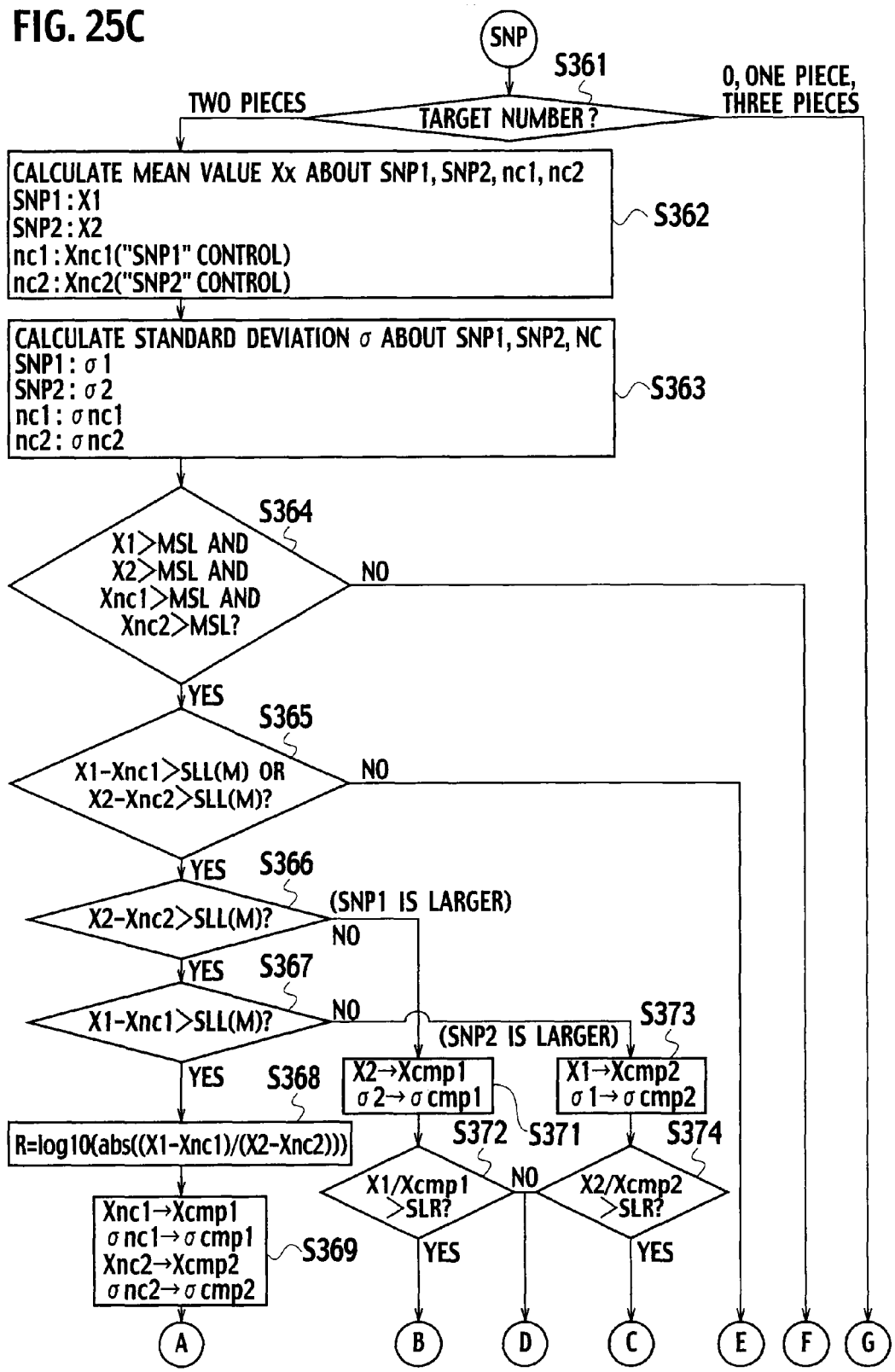

METHOD AND AN APPARATUS FOR DETERMINING NUCLEOTIDE SEQUENCE, AND A COMPUTER PROGRAM PRODUCT TO BE EXECUTED BY THE APPARATUS

CROSS REFERENCE TO RELATED APPLICATIONS

This application is a continuation of and claims the benefit of priority under 35 U.S.C. §120 from U.S. Ser. No. 11/377,265 filed Mar. 17, 2006, and claims the benefit of priority under 35 U.S.C. §119 from Japanese Patent Application No. P2005-78977 filed Mar. 18, 2005, the entire contents of each of which are incorporated by reference herein.

BACKGROUND OF THE INVENTION

1. Field of the Invention

The instant invention relates to a method and an apparatus for determining nucleotide sequence (base sequence), and a computer program product to be executed by the apparatus for determining the nucleotide sequence.

2. Description of the Related Art

The human genome is composed of approximately three billion genetic codes (bases). The "Human Genome Project" currently underway is set to solve the entire genetic code (nucleotide sequence). In this course of events, the fact that many differences exist in the genetic codes (nucleotide sequence) of individual human beings is becoming clear. Differences in human genome nucleotide sequences (polymorphism) are classified into single nucleotide polymorphism (SNP) where one base is substituted with another base, variable number of tandem repeats (VNTR or microsatellite polymorphism) due to an absence or intercalation of between one and several thousand bases, and the like, though currently, single nucleotide polymorphism (SNP) is particularly drawing attention among such types of polymorphism. Single nucleotide polymorphism (SNP) is the difference in one base out of the DNA nucleotide sequence, and is the smallest unit of a human characteristic trait including the ability to handle alcohol and whether drugs have a strong effect. Among the three billion base pairs in the humane genome, it is suggested that approximately three million (a ratio of 1 per 500 to 1000 base pairs) to ten million single nucleotide polymorphism bases exist, which bring about differences in people (physical traits) such as the inability to make particular proteins or the production of proteins difference from other people, racial differences and the like. With respect to research into genetic individual differences in human beings, it is said the analysis of single nucleotide polymorphism and investigation of the susceptibility to diseases and the response to medicines will make made-to-order medical treatment possible where medicine suited to the patient and with few side effects to the patient is administered, and research into single nucleotide polymorphism (SNP) analysis is progressing. For plants, it is possible to identify the mechanism of resistance to disease and pests that the plant has conventionally and enhance those functions.

A reason that can be given why attention is focused on single nucleotide polymorphism (SNP) is the increase in interest in the relationship between disease and SNP because analysis of a variety of SNPs is possible through improvements in analysis techniques. The object of that research spans a wide range including disease-related genes, analysis of the individual differences in drug metabolism, and chronic diseases. The relationship with SNP has been explained for some cases of drug metabolization and lipid metabolism. Future clarifications are expected to gradually develop regarding these issues and SNP.

Molecular biological engineering such as SNP analysis includes a vast number of manipulations on an extremely large number of samples. Those manipulations are frequently complex and time-consuming, and they generally require a high level of precision. For many techniques, the absence of sensitivity, specificity, or reproducibility limits their application.

For example, problems that accompany sensitivity and specificity have thus far limited practical applications of nucleic acid hybridization. "Hybridization" refers to the formation of nucleic acids and the formation of nucleic acid hybrid molecules, and is used as a method for studying the primary structure of nucleic acids, that is the homology of nucleotide sequences, and for detecting nucleic acids having homologous nucleotide sequences. Hydrogen bonds can be formed between base pairs having complementarity whose nucleic acids are in a strand, that is, between adenine (A) and thymine (T) as well as between guanine (G) and cytosine (C), and the characteristic of nucleic acids to form two double helix strands is used. In general, nucleic acid hybridization analysis includes the detection of an extremely small number of specific target nucleic acids (DNA or RNA) from a large volume of non-target nucleic acids using a probe. To maintain a high specificity, hybridization under the strictest of conditions is carried out, ordinarily achieved by variously combining temperature, salts, detergents, solvents, chaotropic agents, and denaturants. The majority of samples, and particularly DNA in human genome DNA samples is associated with extreme complexity. When a sample is made from an extensive number of sequences closely resembling a specific target sequence, a large number of partial hybridizations occur with the non-target sequences even with the most unique of probes. There are also cases where undesirable hybridization kinetics are involved between probe DNA and its specific target (sample DNA). Even under the most favorable of conditions, the majority of hybridization reactions are carried out with relatively low concentrations of probe DNA and target molecules (sample DNA). In addition, probe DNA often competes with complementary sequence for sample DNA. There is also the problem that high-level non-specific background signals are generated because probe DNA has an affinity for almost any substance. Either individually or in combination, these problems thus cause a loss of sensitivity and specificity in nucleic acid hybridization.

Based on such circumstances, the present inventors have already proposed methods (refer to published unexamined patent application 2004-125777) for carrying out significant difference determinations, for example, using a t-test on the size of signals in order to make a determination (of homo-type or hetero-type of bases) of the SNP (single nucleotide polymorphism). In the method described in published unexamined patent application 2004-125777, a hetero-type determination is not made unless the two types of signal values match nearly completely, but in actual measurements, that is impossible.

In this manner, genotyping algorithms for determining the nucleotide sequence of nucleic acids exist in earlier technology, but there are problems with the accuracy of determination.

SUMMARY OF THE INVENTION

In view of these situations, it is an object of the present invention to provide a nucleotide sequence determination method, a nucleotide sequence determination system, and a nucleotide sequence determination program which have a high accuracy in determination and make an immediate determination in practice.

An aspect of the present invention inheres in a method for determining nucleotide sequence encompassing: (a) injecting a solution containing a sample DNA into a chip cartridge provided with a detecting electrode, to which a probe DNA is immobilized; (b) introducing an intercalator solution in the chip cartridge; (c) obtaining a current-voltage characteristic curve by measuring a current in the solution due to an electrochemical reaction of the intercalator through the detecting electrode; (d) obtaining a baseline by linearly approximating the current-voltage characteristic curve; (e) obtaining a net current value by subtracting, from a peak current value of the current-voltage characteristic curve, a baseline current value obtained from the baseline at a peak voltage value defining the peak current value; and (f) identifying a nucleotide sequence in the sample DNA, using the net current value.

Another aspect of the present invention inheres in a method for determining nucleotide sequence encompassing: (a) injecting a sample DNA into a chip cartridge having a plurality of detecting electrodes, on which a probe DNA is immobilized, and a control electrode, on which a DNA which has nucleotide sequence different from the first and second probe DNA is immobilized, or a DNA is not immobilized; (b) obtaining detection signals through the detecting electrodes and control signals through the control electrodes; (c) calculating a mean-value of the detection signals; (d) calculating a mean-value of the control signals; (e) comparing a difference derived by subtracting the mean-value of the control signals from the mean-value of the detection signals with a predetermined signal-increment criterion; and (f) determining the presence of the sample DNA.

Still another aspect of the present invention inheres in a method for determining nucleotide sequence encompassing: (a) injecting a sample DNA into a chip cartridge encompassing:

a plurality of first detecting electrodes, on which a first probe DNA is immobilized, a plurality of second detecting electrodes, on which a second probe DNA, which has nucleotide sequence different from the first probe DNAs is immobilized, and a plurality of control electrodes, on which a control DNA, which has nucleotide sequence different from the first and second probe DNA is immobilized, or a DNA is not immobilized;

(b) obtaining first detection signals through first detecting electrodes, second detection signals through second detecting electrodes, and control signals through control electrodes; (c) calculating mean-values of the first detection signals, the second detection signals, and the control signals, respectively; (d) comparing a first mean-value difference derived by subtracting the mean-value of the control signals from the mean-value of the first detection signals with a predetermined signal-increment criterion, and comparing a second mean-value difference derived by subtracting the mean-value of the control signals from the mean-value of the second detection signals with the predetermined signal-increment criterion; and (e) proceeding to a procedure for genotyping the sample DNA, when at least one of the first and the second mean-value differences is equal to or larger than the predetermined signal-increment criterion, and determining that the genotyping is not possible when both the first and the second mean-value differences is smaller than the predetermined signal-increment criterion.

Yet still another aspect of the present invention inheres in an apparatus for determining nucleotide sequence encompassing: (a) a chip cartridge having:

a plurality of first detecting electrodes on which a first probe DNA is immobilized, a plurality of second detecting electrodes, on which a second probe DNA which has nucleotide sequence different from the first probe DNAs is immobilized, and a plurality of control electrodes, on which a control DNA, which has nucleotide sequence different from the first and second probe DNA is immobilized, or a DNA is not immobilized;

(b) a detecting system for measuring currents through the first detecting electrodes, the second detecting electrodes, and the control electrodes; (c) a current-profile judgement module configured to acquire first detection signals from the first detecting electrodes, second detection signals from the second detecting electrodes, and control signals from the control electrodes, as current-voltage characteristic curves through the detecting system, to obtain slopes of tail lines in each of the current-voltage characteristic curves, to assign normality or abnormality of the current-voltage characteristics curve from the slopes of the tail lines, and to exclude abnormal detection signals from calculation object; and (d) a net current calculation module configured to subtract a baseline current value from the current-voltage characteristic curves measured by the first detection signals, the second detection signals, and the control signals from corresponding peak currents in the current-voltage characteristic curves measured by the first detection signals, the second detection signals, and the control signals, respectively, so as to obtain net currents for the first detection signals, the second detection signals, and the control signals.

Further aspect of the present invention inheres in a computer program product to be executed by an apparatus for determining nucleotide sequence, the computer program product encompassing: (a) instructions configured to obtain first detection signals through first detecting electrodes, second detection signals through second detecting electrodes, and control signals through control electrodes, after injecting a sample DNA into a chip cartridge encompassing:

a plurality of first detecting electrodes on which a first probe DNA is immobilized, a plurality of second detecting electrodes, on which a second probe DNA, which has nucleotide sequence different from the first probe DNAs is immobilized, and a plurality of control electrodes, on which a control DNA, which has nucleotide sequence different from the first and second probe DNA is immobilized, or a DNA is not immobilized;

(b) instructions configured to calculate mean-values of the first detection signals, the second detection signals, and the control signals, and (c) instructions configured to compare a first mean-value difference derived by subtracting the mean-value of the control signals from the mean-value of the first detection signals with a predetermined signal-increment criterion, and comparing a second mean-value difference derived by subtracting the mean-value of the control signals from the mean-value of the second detection signals with the predetermined signal-increment criterion, wherein the apparatus proceeds to a procedure for genotyping the sample DNA, when at least one of the first and the second mean-value differences is equal to or larger than the signal-increment criterion, and determine that the genotyping is not possible when both the first and the second mean-value differences is smaller than the signal-increment criterion.

BRIEF DESCRIPTION OF THE DRAWINGS

Various embodiments of the present invention will be described with reference to the accompanying drawings. It is to be noted that the same or similar reference numerals are applied to the same or similar parts and elements throughout the drawings, and the description of the same or similar parts and elements will be omitted or simplified.

Generally and as it is conventional in the representation of semiconductor devices, it will be appreciated that the various drawings are not drawn to scale from one figure to another nor inside a given figure, and in particular that the layer thicknesses are arbitrarily drawn for facilitating the reading of the drawings.

FIG. 25C is a flow chart explaining one example of the algorithm for determining which of the two kinds of SNP type, the SNP="G" or the SNP="T", is present, or whether the SNP type is the homo-type or the hetero-type, in the nucleotide sequence determination method according to the embodiment of the present invention;

DETAILED DESCRIPTION OF THE EMBODIMENTS

In the following description specific details are set forth, such as specific materials, processes and equipment in order to provide a thorough understanding of the present invention. It will be apparent, however, to one skilled in the art that the present invention may be practiced without these specific details. In other instances, well-known manufacturing materials, processes and equipment are not set forth in detail in order not to unnecessarily obscure the present invention.

Prepositions, such as "on", "over", "under", "beneath", and "normal" are defined with respect to a planar surface of the substrate, regardless of the orientation in which the substrate is actually held. A layer is on another layer even if there are intervening layers.

Nucleotide Sequence Determination System

Figure 1:
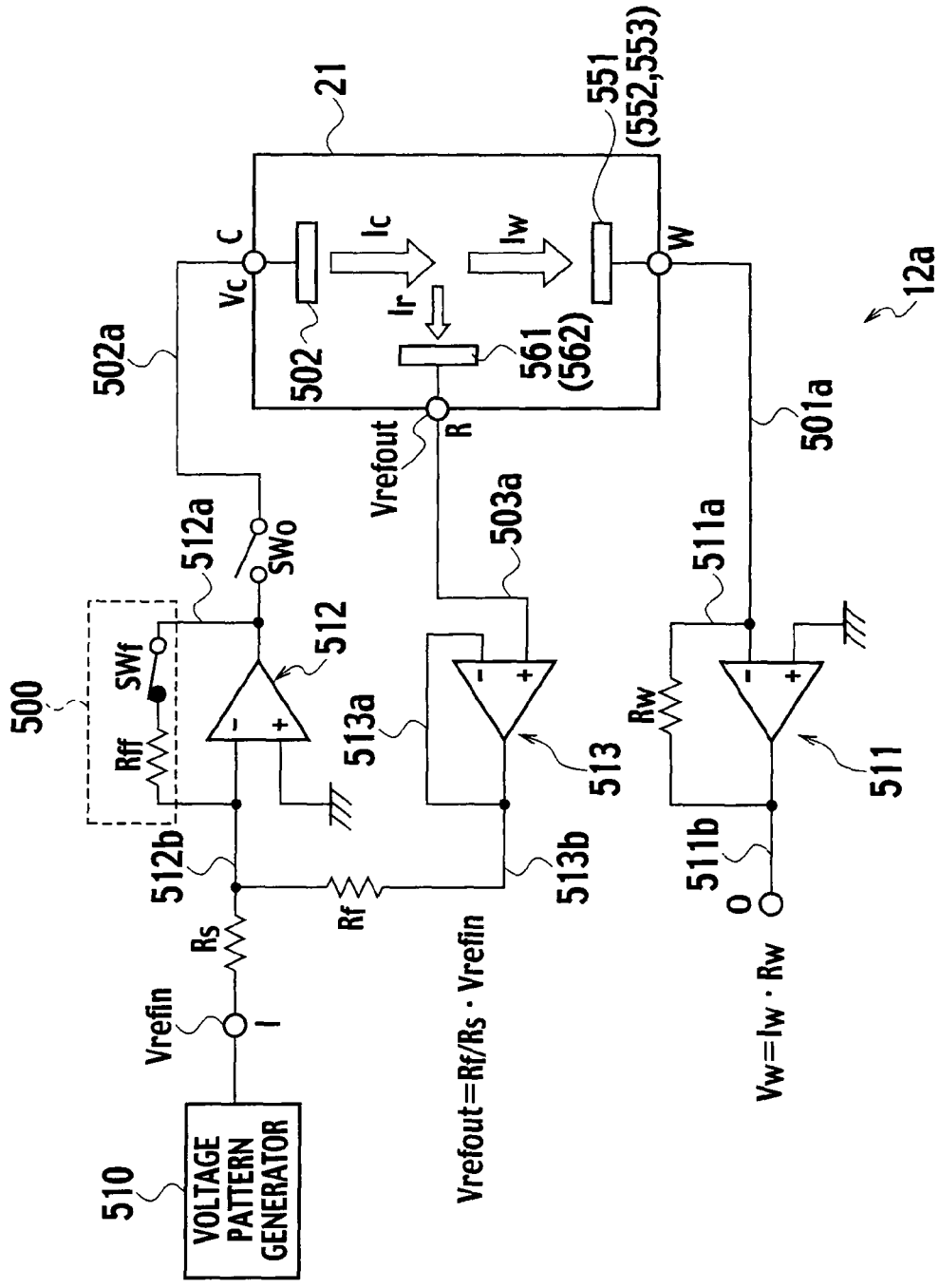
FIG. 1 is a schematic diagram explaining one example of a detecting system that implements the nucleotide sequence determination system according to an embodiment of the present invention.
Figure 7:
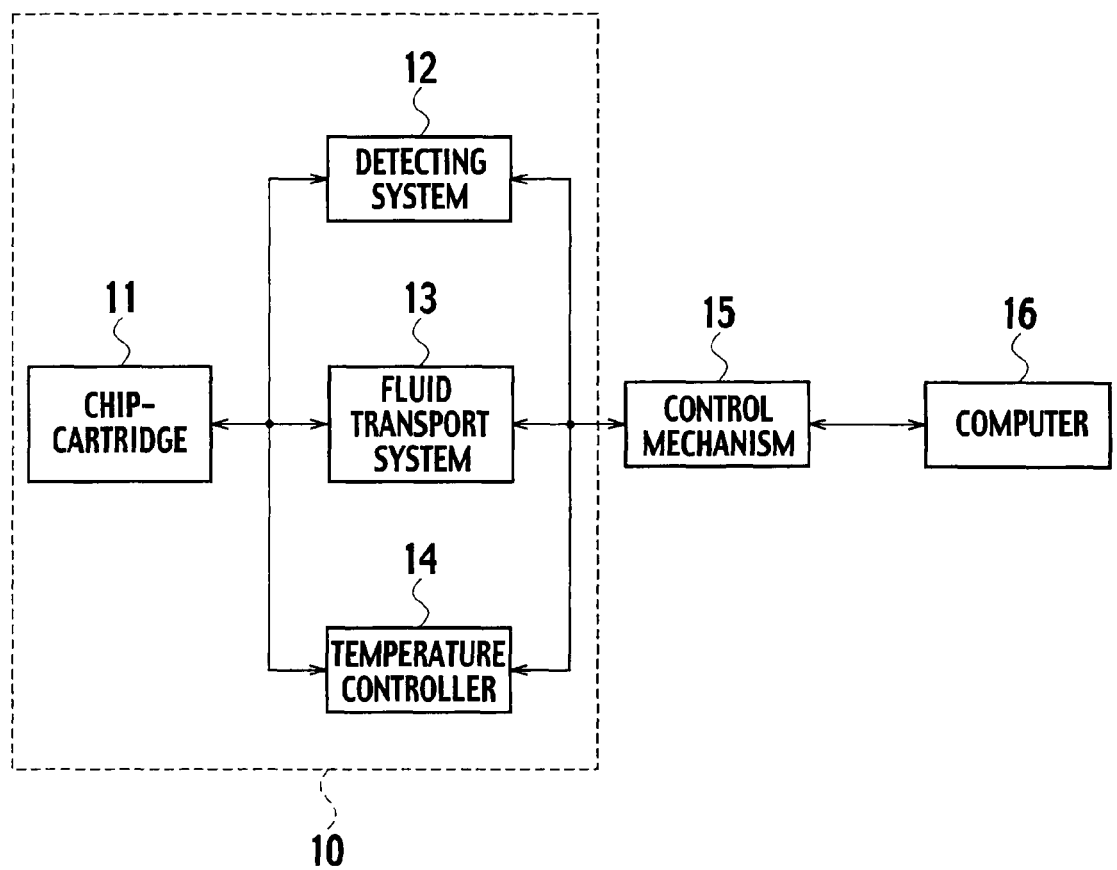
FIG. 7 is a logical block diagram explaining one example of the nucleotide sequence determination system according to the embodiment of the present invention.

As shown in FIG. 7, a nucleotide sequence determination system according to an embodiment of the present invention encompasses a chip cartridge 11, a detecting system 12 electrically connected to the chip cartridge 11, a fluid transport system 13 physically connected through an interface portion to a flow channel provided at the chip cartridge 11, a temperature controller 14 for controlling the temperature of the chip cartridge 11, and the like. The detecting system 12 of FIG. 7 is implemented by a potentiostat, which facilitates an electrochemical measuring analysis based on a three-electrode method, by applying a desired voltage in a solution not affected by fluctuation in conditions such as of the electrodes and solution in the cell because of feedback (a negative feedback) of the voltage of reference electrodes 561 and 562 to the input of an opposite electrode 502 as shown in FIG. 1, and connects terminals C, R, and W of a detection chip 21. The chip cartridge 11 of FIG. 7 embraces the detection chip 21 of FIG. 1.

Figure 2:
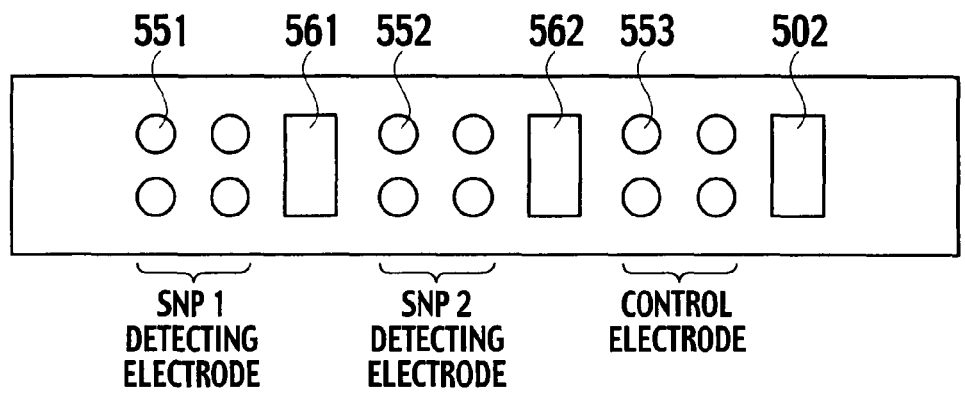
FIG. 2 is a representational plan view explaining the configuration of a detection chip that implements part of the detecting system in FIG. 1.

As shown in FIG. 2, on a top surface of the detection chip 21, a plurality of active electrodes 551, each of which is assigned as a first SNP detecting electrode (SNP1 detecting electrode), a plurality of active electrode 552, each of which is assigned as a second SNP detecting electrode (SNP2 detecting electrode), a plurality of active electrode 553, each of which is assigned as a control electrode so as to implement an electrode unit. Furthermore, a couple of reference electrodes 561 and 562 and an opposite electrode 502 opposing the active electrodes 551, 552, and 553, are arranged so as to implement the electrode unit as shown in FIG. 2. In further detail, the detecting system 12 changes the voltage of the reference electrodes 561 and 562 with respect to the voltage of the opposite electrode 502 so as to establish prescribed characteristics, the reference electrodes 561 and 562 correspond to the active electrodes 551, 552, and 553, and electrochemically measures the current due to an electrochemical reaction of the intercalation agent (hereinafter, referred to as the "electrochemical current").

Figure 3A:
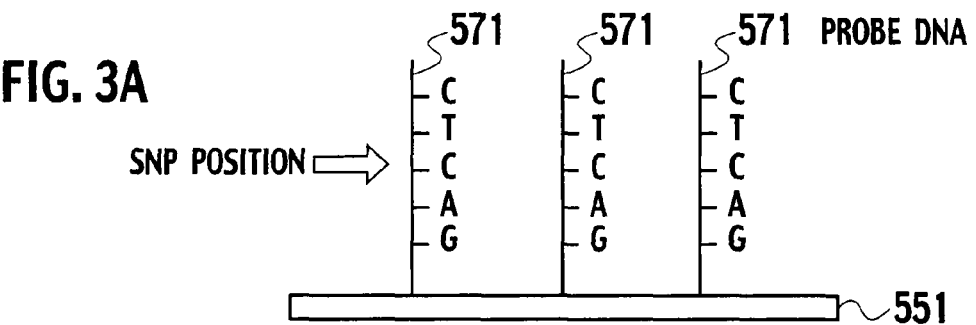
FIG. 3A is a schematic plot depicting three strands of probe DNAs, endowed with nucleotide sequence GACTC . . . , immobilized to a top surface of an SNP="G" detecting electrode.

In the nucleotide sequence determination method according to the embodiment of the present invention, probe DNAs 571 and 572 having complementary nucleotide sequences with target nucleotide sequences (sample DNAs) 581, 582, and 583 as shown in FIGS. 9A, 9B, 9C, 10A, 10B, 10C, 11A, 11B, and 11C, are firstly fixed to the active electrodes 551 and 552, respectively, the sample DNAs 581, 582, and 583 are the targets of nucleotide sequence determination. In further detail, as shown in FIG. 3A, the active electrode 551 is an electrode configured to immobilize the probe DNA 571 having a nucleotide sequence GACTC..., which is complementary to the target nucleotide sequence (sample DNA) 581 having the nucleotide sequence CTGAG... shown in FIG. 9A. In FIG. 3A, the base at the SNP position is assigned at C, the third from the bottom, so the detecting electrode is prescribed as a "G" detecting electrode.

Figure 3B:
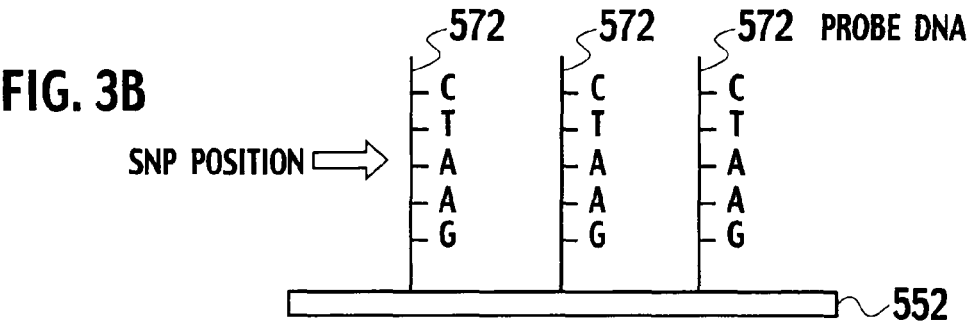
FIG. 3B is a schematic plot depicting three strands of probe DNA, endowed with nucleotide sequence GAATC . . . , immobilized to a top surface of an SNP="T" detecting electrode.
Figure 10A:
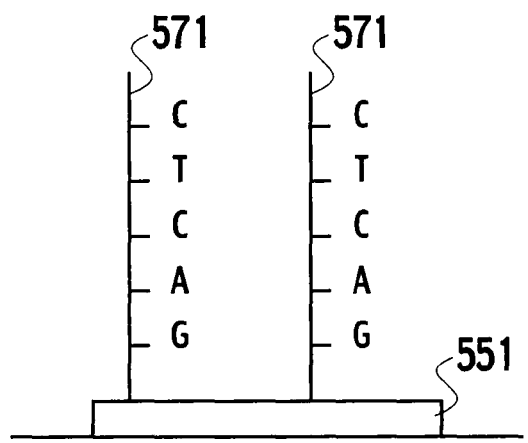
FIG. 10A is a schematic plot depicting two strands of probe DNAs, immobilized to the top surface of the SNP="T" detecting electrode, showing that sample DNA with SNP="T" is unable to form a double-strand with probe DNAs.
Figure 10B:
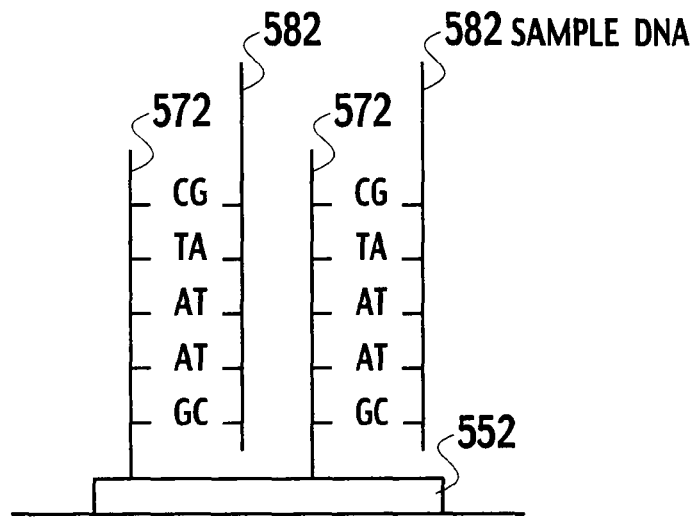
FIG. 10B is a schematic plot depicting two strands of probe DNA, immobilized to the top surface of the SNP="T" detecting electrode, and two strands of sample DNA with SNP="T", which are paired into double-strands with the probe DNAs, because the nucleotide sequences match perfectly with the probe DNAs.

As shown in FIG. 3B, the active electrode 552 is an electrode configured to immobilize the probe DNA 572 having a sequence base GAATC..., which is complementary to the target nucleotide sequence (sample DNA) 582 having the nucleotide sequence CTTAG... shown in FIG. 10B. In FIG. 3B as well, the base at the SNP position is assigned at "A", the third from the bottom, so the detecting electrode is prescribed as a "T" detecting electrode.

Figure 3C:
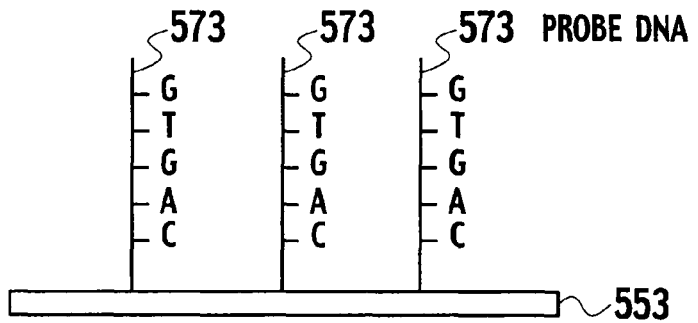
FIG. 3C is a schematic plot depicting three strands of probe DNA (negative control DNA), endowed with nucleotide sequence CAGTG . . . immobilized to a top surface of a control electrode.

As shown in FIG. 3C, the active electrode 553 is a control electrode for immobilizing a probe DNA (negative control DNA) 573 having the nucleotide sequence CAGTG... not complementary to the target nucleotide sequences (sample DNAs) 581 or 582. The active electrodes 551, 552, and 553 detect a reaction current in the cell. The types of the probe DNAs 571, 572, and 573 immobilized to the active electrodes 551, 552, and 553 are merely exemplifications, but there must be one type of probe DNA immobilized to each of the active electrodes 551, 552, and 553 as a general rule.

Between the opposite electrode 502 and the active electrode 551, between the opposite electrode 502 and the active electrode 552, and between the opposite electrode 502 and the active electrode 553, a predetermined voltage is applied respectively so as to establish corresponding current in the cell.

Through the reference electrodes 561 and 562, a voltage between the reference electrode 561 and the active electrode 551, a voltage between the reference electrode 561 and the active electrode 552, a voltage between the reference electrode 562 and the active electrode 552, and a voltage between the reference electrode 562 and the active electrode 553 are feed back to the opposite electrode 502 so as to regulate each of the voltages between the reference electrodes 561, 562 and the active electrodes 551, 552, and 553 in predetermined voltage characteristics; the voltage is thereby controlled by the opposite electrode 502, so the electrochemical current can be detected with a high level of precision without being affected by various detection conditions in the cell.

As shown in FIG. 1, the detecting system 12 in the nucleotide sequence determination system according to the embodiment of the present invention encompasses a voltage pattern generator 510 configured to generate a voltage pattern for detecting current flowing between electrodes. The voltage pattern generator 510 is connected to an inverting input terminal of an inverting amplifier (OPc) 512 configured to regulate the reference voltage of the reference electrodes 561 and 562 through an input wire 512b. The voltage pattern generator 510 encompasses a DA converter so that the voltage pattern generator 510 can convert digital signal, transmitted from the control mechanism 15 shown in FIG. 7, to analog signal, while generating a voltage pattern. A resister $R_s$ is connected to the input wire 512b between a terminal "I" and the inverting input terminal of the inverting amplifier (OPc) 512. The non-inverting input terminal of the inverting amplifier 512 is grounded, and an output wire 502a is connected to between the output terminal of the inverting amplifier 512 and a terminal "C". The input wire 512b at the inverting input terminal side and the output wire 502a at the output terminal side of the inverting amplifier 512 are connected by a bypass feedback wire 512a branching from the input wire 512b and the output wire 502a, respectively. A protection circuit 500 encompassing a feedback resistor $R_{ff}$ and a switch $SW_f$ is provided at the feedback wire 512a. The output wire 502a is connected to a terminal "C" of the detection chip 21. The terminal "C" is connected to the opposite electrode 502 on the detection chip 21. If a plurality of opposite electrodes 502 are provided, a plurality of terminals C corresponding to the plurality of opposite electrodes 502 are provided in parallel. Voltage can thereby be applied simultaneously to the plurality of opposite electrodes 502 with one voltage pattern. The output wire 502a is provided with a switch $SW_O$ for turning the voltage to the terminal(s) "C" on and off.

The protection circuit 500 shunting between the input and output of the inverting amplifier 512 forms a circuit such as to prevent excess voltage from being applied to the opposite electrode 502. An excess of voltage is therefore not applied during measurement and the solution is not electrically dissolved, making stable measurement possible without an effect on the electrochemical detection of the desired intercalation agent.

The terminal "R" of the detection chip 21 is connected to a non-inverting input terminal of a voltage follower amplifier (OP$_r$) 513 by an input wire 503a. Between the inverting input terminal and the output terminal of the voltage follower amplifier 513 is shorted by a wire 513a. An output wire 513b is connected between the output terminal of the voltage follower amplifier 513 and a node on the input wire 512b, through a resister $R_f$ provided on the output wire 513b, the node on the input wire 512b is assigned to a connection point between the output side of resistor Rs and the input wire 512b, which serves as a branching point of the feedback wire 512a and the input wire 512b. That is, the resister $R_f$ is provided between the output terminal of the voltage follower amplifier 513 and the node on the input wire 512b. Based on the output of inverse amplified voltage supplied from the inverse amplifier 512, by delivering a feedback voltage transferred from the reference electrodes 561 and 562 to the inverting input terminal of the inverting amplifier 512, the voltage pattern generated by the voltage pattern generation current 510 is feedback-controlled so as to provide a controlled voltage to the opposite electrode 502.

The terminal "W" of the detection chip 21 is connected to the inverting input terminal of a transimpedance amplifier (OP$_W$) 511 by an input wire 501a. The non-inverting input terminal of the transimpedance amplifier 511 is grounded. From an output wire 511b connected to the output terminal of the transimpedance amplifier 511, a feedback wire 511a is branched so as to connect with the input wire 501a. A feedback resistor RW is provided at the feedback wire 511a so as to shunt between the input side and the output side of the transimpedance amplifier (OP$_W$) 511.

If the voltage of a terminal "O" on the output side of the transimpedance amplifier 511 is $V_W$ and the current is $I_W$, then:

$$V_W = I_W \cdot R_W \qquad (1)$$

The electrochemical signals obtained from the terminal "O" are transferred to the regulation mechanism shown in FIG. 7. Because a plurality of sets of active electrodes (551, 552, and 553) are provided, a plurality of terminals "W" and terminals "O" are provided corresponding to the number of the sets of active electrodes (551, 552, and 553). Respective outputs from the plurality of terminals "O" are sequentially switched by a signal switching portion described below, and electrochemical signals from the plurality of sets of active electrodes (551, 552, and 553) can be obtained nearly simultaneously as a set of digital values through AD conversion. A common Circuit such as the transimpedance amplifier 511, to be provided between the terminal "W" and the terminal "O", may share the plurality of sets of active electrodes (551, 552, and 553). In such a common sharing configuration, a signal switching portion may be provided to switch each of the plurality of wires from the plurality of terminals "W" to a single input wire 501a.

Figure 4:
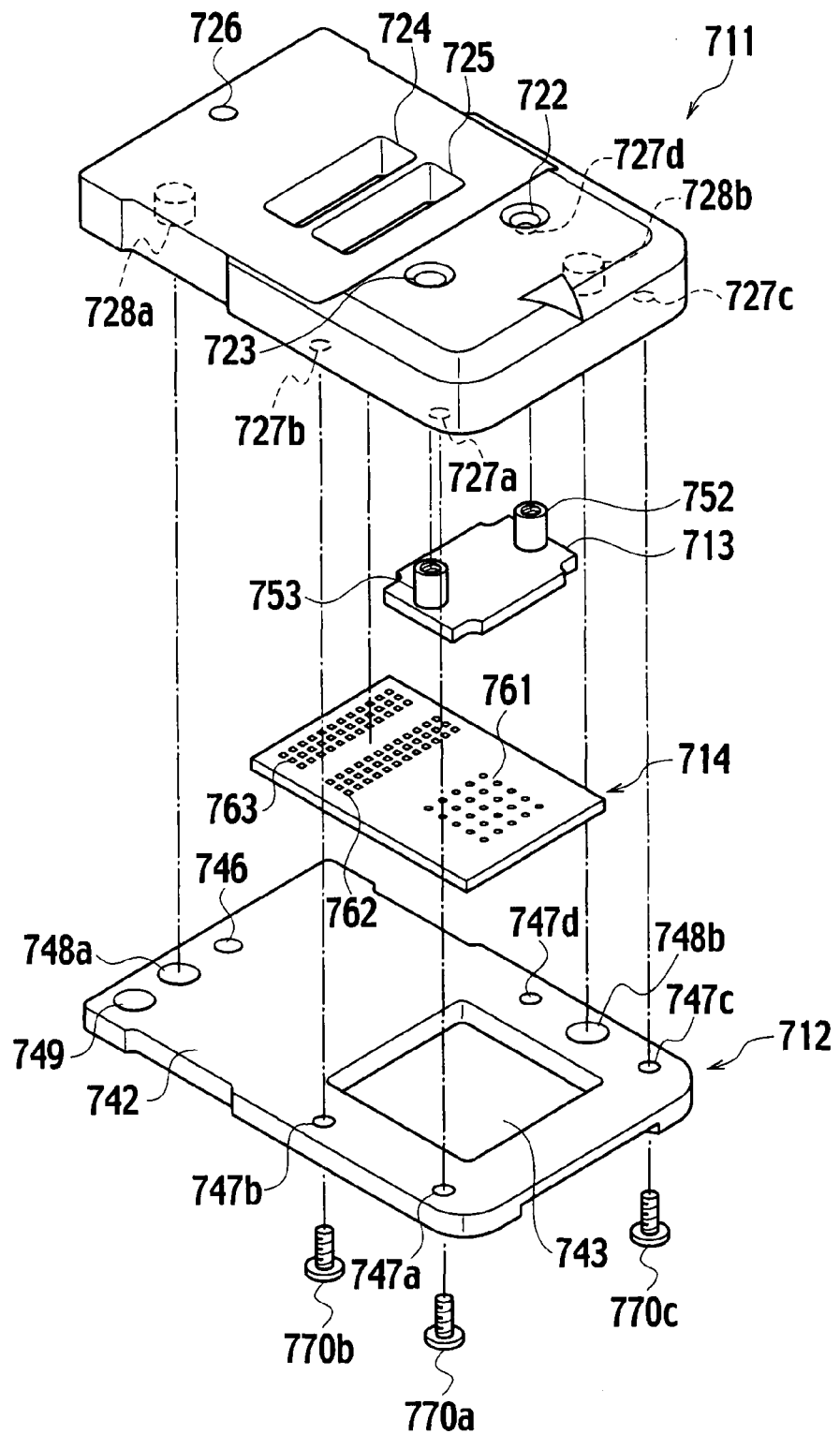
FIG. 4 is a bird's eye view of a representational construction explaining one example of the configuration of a chip cartridge used in the nucleotide sequence determination system according to the embodiment of the present invention.
Figure 5:
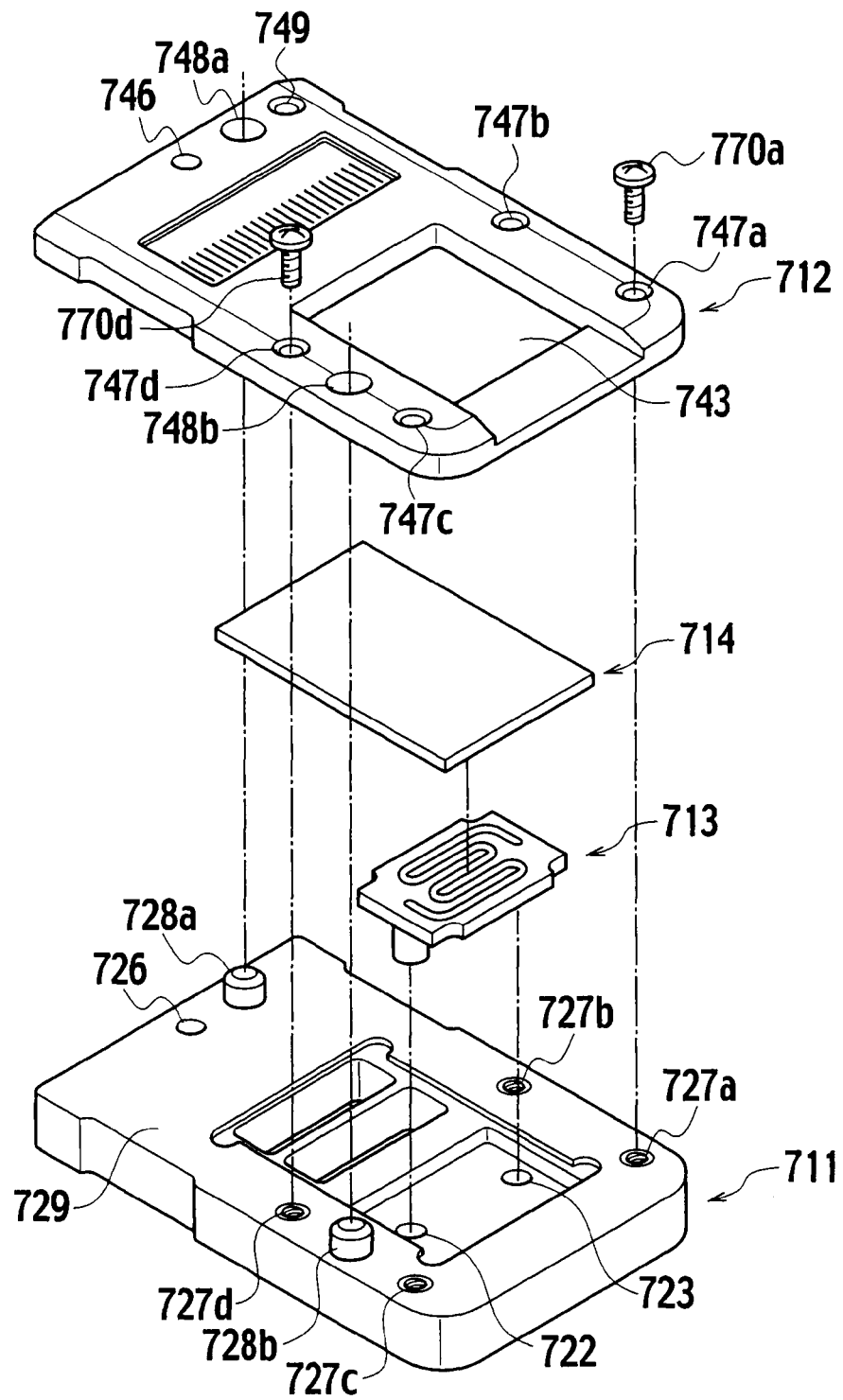
FIG. 5 is an inverted bird's eye view of the construction of the chip cartridge in FIG. 4.

As shown in FIGS. 4 and 5, the chip cartridge 11 implementing the nucleotide sequence determination system of FIG. 7 encompasses a cassette made from a cassette top lid 711, a cassette bottom lid 712, packing-plate 713 (a seal member), and a substrate 714. The inner surfaces of the cassette top lid 711 and the cassette bottom lid 712 are in opposition and are fixed such as to surround the packing-plate 713 and the substrate 714. From the outer surface to the inner surface of the cassette top lid 711, a couple of nozzle intercalation holes 722 and 723 are passing through, the cross-sectional view of the nozzle intercalation holes 722 and 723 cut perpendicular to the direction along the outer surface to the inner surface of the cassette top lid 711 is roughly circular geometry.

Figure 6:
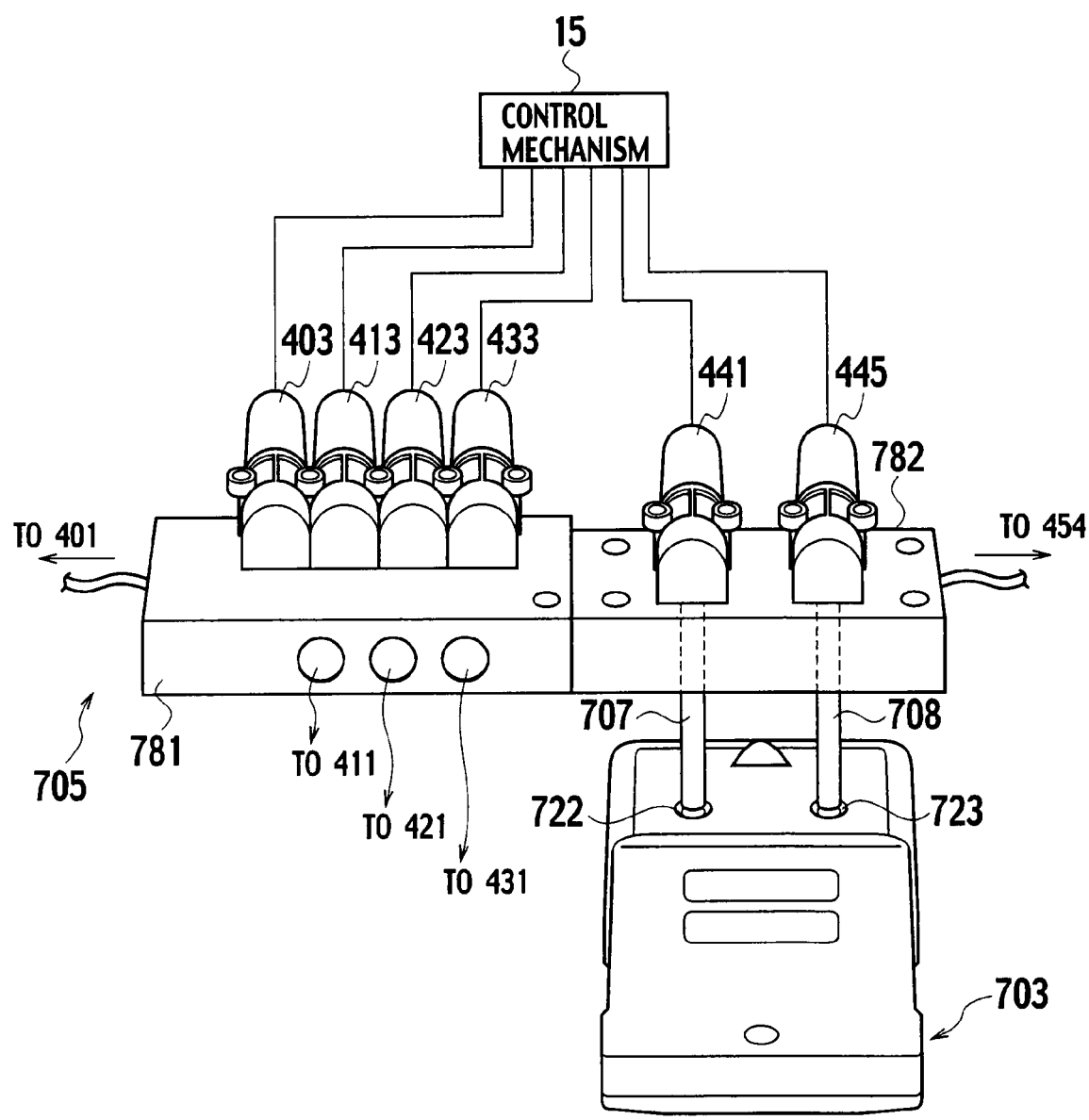
FIG. 6 is a schematic plot depicting the overall construction of a valve unit of a fluid transport system that implements the nucleotide sequence determination system according to the embodiment of the present invention.

The inner diameter of the circular nozzle intercalation holes 722 and 723 is set to about 3.2 mm, for example, slightly larger than the outer diameter of nozzles 707 and 708 of FIG. 6 and the inlet and outlet ports 752 and 753. As shown in FIG. 4, from the outer surface to the inner surface of the cassette top lid 711, a couple of windows, or electrical connector ports 724 and 725 are passing through, the cross-sectional view of the electrical connector ports 724 and 725 cut perpendicular to the direction along the outer surface to the inner surface of the cassette top lid 711 is roughly rectangular geometry. The electrical connector ports 724 and 725 are windows, which are configured to be inserted with electrical connectors described below. Also, a seal detection hole 726 is formed to pass from the outer surface through to the inner surface. The seal detection hole 726 is used for detecting the presence of a seal. In further detail, a solution (sample) is injected into the cassette (detection chip) 21 with a seal affixed from the surface of the seal detection hole 726 on the outer surface of the cassette (detection chip) 21 to the surface of the electrical connector ports 724 and 725, and after injection of the solution (sample) into the cassette (detection chip) 21, the seal is removed, and detection is made for presence of the seal. By injecting the solution (sample) into the cassette (detection chip) 21 with the seal affixed, there is no concern that a malfunction will occur such as an electrical short as liquid does not actually enter inside the electrical connector ports 724 or 725 even if the solution (sample) should mistakenly drip onto the electrical connector ports 724 or 725 because they are covered with the seal.

As shown in FIG. 5, a substrate alignment groove with a predetermined depth and a cross-sectional shape nearly identical to the cross-sectional shape of the substrate 714 is provided at the inner surface side of the cassette top lid 711 and is surrounded by the inner surface, the cross-sectional shape corresponds to a cross-section cut perpendicular to the direction along the outer surface to the inner surface of the cassette top lid 711. The substrate alignment groove is formed so as to occupy an area overlapping with the locations where nozzle intercalation holes 722 and 723 as well as the electrical connector ports 724 and 725 are disposed. By inserting the substrate 714 to fit the substrate alignment groove, the substrate 714 can be disposed to match the position of the cassette top lid 711. The substrate alignment groove is formed so that its depth is roughly the same as the thickness of the substrate 714.

As shown in FIG. 5, a packing-plate guiding groove even deeper than the substrate alignment groove is provided so as to overlap with the area of the substrate alignment groove at the inner surface side of the cassette top lid 711, and the perimeter of the packing-plate guiding groove is surrounded by the substrate alignment groove. The lateral area of the packing-plate guiding groove is formed so as to overlap with an area where the nozzle intercalation holes 722 and 723 are located. A packing-plate 713 can be inserted aligned with the packing-plate guiding groove so as to be positioned at the cassette top lid 711. The depth, with regard to the horizontal level of the substrate alignment groove, of the packing-plate guiding groove is selected so as to have approximately the same thickness as the thickness of the packing-plate 713 described below. Accordingly, with regard to the horizontal level of the inner surface of the cassette bottom lid 712, the depth of the packing-plate guiding groove is determined such as to be approximately the same to the sum of the thickness of the packing-plate 713 and the thickness of the substrate 714.

Four screw holes 727a, 727b, 727c, and 727d are provided at the periphery of the inner surface of the cassette top lid 711. The cassette top lid 711 and the cassette bottom lid 712 can be screwed together with these screw holes 727a, 727b, 727c, and 727d. Two cassette positioning holes 728a and 728b are provided at the periphery of the inner surface of the cassette top lid 711. By disposing the cassette (detection chip) 21 in alignment with two positioning pins provided on a slide stage of the nucleotide sequence determination system, the cassette (detection chip) 21 can be positioned and aligned with respect to the slide stage.

A seal detection hole 746 is formed to pass through the outer surface of the cassette bottom lid 712. The seal detection hole 746 of the cassette bottom lid 712 is formed at a position communicating with the seal detection hole 726 of the cassette top lid 711 when the cassette top lid 711 and the cassette bottom lid 712 are closed together. The penetrating seal detection hole 726 is thereby provided from the cassette top lid 711 to the cassette bottom lid 712, so that detection light can be irradiated on the seal detection hole 726 when the cassette top lid 711 and the cassette bottom lid 712 are closed together, and the presence of a seal can thereby be determined.

Four screw holes 747a, 747b, 747c, and 747d are provided at the periphery portion of the outer surface of the cassette lower lid 712. By twisting screws into the corresponding screw holes 727a to 727d provided at the cassette top lid 711, the cassette bottom lid 712 can be fastened to the cassette top lid 711. Two cassette positioning holes 748a and 748b are provided at the periphery of the outer surface of the cassette bottom lid 712. Cassette positioning holes 728a and 728b of the cassette top lid 711 pass through the cassette positioning holes 748a and 748b, respectively. Positioning of the cassette (detection chip) 21 with respect to the slide stage is established, regulated by the two positioning pins provided on the slide stage of the nucleotide sequence determination system and the two positioning holes 728a and 728b of the cassette top lid 711 passing through the cassette positioning holes 748a and 748b of the cassette bottom lid 712. Also, a cassette type identification hole 749 is provided at the cassette bottom lid 712, and the type of the cassette (detection chip) 21 can be identified according to the presence or absence of the cassette type identification hole 749. Type identification can be carried out automatically by judging whether the lowering of the cassette type identification pin (illustration omitted) is conducted or not. The state of lowering the cassette type identification pin (illustration omitted) is detected by the control mechanism 15.

Even if a cassette (detection chip) 21 is used without a cassette type identification hole 749 provided, it is possible to measure in a similar manner with only the difference in the types of the cassettes (detection chips) 21 being identified. Alternatively, a design may be made where the difference in the types of the cassettes (detection chips) 21 is displayed on a display unit (illustration omitted) by the control mechanism 15, a warning given off, and the process stopped before measurement. As another alternative, an anchored anchoring pin may be used for the cassette type identification pin (illustration omitted) and an architecture can be designed such that a cassette (detection chip) 21 not provided with the cassette type identification hole 749 cannot be attached, thereby preventing the wrong cassette (detection chip) 21 from being set in place.

As shown in FIG. 4, the packing-plate 713 encompasses a roughly rectangular plate portion with a prescribed thickness formed with the four corners notched, and a cylindrical inlet port 752 and outlet port 753 positioned near either of the long ends on the main surface of the plate portion and provided near the center of the short ends. Openings are provided at the ends of the inlet port 752 and the outlet port 753. A flow channel is provided along a direction perpendicular to the main surface of the plate portion at the axial centers of the inlet port 752 and the outlet port 753. As shown in FIG. 5, the backside of the plate portion has a meandering groove formed in a twisting form from the allocation position of the inlet port 752 to the allocation position of the outlet port 753. The meandering groove implements a meandering flow channel. The meandering groove is formed such as to proceed back and forth a plurality of times, and each of the twist points of the meandering groove has a predetermined curvature ratio so as to suppress accumulation of solution or air that would occur when sharp corners or the like are provided for the twist points.

As shown in FIG. 4, a plurality of electrode units 761, a plurality of pads 762 and a plurality of pads 763 are arranged at the main surface of the substrate 714. As shown in FIG. 2, each of the electrode units 761 is implemented by a three-electrode configuration made from a combination of the opposite electrode 502, the active electrodes 551, 552, and 553, and the reference electrodes 561 and 562. Probe DNAs 571, 572, and 573 are immobilized to the active electrodes 551, 552, and 553 in each of the plurality of electrode units 761. Each of the plurality of electrode units 761 is connected to the corresponding pad 762 and the corresponding pad 763 by wires not illustrated. A case is exemplified in FIG. 4 where the plurality of electrode units 761 for immobilizing a plurality of probe DNAs, the plurality of pads 762 and the plurality of pads 763 are formed on the same surface of the substrate 714, though if the plurality of pads 762 and the plurality of pads 763 are formed on the opposite side of the substrate 714 than that on which the plurality of electrode units 761 are formed, a valve unit 705 may be disposed above the cassette (detection chip) 21, and a probe unit 710 may be disposed below the cassette (detection chip) 21. In that case, the valve unit 705 and the probe unit 710 need not necessarily be integrated as one unit.

The arrangement for the plurality of electrode units 761 is made to match the allocation route of the meandering flow channel at the position of the packing-plate. When the packing-plate 713 and the substrate 714 are anchored in a state fastened by the cassette top lid 711 and the cassette bottom lid 712, a meandering flow channel is thereby formed by the meandering groove and the surface of the substrate 714, and the plurality of electrode units 761 protrude to the surface of the meandering flow channel. In further detail, a meandering gap is provided by the meandering groove against to the plurality of electrode units 761, and the meandering flow channel is formed by the meandering gap. In this state, a seal is provided between the packing-plate 713 and the substrate 714.

(a) Firstly, the packing-plate 713 is fit together in the packing-plate guiding groove by intercalation so as to match the packing-plate guiding groove of the inner surface of the cassette top lid 711 and such that the inlet port 752 and the outlet port 753 accommodate the nozzle intercalation holes 722 and 723.

(b) Then, the substrate 714 is provided at the substrate alignment groove such that one of the main surfaces of the substrate 714, that is, the surface on which the plurality of electrode units 761 and the plurality of pads 762 and the plurality of pads 763 are arranged, faces to the cassette top lid 711.

(c) Then, the cassette bottom lid 712 is placed on the cassette top lid 711 such that the inner surface 742 of the cassette bottom lid 712 faces the cassette top lid 711 and that the positions of the screw holes 747a to 747d and the screw holes 727a to 727d are aligned.

(d) The screws 770a to 770d are then inserted by twisting them into the screw holes 747a to 747d and the screw holes 727a to 727d. The cassette top lid 711 and the cassette bottom lid 712 are thereby tightened by screws, and the packing-plate 713 and the substrate 714 are fixed between the cassette top lid 711 and the cassette bottom lid 712, thereby completing the cassette (detection chip) 21. In this completed state, the meandering flow channel is formed so as to route from the nozzle intercalation hole 722 to the nozzle intercalation hole 723.

In FIGS. 4 and 5, an example is shown where a plurality of screws fasten the cassette top lid 711 and the cassette bottom lid 712, but the invention is not limited the screw-fastening configuration. A locking method may also be used where a concavo-convex member, for example, is mutually adopted so as to tighten the concave member with the convex member.

FIG. 6 shows an entire configuration of a valve unit 705 provided in the fluid transport system 13 so as to implement the nucleotide sequence determination system according to the embodiment of the present invention. In FIG. 6, the configuration of the probe unit is omitted; the probe unit is integrated as one unit with the valve unit 705, and the valve unit and the probe unit are driven simultaneously by a valve-unit-probe-unit-drive mechanism. For example, two electrical connectors are disposed at predetermined intervals at the probe unit encompassing a glass epoxy substrate and the like. A plurality of convex electrodes are arranged at the ends of the electrical connectors in a matrix form with the same arrangement as the pads on the substrate 714, and these convex electrodes are in contact with the plurality of pads 762 and the plurality of pads 763 of the substrate 714 shown in FIG. 4, thereby ensuring electrical connections between the substrate 714 and the probe unit. A plurality of wire are provided in the electrical connectors, electrically connecting the convex electrodes and the control mechanism 15.

The valve-unit-probe-unit-drive mechanism is driven automatically by instructions from the control mechanism 15. The valve-unit-probe-unit-drive mechanism has a vertical drive direction. When the nozzles 707 and 708 and the bunch of electrical connectors 703 are thereby lowered relative to the upper portion of the cassette (detection chip) 21 on the slide stage side, the nozzles 707 and 708 are thereby positioned at the nozzle intercalation holes 722 and 723, and two bunches of electrical connectors 703 are positioned respectively at the electrical connector ports 724 and 725 as shown in FIG. 6. The meandering flow channel inside the cassette (detection chip) 21 and the fluid transport system 13 communicate each other so that liquid solution can be conveyed automatically. Also, the electrical connectors are positioned at the plurality of pads 762 and the plurality of pads 763 of the cassette (detection chip) 21, electrically connecting the plurality of pads 762 and the plurality of pads 763 with the bunch of electrical connectors.

The valve unit 705 embraces a plurality of valve bodies 781 and 782, establishing a linking connection with each other, although a couple of valve bodies 781 and 782 is shown in FIG. 6 so as to simplify the drawing. A two-way electromagnetic valve 403 and three-way electromagnetic valves 413, 423, and 433 are provided at the valve body 781, and three-wavy electromagnetic valves 441 and 445 are provided at the valve body 782. The valve body 781 may be manufactured from polyether-ether-ketone (PEEK™) resin, for example. For a case that the valve body 781 and the valve body 782 are manufactured separately, and polytetrafluoroethylene (PTFE) resin, for example, is used as packing material for the joint portion if the two are joined. Accordingly, the material of the portion of both valve bodies 781 and 782 that comes into contact with solution may be made from PEEK™ or PTFE. A cavity with a fairly standardized cross-section is provided in each of the valve bodies 781 and 782. The cavity functions as a pipe to provide a connection between electromagnetic valves described below, the packing-plate 713, and the like. The nozzles 707 and 708 communicate at the cavity provided at the valve body 782. The nozzle 707 and the nozzle 708 may be made from PEEK™ resin.

The three-way electromagnetic valve 413 switches between air and Millipore Milli-Q™ biocel ultrapure water (hereinafter called "Milli-Q™ water"), supplying them to the three-way electromagnetic valve 423 downstream. The three-way electromagnetic valve 423 switches between a buffer solution, the air and the Milli-Q™ water from the three-way electromagnetic valve 413, supplying them to the three-way electromagnetic valve 433 downstream. The three-way electromagnetic valve 433 switches between an intercalation agent, the air and the Milli-Q™ water, and the buffer solution supplied from the three-way electromagnetic valve 423, supplying them to the valve body 782 downstream. The three-way electromagnetic valve 441 switches between supplying air and solution from the valve body 781 to the nozzle 707 and supplying the three-way electromagnetic valve 445 through a bypass pipe. The three-way electromagnetic valve 445 switches between supplying the air and the solution from the three-way electromagnetic valve 441 and sending the solution and the air through the nozzle 708 from the cassette (detection chip) 21.

In order to send the buffer solution into the cassette (detection chip) 21 in the valve unit 705 shown in FIG. 6, the three-way electromagnetic valves 423, 441, and 445 and the liquid sending pump 454 are turned ON. This leads to the buffer solution being drawn up, the buffer solution being switched to the nozzle 707, then drawn from the nozzle 707 to the cassette (detection chip) 21, and from the cassette (detection chip) 21 to the nozzle 708, and discharged through the three-way electromagnetic valve 445. In order to send Milli-Q™ water into the cassette (detection chip) 21, the three-way magnetic valve 413 is turned ON rather than the three-way electromagnetic valve 423. In order to send intercalation agent into the cassette (detection chip) 21, the three-way electromagnetic valve 433 is turned ON instead of the three-way electromagnetic valve 423. In order to supply air into the cassette (detection chip) 21, the three-way electromagnetic valve 403 is turned ON, and any of the three-way electromagnetic valve 412, 423, or 433 is turned OFF. The internal volume of the pipe for the cavity portion provided in the valve body 781 of the valve unit 705 is about 100 µL, including the volume in the valve. If, unlike the present embodiment, the three-way valves are connected with a tube to implement the same flow, an internal volume of about 500 µL is required, though the sample solution volume can be greatly decreased. The internal volume between the valve unit 705 and the cassette (detection chip) 21 is greater than 100 µL in the example compared to the present embodiment, but in the present embodiment, a large reduction of 10 µL is possible. With such a configuration, after the switch to the sample solution, the volume of the sample solution or the air flowing in the cassette (detection chip) 21 contrary to intentions can be greatly decreased. As a result, fluctuation in reactions and measurements can be decreased, greatly improving the reproducibility of the results.

A solution shaking device not illustrated is provided, so the sample solution can be shaken automatically in the chip cassette. Shaking the sample solution is effective in:
(1) a hybridization process of sample DNA and probe DNA;
(2) a washing process; and
(3) an intercalation agent supply process, and the like.

Shaking the sample DNA in the hybridization process, pointed as item (1), improves the efficiency of hybridization, reducing the time therefore. Shaking buffer fluid in the washing process, pointed as item (2), improves the efficiency of stripping the non-specific adsorption DNA, thereby shortening the washing time. Also, shaking the intercalation agent in the intercalation agent supply process, pointed as item (3), improves the uniformity of intercalation agent concentration and the uniformity of intercalation agent adsorption, improving signal fluctuation and the S/N ratio. The effects of solution shaking can be obtained by applying the automatical-solution shaking process to all three processes, pointed as items (1) to (3), or to just a portion of the three processes.

As partially mentioned at the outset, the nucleotide sequence determination system according to the embodiment of the present invention embraces the measurement unit 10, the control mechanism connected to the measurement unit 10, and the computer (genotyping system) 16 connected to the control mechanism 15 as shown in FIG. 7. The measurement unit 10 encompasses the chip cartridge 11, the detecting system 12, the fluid transport system 13 and the temperature controller 14. Although the detecting system 12 is electrically connected to the chip cartridge 11 as shown in FIG. 7, the fluid transport system 13 is physically connected to the meandering flow channel provided at the chip cartridge 11 through an interface portion. After liquid solution is injected manually into the supplying vessel (container) of the nucleotide sequence determination system, the liquid solution can be conveyed automatically from the supplying vessel to the meandering flow channel provided at the chip cartridge 11 by the fluid transport system 13. The temperature controller 14 controls the temperature of the chip cartridge 11, and the like.

Figure 8:
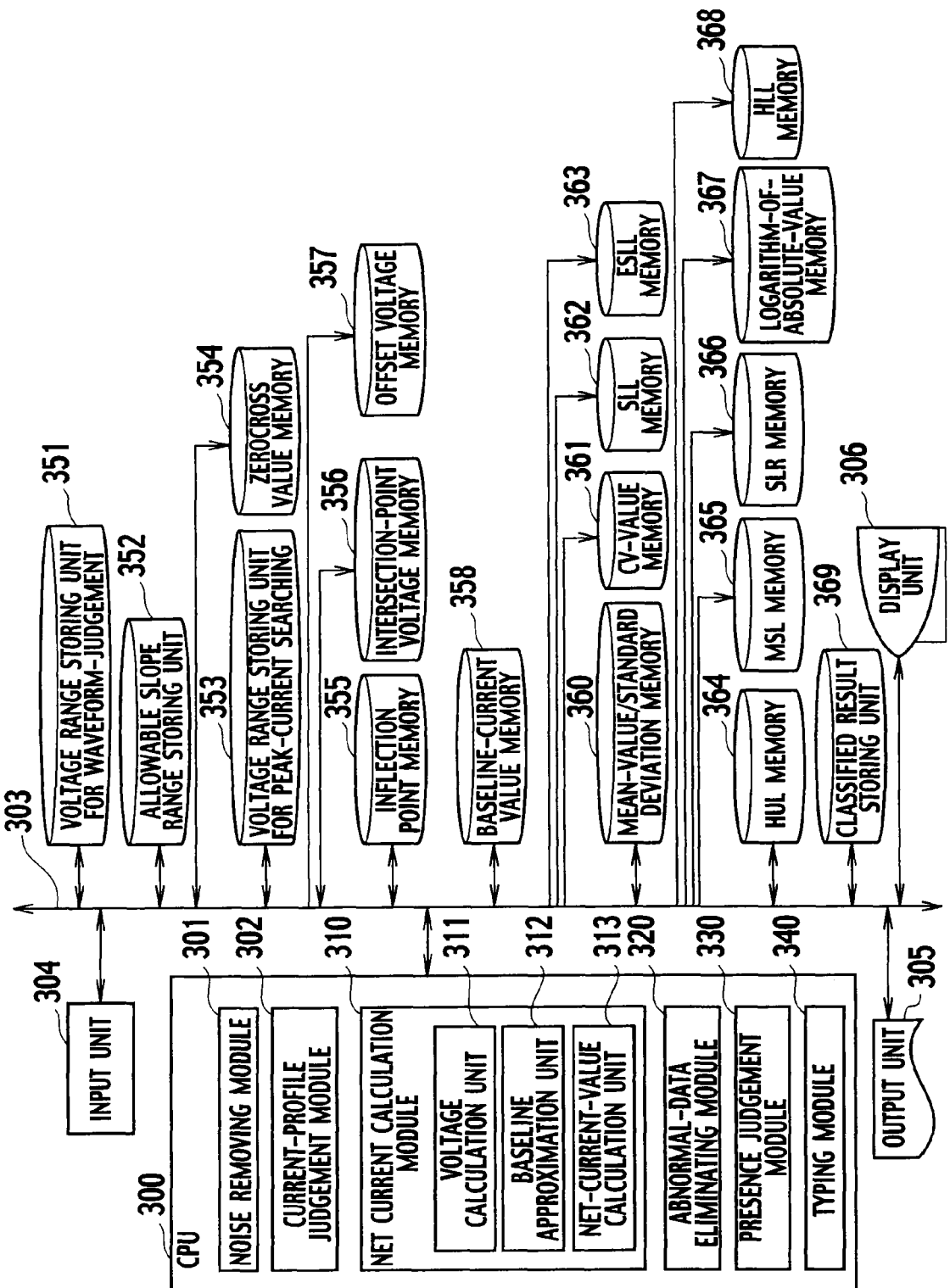
FIG. 8 is a logical block diagram explaining one example of the organization of the computer system that implements the nucleotide sequence determination system according to the embodiment of the present invention.

The computer (genotyping system) 16 shown in FIG. 7 encompasses an input unit 304 for receiving input information such as data and commands from an operator as shown in FIG. 8; a central processing unit (CPU) 300 for determining whether a target nucleic acid is present or not, which of two SNP types a nucleic acid is, whether it is a homogenous type, or whether it is a hetero-type; an output unit 305 or a display unit 306 for outputting the results of the determination; a data storage portion (illustration omitted) for storing predetermined data and the like necessary for nucleotide sequence determination; and a program storage portion (illustration omitted) for storing a nucleotide sequence determination program and the like.

The CPU 300 encompasses a noise removing module 301, a current-profile judgement module 302, a net current calculation module 310, an abnormal-data eliminating module 320, a presence judgement module 330, and a typing module 340.

Figure 15:
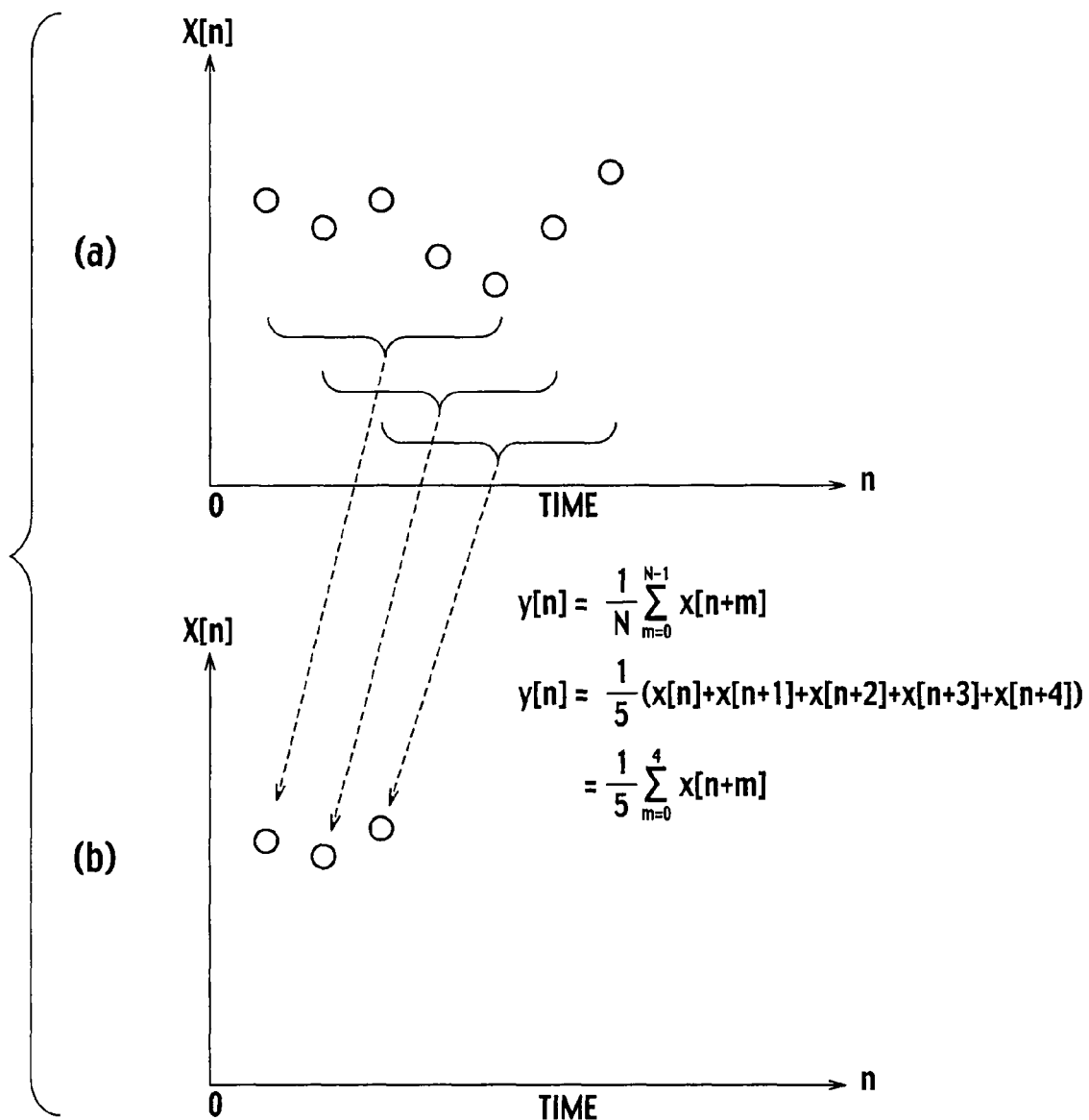
FIG. 15 is a schematic plot explaining the smoothing based on the simple moving average method.

The noise removing module 301 removes noise by smoothing the current measured through an SNP1 detecting electrode 551, an SNP2 detecting electrode 552, and a control electrode 553 shown in FIG. 2, based on a "simple moving average method." The smoothing may utilize a simple moving average method, for example, as shown in FIG. 15. Literally, the "simple moving average method" simply averages out several actual values, for example, time-series data as shown in FIG. 15 (a) focusing on its regularity. In FIG. 15, setting the interval of the moving averages to be m=5, the figure obtained by dividing the data from five points in series by five:

$$y[n]=(x[n]+x[n+1]+x[n+2]+x[n+3]+x[n+4])/5 \qquad (2)$$

becomes the moving average in FIG. 15 (b). As shown in FIG. 15 (b), the moving average smoothes the variation in FIG. 15 (a), which facilitates the analysis of a general trend.

The current-profile judgement module 302 calculates the slope of the tail line (characteristic baseline) of the current waveform (current-voltage characteristic) respectively measured by the SNP1 detecting electrode 551, the SNP2 detecting electrode 552, and the control electrode 553 shown in FIG. 2. Based on each slope of the tail line (characteristic baseline), it determines whether the respective detection signal (current waveform) is normal or abnormal, and abnormal detection signals are excluded from the calculation.

The net current calculation module 310 contains a voltage calculation unit 311, a baseline approximation unit 312, and a net-current-value calculation unit 313. According to the procedure described in a flowchart in FIG. 18A and FIG. 18B, it calculates a peak value (peak current value) of true electrochemical current (true detection signal) derived from a intercalation agent 591 by subtracting background current from the current (detection signal) measured by the SNP1 detecting electrode 551, the SNP2 detecting electrode 552, and the control electrode 553.

Figure 18A:
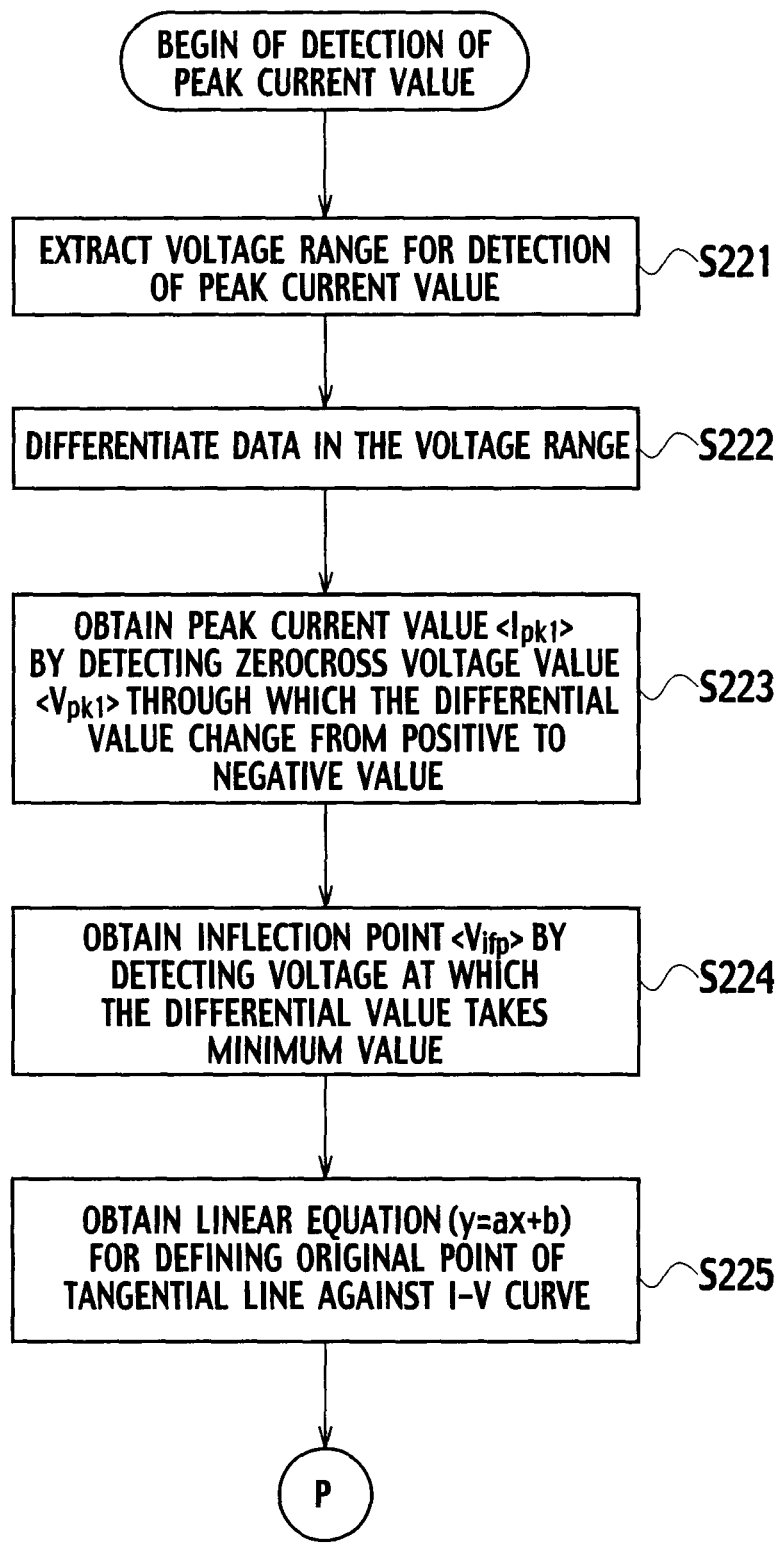
FIG. 18A is a flow chart explaining one example of the method for obtaining the net peak value (peak current value) of the detected signal from the wave forms of electro-chemical currents (current-voltage characteristics) measured by each electrode respectively, subtracting the background current in each case, in the nucleotide sequence determination method according to the embodiment of the present invention.
Figure 19:
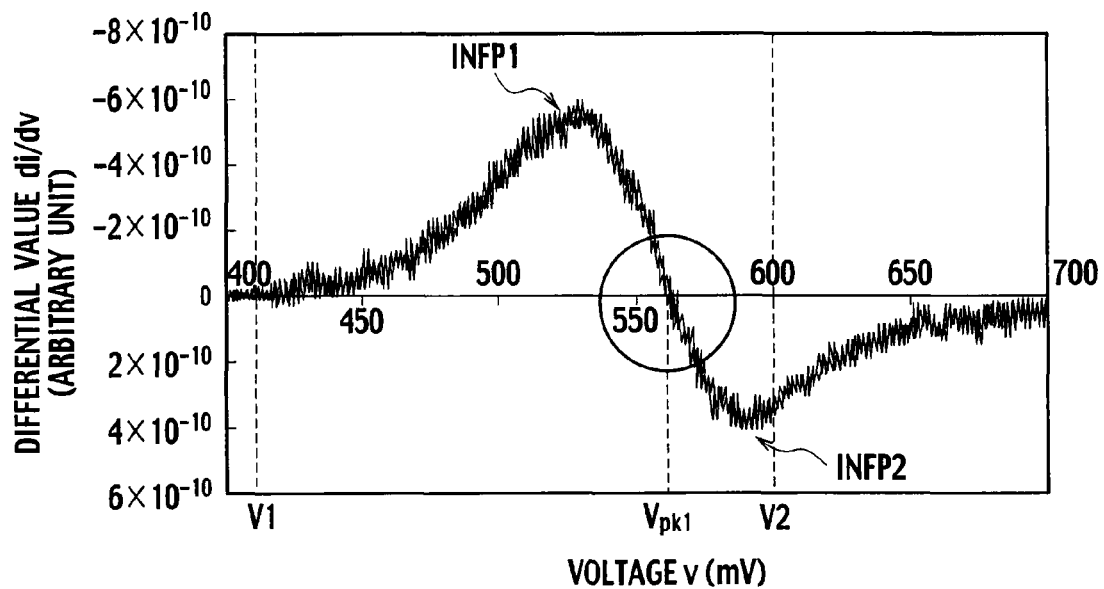
FIG. 19 is a schematic plot explaining the method for obtaining a "zero-cross" point by using the differential curve (di/dv) of the electro-chemical current, the "zero-cross" point serves as a point where the background current is subtracted from the wave form of electro-chemical current (current-voltage characteristic) measured by each electrode respectively, in the nucleotide sequence determination method according to the embodiment of the present invention.

The voltage calculation unit 311, according to procedure described in steps S221-S223 of FIG. 18A, differentiates the electrochemical current (i), which represents a waveform of the current (i)-voltage (v) characteristic measured by the chip cartridge 11, with respect to the voltage value (v). Then, in a range between a predetermined lower limit value V1 and upper limit value V2, the voltage calculation unit 311 determines the voltage value $V_{pk1}$ and the current value $I_{pk1}$ at the point where the differential curve (di/dv) "zero-crosses" with respect to each of the current-voltage characteristics measured by the plurality of electrode units 761 respectively (see FIG. 19). The point of "zero-cross" refers to a point in which the differential curve (di/dv) of the electrochemical current varies from positive to negative or from negative to positive, which corresponds to the voltage value $V_{pk1}$ and the current value $I_{pk1}$ that give a current peak. FIG. 19 shows a variation of the differential value (di/dv) varies with the voltage values, indicating the voltage value $V_{pk1}$ and the current value $I_{pk1}$ at the point where the differential value (di/dv) varies from negative to positive as the voltage value increases. When there is an odd number of "zero-cross values", the center value is adopted as the voltage value $V_{pk1}$. When there is an even number of "zero-cross values", the most approximate value to the center value is adopted as the voltage value $V_{pk1}$.

Figure 18B:
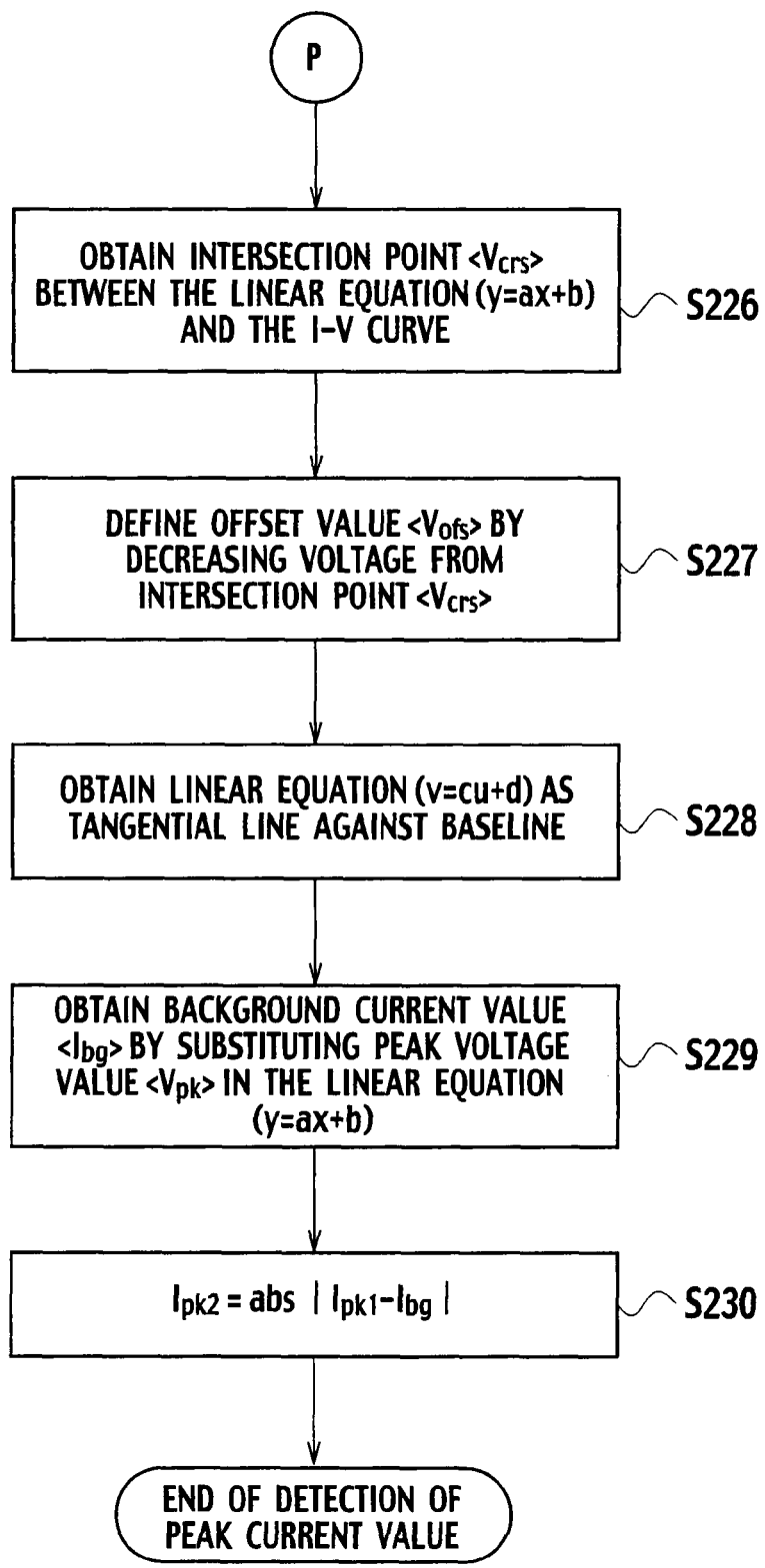
FIG. 18B is a flow chart to explain the procedure in the method for obtaining the net peak value (peak current value) of the detected signal from the wave forms of electro-chemical current (current-voltage characteristic) measured by each electrode respectively, following to the procedure shown in the flow chart in FIG. 18A.
Figure 20:
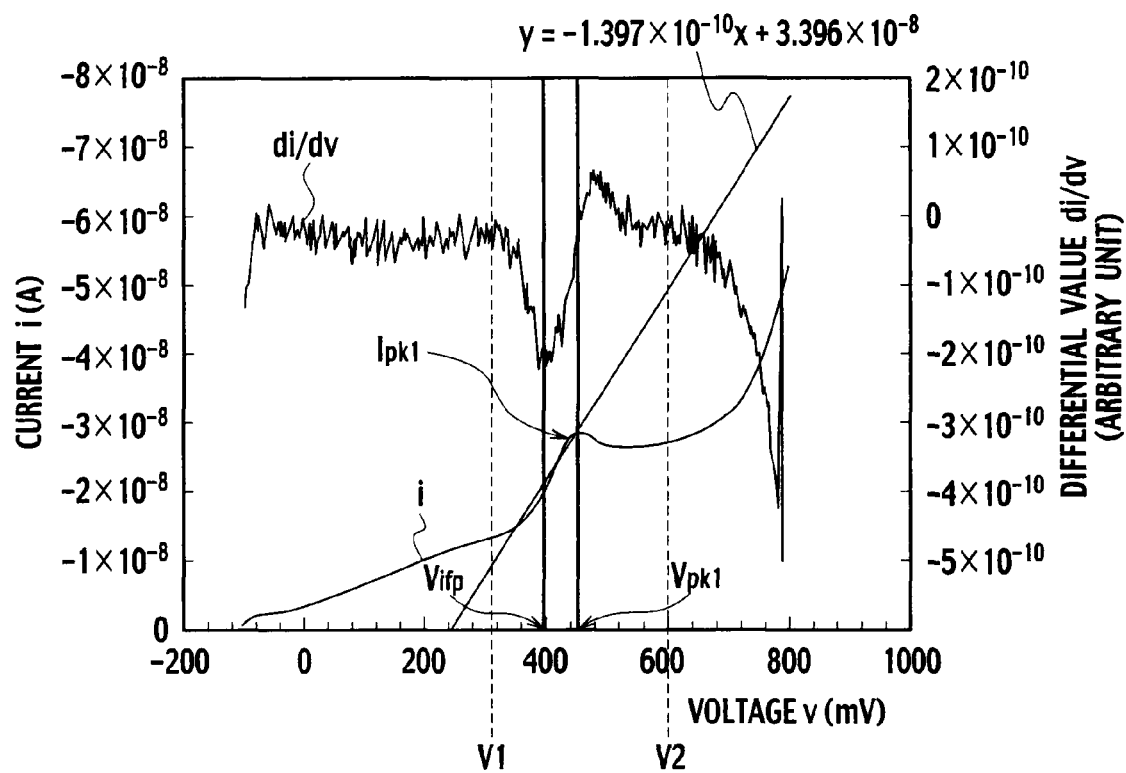
FIG. 20 is a schematic plot explaining the method for approximating a straight line to the curved line of the current-voltage characteristic, the approximated straight line is employed in a sequence of calculation steps, which subtracts the background current from the wave forms of electro-chemical current (current-voltage characteristic) measured by each electrode respectively, in the nucleotide sequence determination method according to the embodiment of the present invention.
Figure 21:
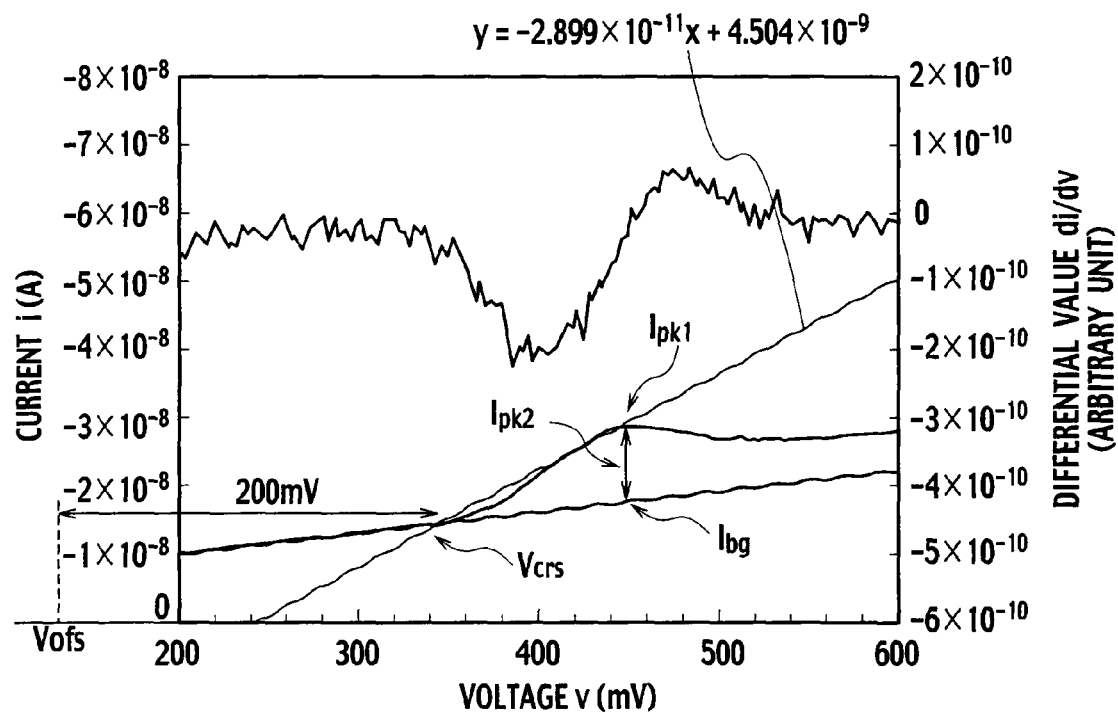
FIG. 21 is an enlarged view of FIG. 20.

The baseline approximation unit 312, according to the procedure described in step S224 of FIG. 18A to step S228 of FIG. 18B, approximates each of the baselines (backgrounds) of the plurality of current-voltage characteristics, which represent the plurality of electrochemical currents measured by the plurality of electrode units 761 (see FIG. 20 and FIG. 21). The net-current-value calculation unit 313, according to steps S229 and S230 described in FIG. 18B, calculates each of the true peak current values $I_{pk2}$ on the plurality of current-voltage characteristic-curved-lines representing the electrochemical current by subtracting the corresponding background (baseline) current value $I_{bg}$ calculated by the baseline approximation unit 312 from the corresponding zero-cross current values $I_{pk1}$ calculated by the voltage calculation unit 311.

Figure 24:
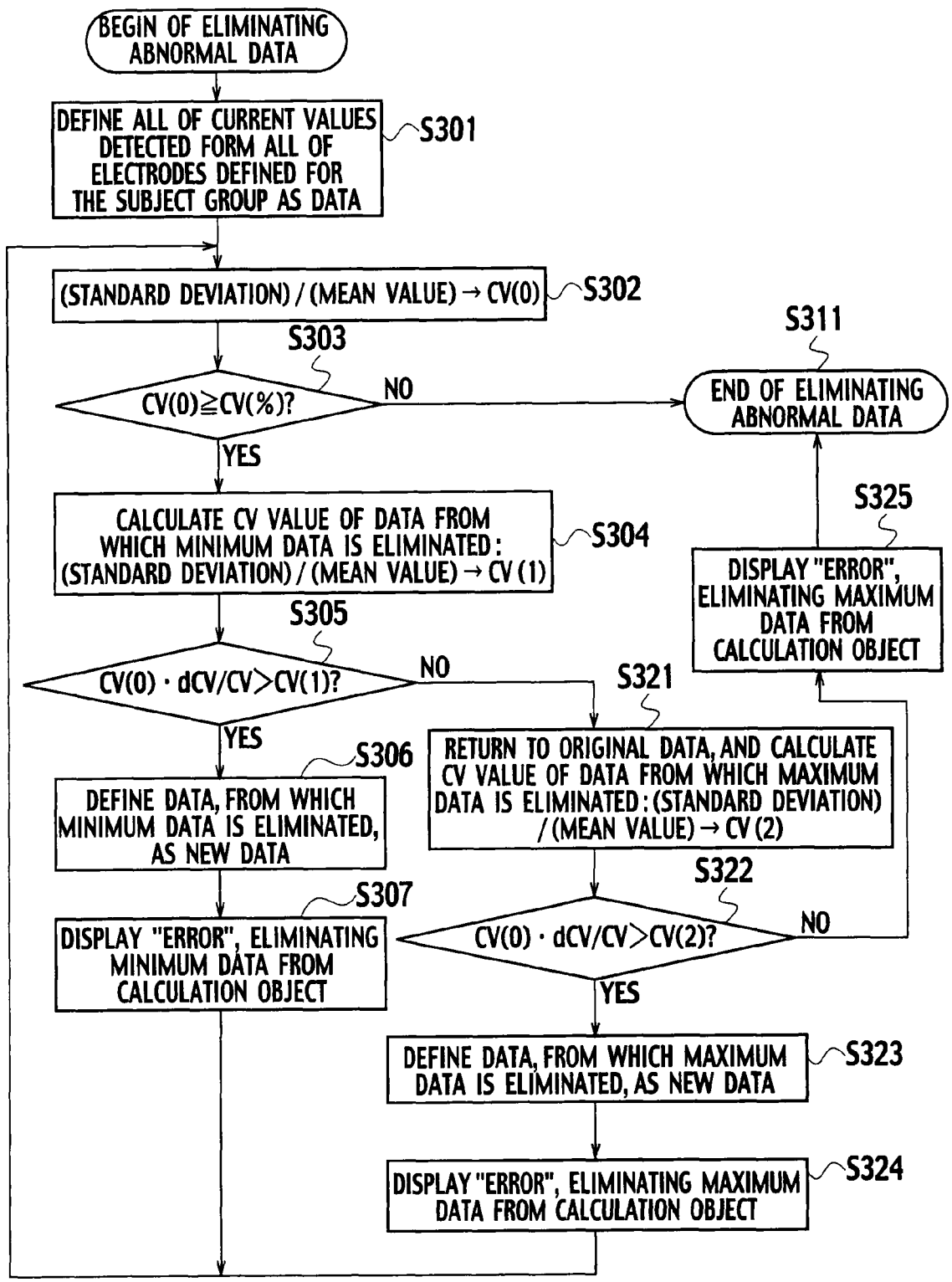
FIG. 24 is a flow chart explaining one example of the method for excluding abnormal data from the peak current value of the calculated data from each electrode respectively, in the nucleotide sequence determination method according to the embodiment of the present invention.

The abnormal-data eliminating module 320, according to a sequence of process-steps shown in a flowchart in FIG. 24, eliminates abnormal data from a data group of peak values (peak current values) of the true electrochemical currents (true detection signals) calculated by the net current calculation module 310. Briefly, the abnormal-data eliminating module 320 eliminates a group of data that do not meet a certain standard, assigning as an abnormal value data group, from a plurality of current value $I_{pk2}$ data groups obtained from the plurality of SNP1 detecting electrodes 551, the plurality of SNP2 detecting electrodes 552, and the plurality of control electrodes 553, respectively, that are contained in the plurality of electrode units 761 arranged on the substrate 714 as shown in FIG. 4.

Figure 25A:
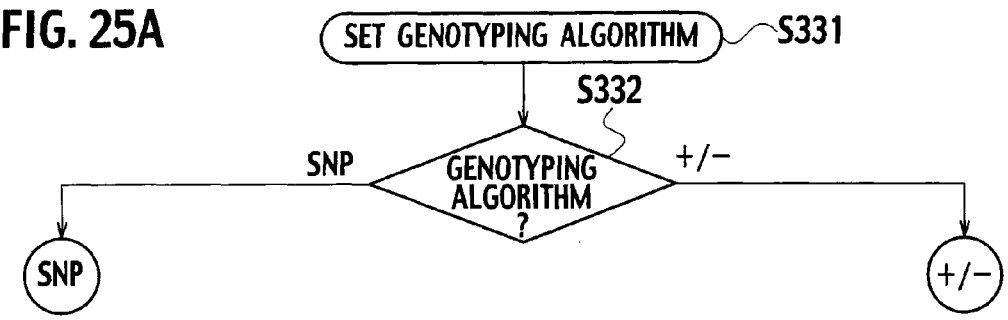
FIG. 25A is a flow chart explaining the method for deciding whether to proceed to a first algorithm determining whether a certain nucleic acid is present or not, or to proceed to a second algorithm determining, from the two types, which one is present, the hetero-type or the homo-type, in the nucleotide sequence determination method according to the embodiment of the present invention.
Figure 25B:
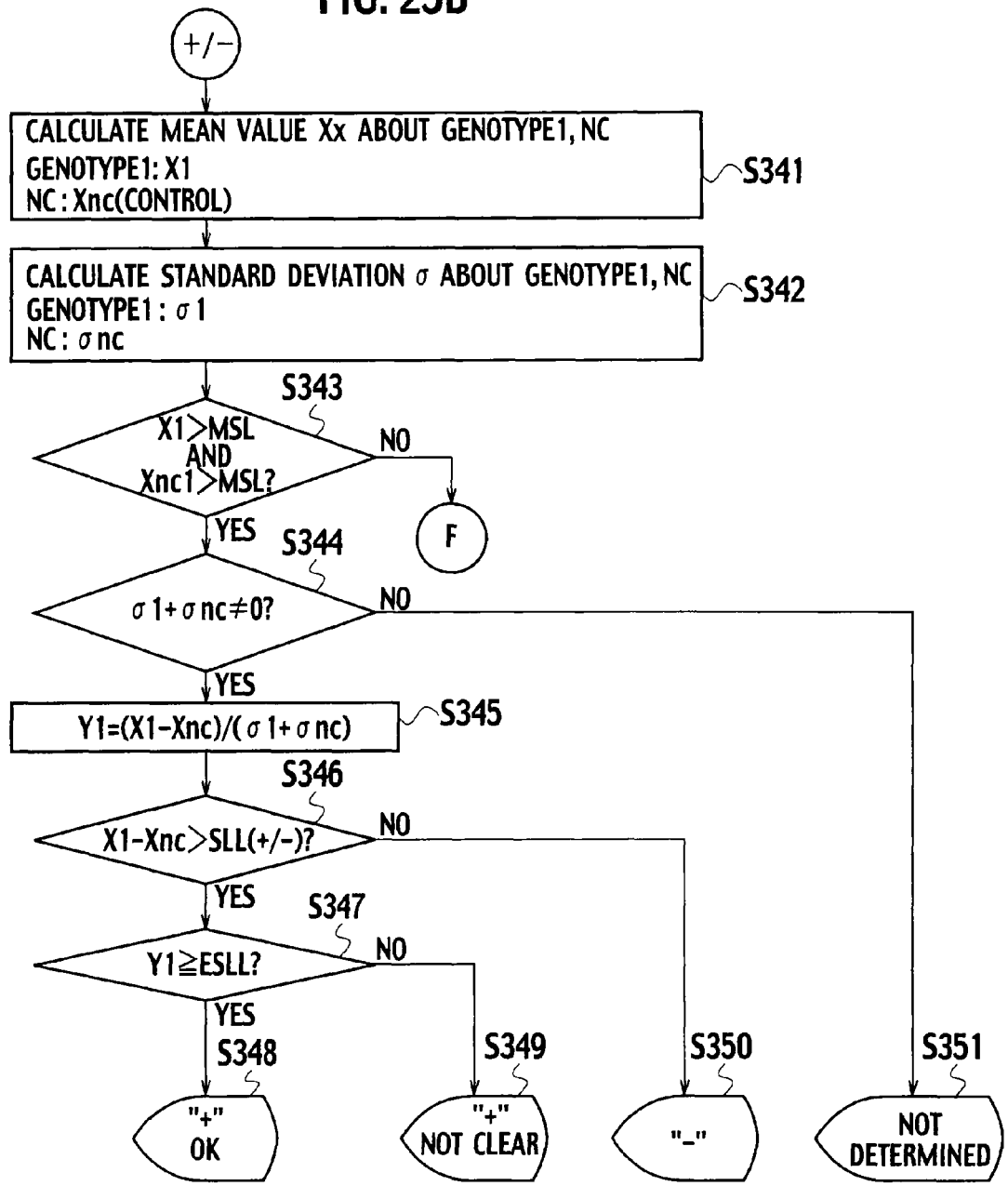
FIG. 25B is a flow chart explaining one example of the algorithm for determining whether or not a certain nucleic acid is present, in the nucleotide sequence determination method according to the embodiment of the present invention.

The presence judgement module 330, according to a sequence of process-steps shown in a flowchart in FIG. 25B, determines whether or not the subject nucleic acid is present.

Figure 25D:
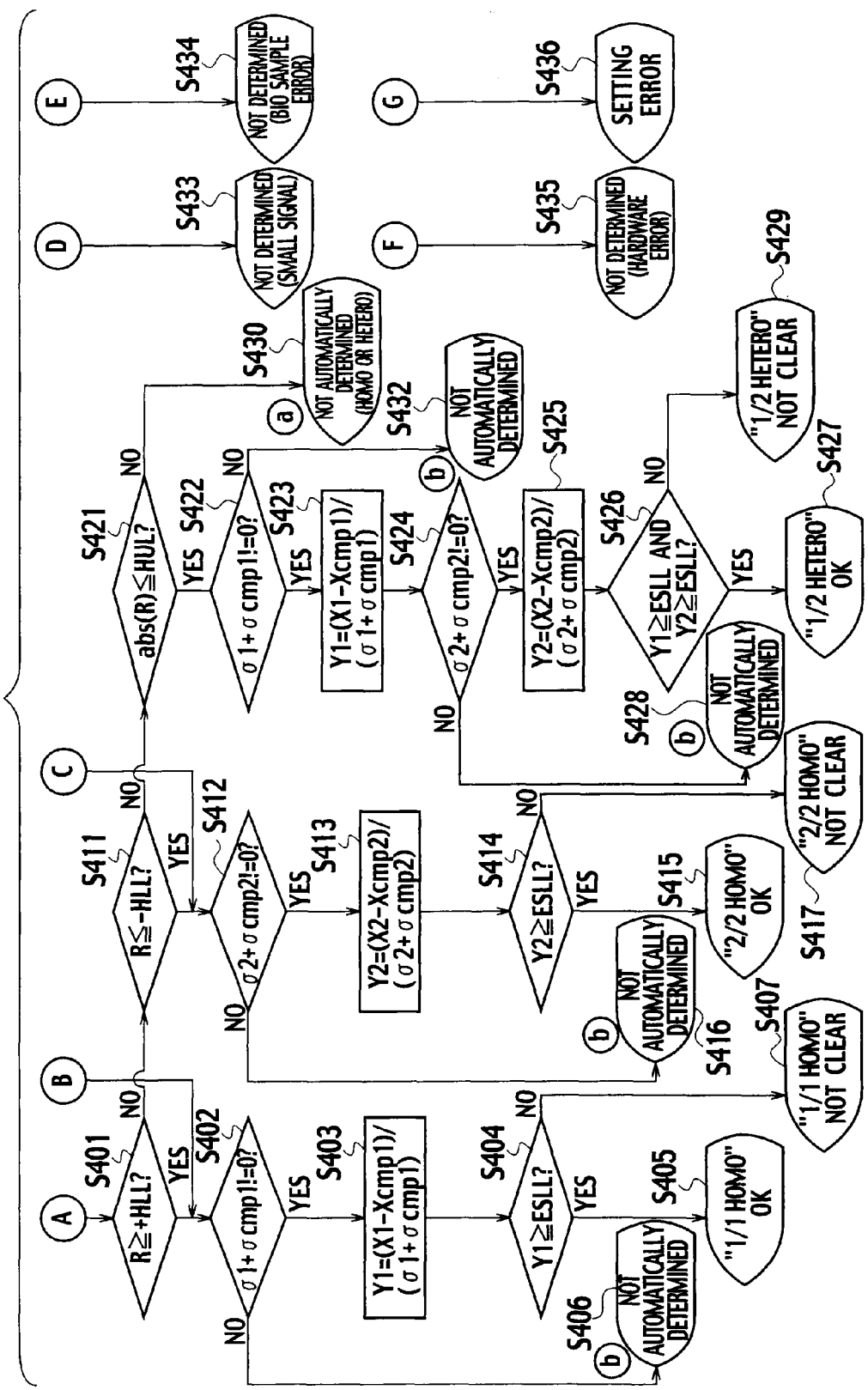
FIG. 25D is a flow chart succeeding to FIG. 25C, explaining the example of the algorithm for determining which of the two kinds of SNP type, the SNP="G" or the SNP="T", is present, or whether the SNP type is the homo-type or the hetero-type, in the nucleotide sequence determination method according to the embodiment of the present invention.

The typing module 340, according to a sequence of process-steps shown in a flowchart in FIG. 25C and FIG. 25D, determines the SNP type as SNP="G" or SNP="T". Furthermore, the typing module 340 classifies the SNP types into a G/G homo-type, a G/T hetero-type, or a T/T homo-type, and the like.

To the CPU 300, a voltage range storing unit (for waveform-judgement) 351, a allowable slope range storing unit 352, a voltage range storing unit (for peak-current searching) 353, a zero-cross value memory 354, a inflection point memory 355, a intersection-point voltage memory 356, a offset voltage memory 357, a baseline-current value memory 358, a mean-value/standard deviation memory 360, a coefficient of variance (CV) value memory 361, a signal lower limit (SLL) memory 362, an effective signal lower limit (ESLL) memory 363, a hetero-type upper limit (HUL) memory 364, a minimum signal level (MSL) memory 365, a signal lower ratio (SLR) memory 366, a logarithm-of-absolute-value memory 367, a homo-type lower limit (HLL) memory 368, and a classified result storing unit 36 are connected via a bus 303.

The voltage range storing unit (for waveform-judgement) 351 stores "lower limit voltage VLo" and "higher limit voltage VHi (VLo<VHi)" as a range of calculating the slopes of the tail lines (characteristic baselines) of the currents (detection signals) measured by the plurality of SNP1 detecting electrode 551, the plurality of SNP2 detecting electrode 552, and the plurality of control electrode 553, respectively. The allowable slope range storing unit 352 stores "lower limit slope value (Coef Lo)" and "higher limit slope value (Coef Hi)" as parameters for the current-profile judgement module 302 to determine allowable values of the slopes of the tail lines (characteristic baselines) of the detection signals.

The voltage range storing unit (for peak-current searching) 353 stores a predetermined peak-current-searching voltage range [V1, V2] as a predetermined parameter, which facilitates the voltage calculation unit 311 to read out the peak-current-searching voltage range [V1, V2]. The position of the current peak indicated by the current-voltage characteristic of the electrochemical current will appear within a substantially constant voltage range if the measurement conditions are fixed. Therefore, the peak-current-searching voltage range [V1, V2] is determined as the predetermined parameter. The zero-cross value memory 354 sorts and stores the "zero-cross values (zero-cross voltage values $V_{pk1}$, zero-cross current values $I_{pk1}$)" in each of all electrode units 761 on the substrate 714 shown in FIG. 4.

The inflection point memory 355 stores the inflection point voltage $V_{ifp}$ required for calculation by the baseline approximation unit 312. The "inflection point voltage $V_{ifp}$", as shown in FIG. 20, is the voltage at which the differential curve is minimized by tracing the voltage, in a negative direction (by decreasing the voltage), from the zero-cross voltage value $V_{pk1}$ that gives the current peak. The intersection-point voltage memory 356 stores the intersection-point voltage $V_{crs}$. The "intersection-point voltage $V_{crs}$", as shown in FIG. 21, is the voltage given by the intersection-point with the approximate linear expressions of the current-voltage characteristic curve of the electrochemical current and this current-voltage characteristic curve. The offset voltage memory 357, as shown in FIG. 21, stores the offset voltage $V_{ofs}$ obtained by tracing the voltage starting from the intersection-point voltage value $V_{crs}$ as much as the offset value defined as a predetermined parameter in a negative direction (by decreasing the voltage).

The baseline-current value memory 358 stores a plurality of baseline (background) current values $I_{bg}$ required for calculation by the net-current-value calculation unit 313. Each of the "baseline (background) current values $I_{bg}$", as shown in FIG. 21, is the current value serving as background, which can be obtained by substituting the zero-cross voltage value $V_{pk1}$ calculated by the voltage calculation unit 311 into the approximate linear expression of the baseline calculated by the baseline approximation unit 312.

The mean-value/standard deviation memory 360 stores the mean current values $X_1$ obtained from measurement by the plurality of SNP1 detecting electrodes 551, the mean current values $X_{nc1}$ obtained from measurement by the plurality of control electrodes (NC1) corresponding to the SNP1 detecting electrodes 551, the mean current values $X_2$ obtained from measurement by the plurality of SNP2 detecting electrodes 552, the mean current values $X_{nc2}$ obtained from measurement by the plurality of control (NC2) electrodes corresponding to the SNP2 detecting electrodes 552, the standard deviations $\sigma_1$ of the peak current values obtained from measurement by the plurality of SNP1 detecting electrodes 551, the standard deviations $\sigma_{nc}$, $\sigma_{nc1}$, or $\sigma_{cmp1}$ of the peak current values obtained from measurement by the plurality of corresponding control electrodes 553, the standard deviations $\sigma_2$ of the peak current values obtained from measurement by the plurality of SNP2 detecting electrodes 552, the standard deviations $\sigma_{nc}$, $\sigma_{nc2}$, or $\sigma_{cmp2}$ of the peak current values obtained from measurement by the plurality of corresponding control electrodes 553 and further the differences in the mean-values $(X_1-X_{nc})$, $(X_1-X_{nc1})$, $(X_2-X_{nc2})$, the sums of the standard deviations $(\sigma_1+\sigma_{nc})$, $(\sigma_1+\sigma_{nc1})$, $(\sigma_1+\sigma_{cmp1})$, $(\sigma_2+\sigma_{cmp2})$, the ratios of the differences in the mean-values to the sums of the standard deviations $(X_1-X_{nc})/(\sigma_1+\sigma_{nc})$, and the like that are calculated by the abnormal-data eliminating module 320, the presence judgement module 330, and the typing module 340 respectively. These mean-values $X_1$, $X_{nc1}$, $X_2$, $X_{nc2}$, and the standard deviations $\sigma_1$, $\sigma_{nc}$, $\sigma_{nc1}$, $\sigma_{cmp1}$, $\sigma_2$, $\sigma_{nc2}$, $\sigma_{cmp2}$, and the like are read out, as needed by each of requirements of the corresponding calculations, from the abnormal-data eliminating module 320, the presence judgement module 330, and the typing module 340.

Figure 26:
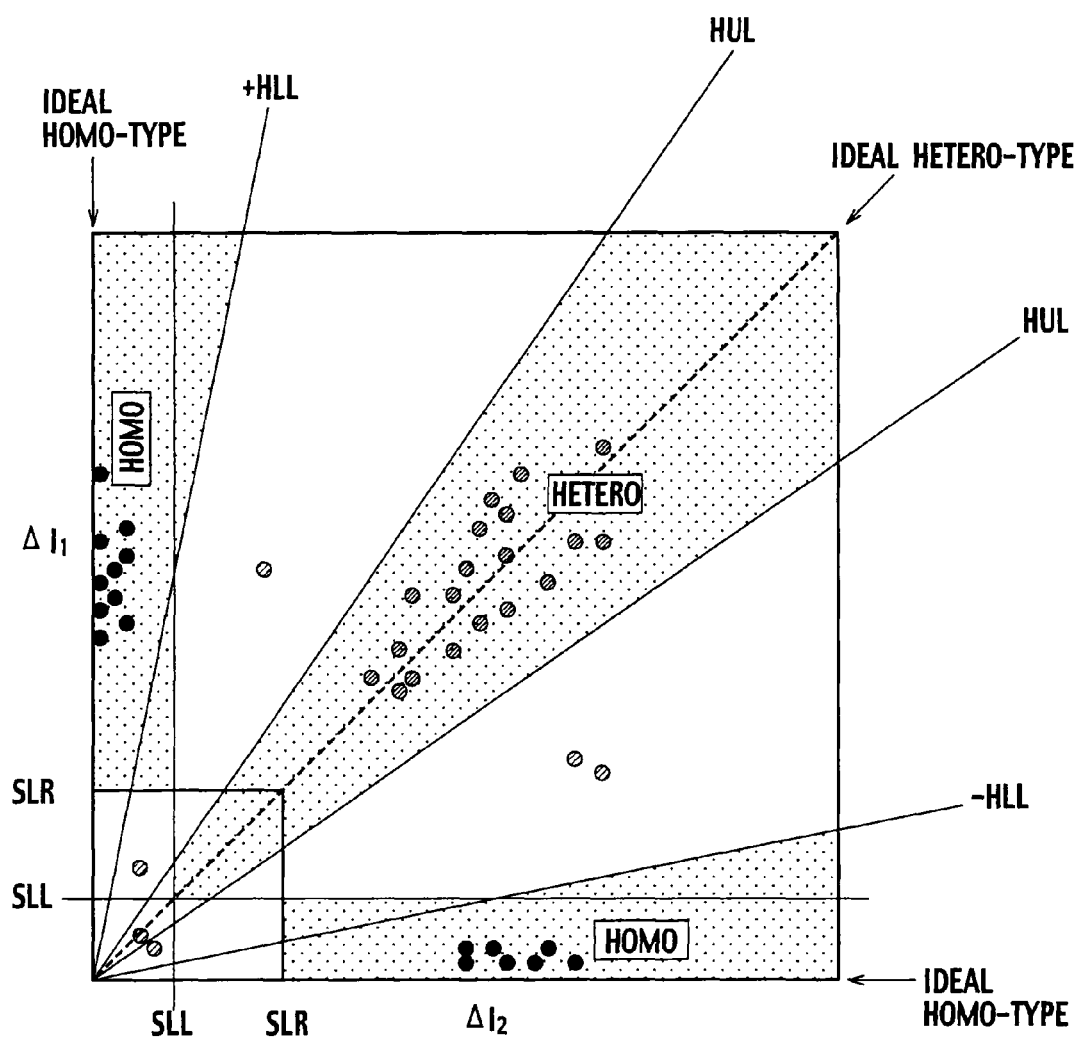
FIG. 26 is a concept image view showing the various parameters that establish the basis of the determining procedure in the nucleotide sequence determination method according to the embodiment of the present invention.

The CV-value memory 361 stores various coefficient of variance (CV) values calculated by the abnormal-data eliminating module 320, such as CV (0), CV (1), CV (2), and also standard CV values CV (%) or CV value correction coefficients dCV/CV required for calculation by the abnormal-data eliminating module 320. The "CV value" refers to the value obtained by multiplying the resulting value of dividing the standard deviation of the subject set of data by the corresponding mean-value by 100 and is indicated as a percentage. Since the dispersion or variance has a unit of a sample, the degree of variation for the two sample groups cannot be compared. Therefore, the value was divided by the respective mean-value to give an absolute number. The SLL memory 362 stores the signal-increment criterion SLL (+/−) required for the calculation by the presence judgement module 330 and the signal-increment criterion SLL (M) required for the calculation by the typing module 340. The signal-increment criterion SLL is a predetermined parameter that provides selection criterion (criterion) for the determination algorithm of the signal increase to the control electrode 553. FIG. 26 shows the concept image indicating various parameters as criterion. The ordinate refers to the difference $(X_1-X_{nc1})$ between the mean current value $X_1$ of the SNP1 detecting electrode 551 and the mean current value of the control electrode (NC1) 553 corresponding to the SNP1 detecting electrode 551, which indicates the signal increase at the SNP1 detecting electrode 551 side. The abscissa refers to the difference $(X_2-X_{nc2})$ between the mean current value $X_2$ of the SNP2 detecting electrode 552 and the mean current value of the control electrode (NC2) 553 corresponding to the SNP2 detecting electrode 552, which indicates the signal increase at the SNP2 detecting electrode 552 side. The signal-increment criterion SLL is indicated by two lines running at right angles to each other in the area relatively close to the original point. The ESLL memory 363 stores the effective variance coefficient ESLL required for the calculation by the presence judgement module 330 and the typing module 340. The effective variance coefficient ESLL is a predetermined parameter that provides the lower limit of determination regarding how many folds the signal increase is, in comparison with the standard deviation σ.

The HUL memory 364 stores the hetero-typing criterion HUL with respect to the logarithm signal ratio required for the calculation by the typing module 340. The hetero-typing criterion HUL with respect to the logarithm signal ratio is a predetermined parameter that provides the upper limit of the signal ratio determination in the case of hetero-types, and ideally:

$$\mathrm{abs}((X_1-X_{nc1})/(X_2-X_{nc2})) = 1,$$

that is, $\mathrm{Log}_{10}(1)=0$. The concept image view of FIG. 26, indicating various parameters as criterion, shows a hetero-type in which a diagonal ideally passes through the original point. Two hetero-typing criterion HUL with respect to the logarithm signal ratio are shown as lines to determine the area on both sides of the diagonal. The MSL memory 365 stores a predetermined parameter MSL required for the calculation by the presence judgement module 330 and the typing module 340. The parameter MSL refers to a minimum signal amount used for the determination in the case of no current signal increase (or lacking data), and also a standard current value for determining a device (hardware) deficiency. The parameter MSL, as shown by a dashed line in FIGS. 23A-23C and FIGS. 23D-23F, is to be set as a relatively small value, for example a current value within a range of 0-100 nA. The parameter MSL is preliminary determined and stored in the MSL memory 365. The SLR memory 366 stores the magnification (scale factor) SLR of the purposive criterion that is required for calculation by the typing module 340. The purposive scale-factor SLR is a predetermined parameter that provides a lower limit of purposive determination when one type of current signal increase is low. In a concept image view of FIG. 26 indicating various parameters as criterion, the purposive scale-factor SLR is shown as two lines intersecting at right angles to each other to conceptually determine a small rectangle near the original point.

The absolute logarithm memory 367 stores "an R-value", which is $\mathrm{Log}_{10}$ of an absolute value of a ratio of the difference in the mean-values measured by the SNP1 detecting electrode 551 side required for calculating the typing module 340 to the difference in the mean-values measured by the SNP2 detecting electrode 552 side, as represented by Eq. (8). The HLL memory 368 stores the criterion (+HLL, −HLL) with respect to logarithm of signal ratio required for calculating the typing module 340. The criterion HLL with respect to logarithm of signal ratio is a predetermined parameter that provides the lower limit of signal ratio determination in the case of a homo-type. In a concept image view of FIG. 26 indicating various parameters as criterion, the criterion HLL with respect to logarithm of signal ratio is shown as two lines extending from the original point that determine the area near the abscissa and ordinate corresponding to the ideal homo-type.

The classified result storing unit 369 stores various classification results classified by the presence judgement module 330 and the typing module 340.

Figure 17:
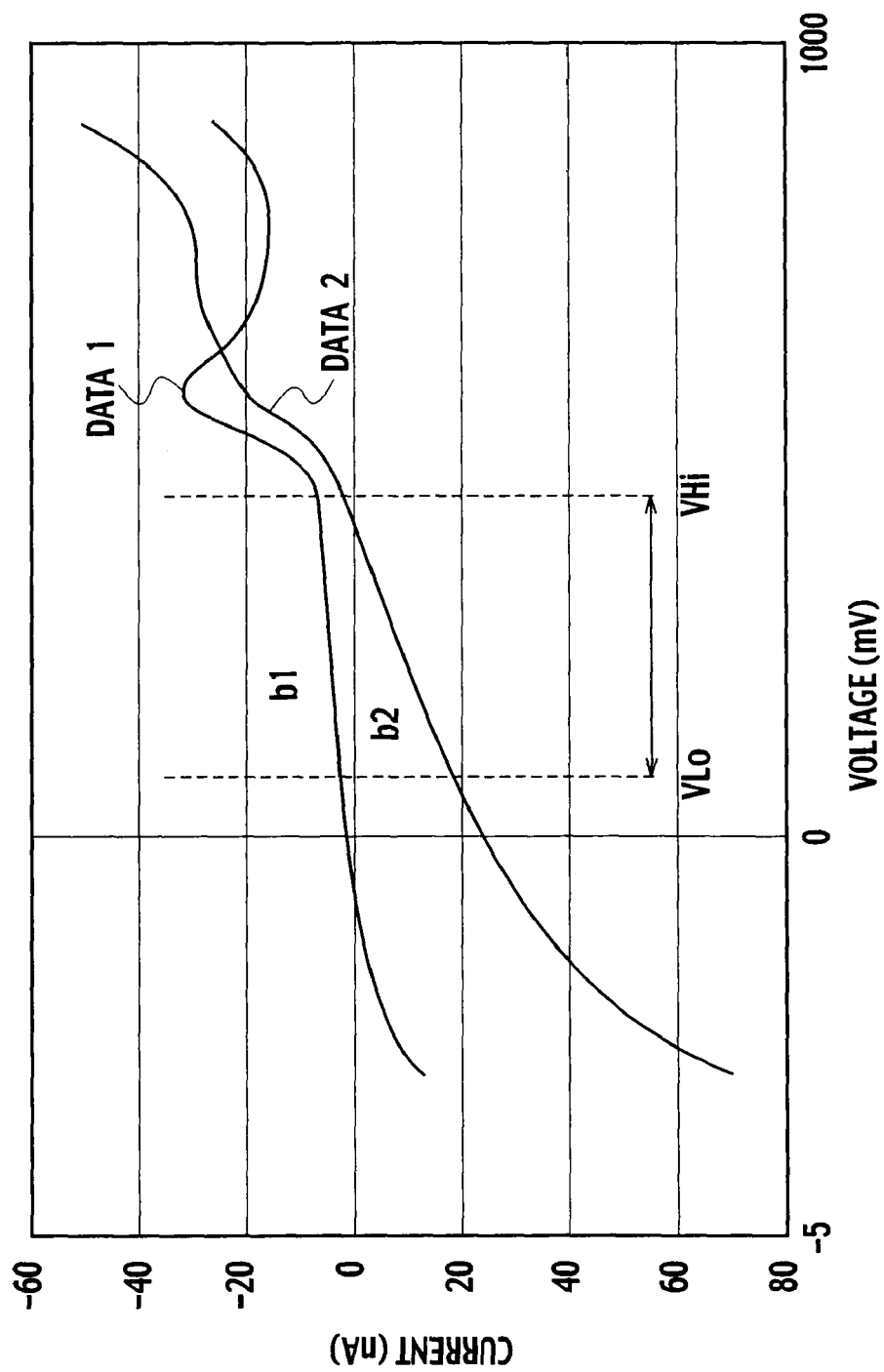
FIG. 17 shows two examples of the electro-chemical currents measured in the chip cartridge, and the slope of the tail line (characteristic baseline) of the current-voltage characteristic labeled with data 2 is larger than the slope of the tail line of the current-voltage characteristic labeled with data 1.

Although the illustration is omitted, an interface is connected to the CPU 300 via the bus 303, and it is possible to send/receive data with the control mechanism 15 shown in FIG. 17 through the local bus (not shown) via the interface.

In FIG. 8, a keyboard, mouse, light pen, or flexible disk drive, and the like may implement the input unit 304. Using the input unit 304, an operator performing nucleotide sequence determination can designate the input/output data and determine a plurality of required predetermined parameters, allowable error value, and error level. Furthermore, using the input unit 304, it is possible to determine a form of the output, and the like and to receive instructions for conducting or canceling calculations. The output unit 305 and the display unit 306 may be implemented by, for example, a printer unit and a display unit, and the like. The display unit 306 displays such items as input/output data, determination results, and determination parameters. The data memory (not shown) stores items such as input/output data, determination parameters and history of the determination parameters, and data in calculations.

As explained above, the nucleotide sequence determination system according to the embodiment of the present invention facilitates determination of the presence of nucleic acid and classification of homo/hetero-types of SNP with a high degree of accuracy in line with actual conditions.

Nucleotide Sequence Determination Method

Figure 13:
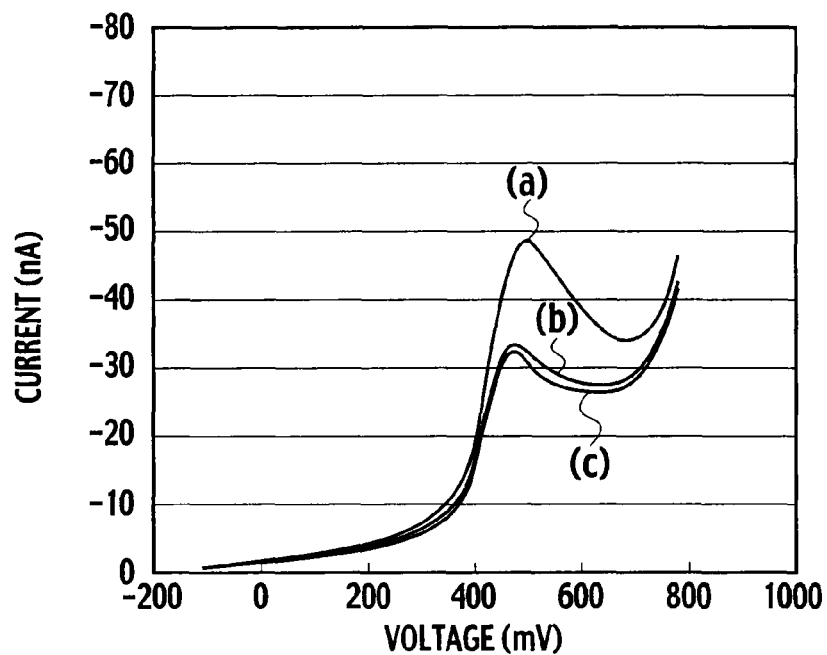
FIG. 13 shows three electro-chemical current vs. voltage characteristics, in which a curved line labeled with (a) corresponding to FIG. 12A shows that in the case that probe DNA immobilized to the SNP1 detecting electrode and the sample DNA of SNP="G" are formed into a double-strand and that the intercalation agent has intercalated, the electro-chemical current vs. voltage characteristic has a special behavior showing a large current value peak; a curved line labeled with (b) corresponding to FIG. 12B shows that in the case probe DNA immobilized to the SNP2 detecting electrode and the sample DNA of SNP="G" are unable to form a double-strand and the intercalation agent has not intercalated, the electro-chemical current vs. voltage characteristic has a special behavior showing a smaller current peak than that of the curved line labeled with (a); and a curved line labeled with (c) corresponding to FIG. 12C shows that in the case that negative DNA immobilized to the control electrode and the sample DNA of SNP="G" are unable to form a double-strand and the intercalation agent has not intercalated, the electro-chemical current vs. voltage characteristic has a special behavior showing an even smaller current peak that that of the curved line labeled with (b)

Referring to a flowchart shown in FIG. 14, the nucleotide sequence determination method according to the embodiment of the present invention will be explained. The nucleotide sequence determination method described below is one example. Including modifications, various other nucleotide sequence determination methods are of course feasible. Whatever the case, it is basic to obtain the current-voltage characteristic of electrochemical current as shown in FIG. 13 by using the detecting system 12 through the electrochemical reaction by inducing a hybridization reaction by injecting chemicals (sample solution) containing samples DNA 581, 582, 583 into the chip cartridge 11 where probe DNAs 571, 572, 573 shown in FIG. 3 are fixed, washing with the buffer solution, and introducing intercalation agents. From the current-voltage characteristic of electrochemical current, a peak current value that quantitatively corresponds to the hybridization reaction of each probe DNAs 571, 572, 573 is determined. Then, the calculated peak current value data is statistically processed, and thereby the presence of nucleic acid or the type of single nucleotide polymorphisms of nucleic acid is determined.

Prior to the explanation of the flowchart shown in FIG. 14, referring to FIGS. 9A-9C, FIGS. 10A-10C, and FIGS. 11A-11C, the hybridization of probe DNA and sample DNA will be explained. The chip cartridge 11 shown in FIG. 4 and FIG. 5 may be used for the hybridization process.

Figure 9A:
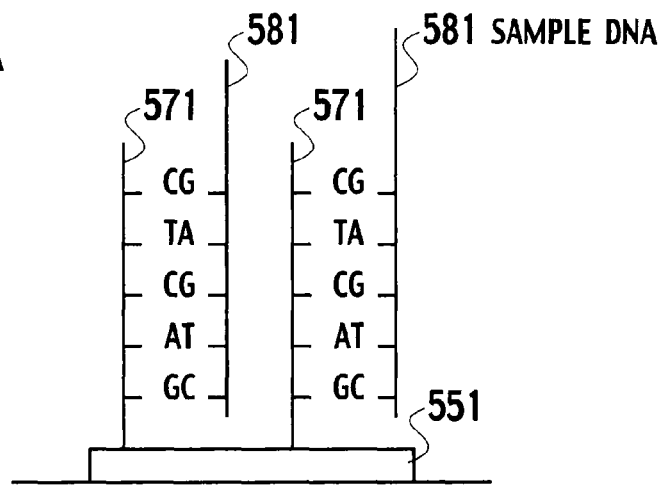
FIG. 9A is a schematic plot depicting two strands of probe DNAs, immobilized to the top surface of the SNP="G" detecting electrode, and two strands of sample DNA with SNP="G", which are paired into double-strands with the probe DNAs, because the nucleotide sequences match perfectly with the probe DNAs.
Figure 9B:
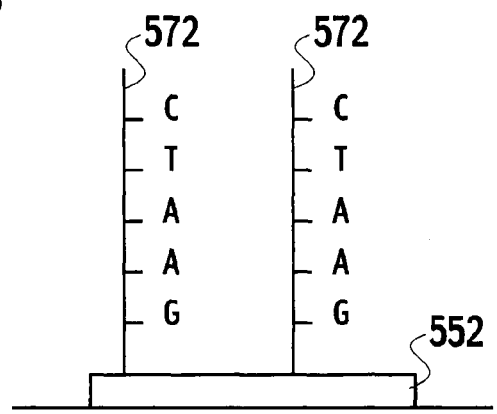
FIG. 9B is a schematic plot depicting two strands of probe DNA immobilized to the top surface of the SNP="T" detecting electrode, showing that sample DNA with SNP="G" is unable to form a double-strand with probe DNAs.
Figure 9C:
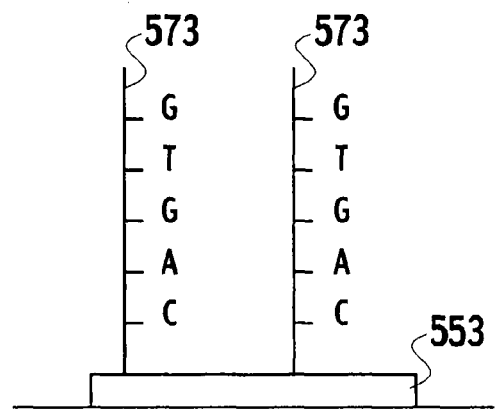
FIG. 9C is a schematic plot depicting two strands of probe DNA (negative control DNA) immobilized to the top surface of the control electrode, showing that sample DNA with SNP="G" is unable to form a double-strand with probe DNAs.

FIGS. 9A-9C show three cases in which the sample DNA 581 is assigned as a target nucleotide sequence having a nucleotide sequence CTGAG . . . (sample DNA with SNP="G"). As shown in FIG. 9A, the active electrode (SNP1 detecting electrode) 551 at which the probe DNA 571 having a nucleotide sequence GACTC . . . is fixed forms a double-strand with the target nucleotide sequence (sample DNA with SNP="G") 581, since their sequences completely match. However, if the sequence contains even one different base, a double-strand cannot be formed. Accordingly, as shown in FIG. 9B, the active electrode (SNP2 detecting electrode) 552 at which the probe DNA 572 having a nucleotide sequence GAATC . . . is fixed cannot form a double-strand with the target nucleotide sequence (sample DNA with SNP="G") 581. If the sequence is completely different, it naturally cannot form a double-strand. Therefore, as shown in FIG. 9C, the active electrode (control electrode) 553 at which the probe DNA (negative control DNA) 573 having a nucleotide sequence CAGTG . . . is fixed cannot form a double-strand with the target nucleotide sequence (sample DNA with SNP="G").

Figure 10C:
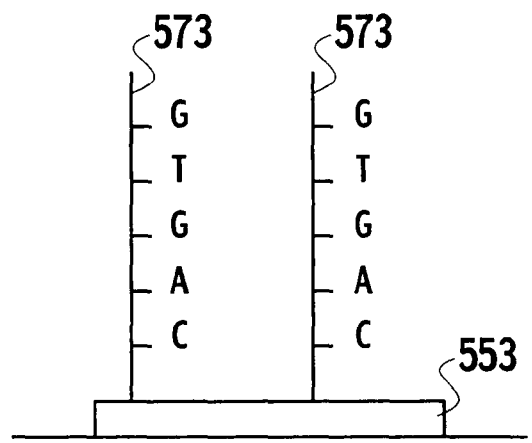
FIG. 10C is a schematic plot depicting two strands of probe DNA (negative control DNA) immobilized to the top surface of the control electrode, showing that sample DNA with SNP="T" is unable to form a double-strand with probe DNAs.

FIGS. 10A-10C show three cases in which the sample DNA 582 is a target nucleotide sequence having a nucleotide sequence CTTAG . . . (SNP="T" of sample DNA). Similarly, through the hybridization process by the chip cartridge 11, as shown in FIG. 10B, the active electrode (SNP2 detecting electrode) 552 can form a double-strand, since the sequence completely matches with the target nucleotide sequence having a nucleotide sequence CTTAG . . . (sample DNA with SNP="T"). However, if the sequence contains even one different base, a double-strand cannot be formed. Accordingly, as shown in FIG. 10A, the active electrode (SNP1 detecting electrode) 551 at which the probe DNA 571 having a nucleotide sequence GACTC . . . is fixed cannot form a double-strand with the target nucleotide sequence (sample DNA with SNP="T") 582. If the sequence is completely different, a double-strand, of course, cannot be formed. Therefore, as shown in FIG. 10C, the active electrode (control electrode) 553 at which the probe DNA (negative control DNA) 573 having a nucleotide sequence CAGTG . . . is fixed cannot form a double-strand with the target nucleotide sequence (sample DNA with SNP="T") 582.

Figure 11A:
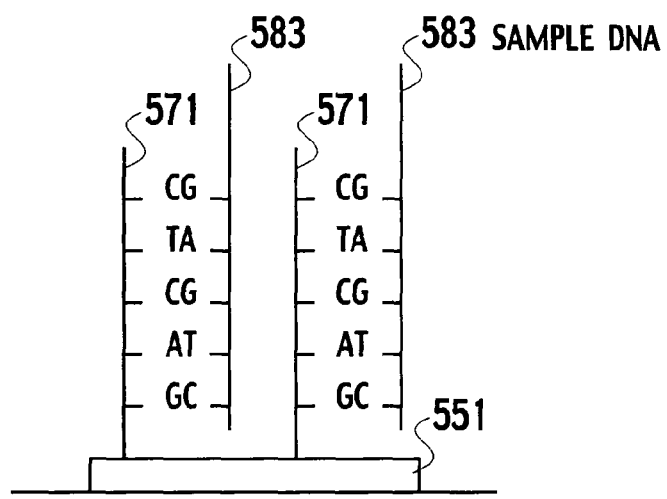
FIG. 11A is a schematic plot depicting two strands of probe DNAs, immobilized to the top surface of the SNP="G/T" detecting electrode, and two strands of heterogeneous sample DNA with SNP="G/T", which are paired into double-strands with the probe DNAs, because the nucleotide sequences match with the probe DNAs.
Figure 11B:
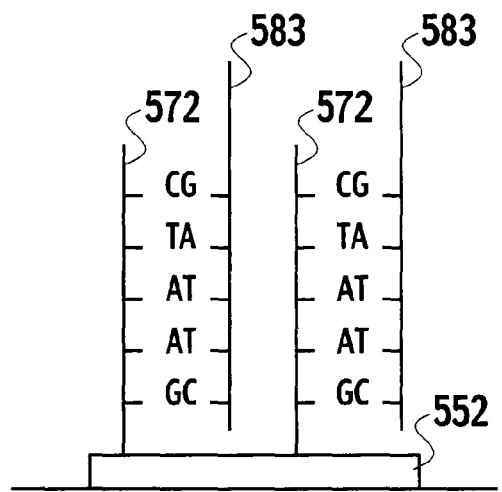
FIG. 11B is a schematic plot depicting two strands of probe DNA, immobilized to the top surface of the SNP="G/T" detecting electrode, and two strands of heterogeneous sample DNA with SNP="G/T", which are paired into double-strands with the probe DNAs, because the nucleotide sequences match with the probe DNAs.
Figure 11C:
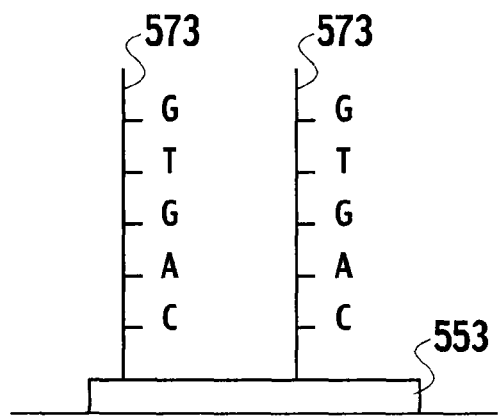
FIG. 11C is a schematic plot depicting two strands of probe DNA (negative control DNA) immobilized to the top surface of the control electrode, showing that heterogeneous sample DNA with SNP="G/T" is unable to form a double-strand with probe DNAs.

FIGS. 11A-11C show three cases in which the sample DNA 583 is a target nucleotide sequence (sample DNA with SNP="G") having a nucleotide sequence CTGAG . . . . Similarly, through the hybridization process by the chip cartridge 11, as shown in FIG. 11A, the active electrode (SNP1 detecting electrode) 551 at which the probe DNA 571 having GACTC . . . is fixed can form a double-strand, since the sequence completely matches with the "G/T" hetero target nucleotide sequence 583 having both nucleotide sequences CTGAG . . . and CTTAG . . . (sample DNA with SNP="G/T" hetero). As shown in FIG. 11B, the active electrode (SNP2 detecting electrode) 552 at which the probe DNA 572 having a nucleotide sequence GAATC . . . is fixed can form a double-strand, since the sequence completely matches with the target nucleotide sequence (sample DNA with SNP="G/T" hetero) 583. However, if the sequence is completely different, a double-strand, of course, cannot be formed. Therefore, as shown in FIG. 11C, the active electrode (control electrode) 553 at which the probe DNA (negative control DNA) 573 having a nucleotide sequence CAGTG . . . is fixed cannot form a double-strand with the "G/T" hetero target nucleotide sequence (sample DNA with SNP="G/T" hetero) 583.

When adopting another architecture that is different from the configuration shown in FIG. 4 and FIG. 5, that is, when adopting a configuration that mounts a planar packing-plate on the substrate (chip) and forms a flow path within a cassette (chip cartridge), the flow path within a cassette (detection chip) 21 is extended, which increases the amount of unnecessary reagent. In addition, when injecting automatically chemicals (sample solution) in the cassette (detection chip) 21 by valve unit 705 provided in the fluid transport system 13 as shown in FIG. 6, the flow path remains long not only on the substrate but also within the cassette (detection chip) 21. Therefore, the chemicals (sample solution) flow into undesired parts other than the substrate, which results in waste. In addition, as a result of insufficient adhesion of the cassette (detection chip) 21 to the packing-plate, leakage occurs between the packing-plate and the cassette (detection chip) 21 leading to failures in solution delivering. The configuration according to the present embodiment reduces the amount of unnecessary reagent, improves the adhesion of packing-plate, substrate and cassette (detection chip) 21, and increases the stability of solution conveyance.

Figure 12A:
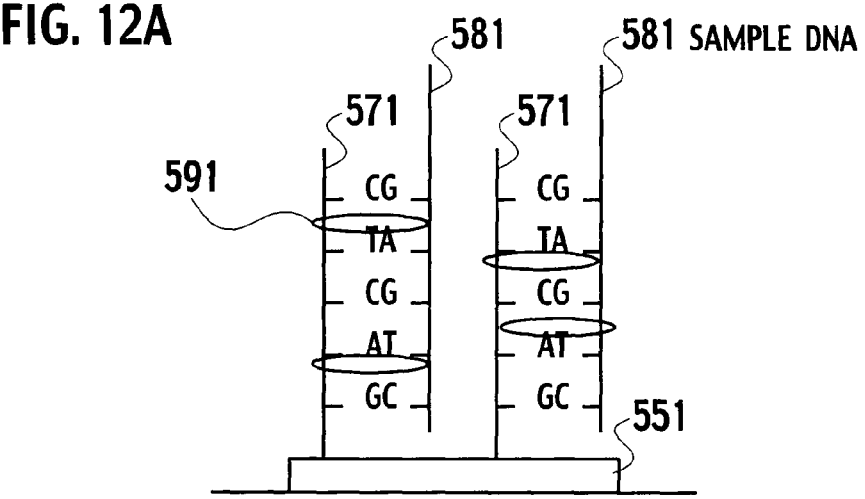
FIG. 12A is a schematic plot depicting two strands of probe DNAs, immobilized to the top surface of the SNP1 detecting electrode (SNP="G" detecting electrode), and two strands of sample DNA with SNP="G", which are paired into double-strands with the probe DNAs, and intercalation agents have intercalated into the double-strand.
Figure 12B:
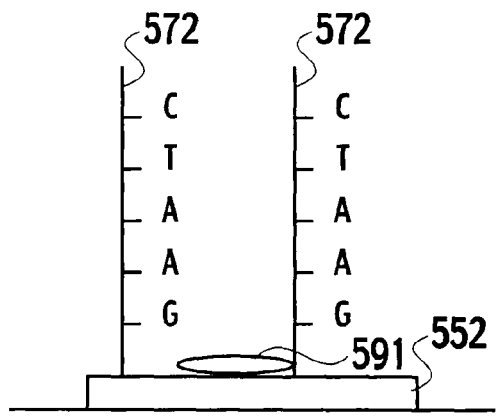
FIG. 12B is a schematic plot depicting two strands of probe DNA immobilized to the top surface of the SNP2 detecting electrode (SNP="T" detecting electrode), showing that the intercalation agent can not be intercalated, because the sample DNA with SNP="G" is unable to form a double-strand with probe DNAs.
Figure 12C:
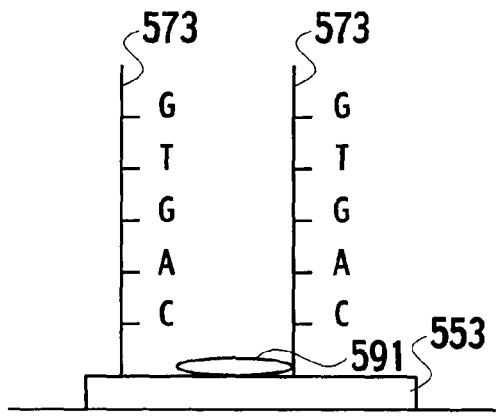
FIG. 12C is a schematic plot depicting two strands of probe DNA (negative control DNA) immobilized to the top surface of the control electrode, showing that the intercalation agent can not be intercalated, because the sample DNA with SNP="G" is unable to form a double-strand with probe DNAs.

Similarly to the above-mentioned FIGS. 9A-9C, FIGS. 12A-12C show three conditions in which the intercalation agent 591 is introduced in each of active electrodes 551, 552, 553 that is hybridized by the target nucleotide sequence (sample DNA) 581 having a nucleotide sequence CTGAG . . . . As shown in FIG. 12A, for the active electrode (SNP1 detecting electrode) 551 at which the probe DNA 571 having a nucleotide sequence GACTC . . . is fixed, the sequence completely matches the target nucleotide sequence (sample DNA) 581 having a nucleotide sequence CTGAG . . . ; therefore, the intercalation agent 591 bonds to the double-strand DNA. However, as shown in FIG. 12B, the active electrode (SNP2 detecting electrode) 552 at which the probe DNA 572 having a nucleotide sequence GAATC . . . is fixed cannot form a double-strand with the target nucleotide sequence (sample DNA) 581; therefore, the intercalation agent 591 cannot be intercalated. Also as shown in FIG. 12C, the intercalation agent 591 cannot be intercalated to the active electrode (control electrode) 553 at which the probe DNA (negative control DNA) 573 having a nucleotide sequence CAGTG . . . is fixed, since it cannot form a double-strand with a target nucleotide sequence (sample DNA) 581.

FIG. 13 shows an electrochemical current from the intercalation agent 591 intercalated to the double-strand DNA hybridized to the probe DNAs 571, 572, 573 that are fixed on each of active electrodes 551, 552, 553 or a relation between current and voltage when the intercalation agent 591 cannot be intercalated to the double-strand DNA. In FIG. 13, a curved line labeled with (a) corresponds to FIG. 12A. Briefly, the curved line labeled with (a) refers to the current-voltage characteristic of electrochemical current when the probe DNA 571 sequence and the target nucleotide sequence (sample DNA) 581 completely matches, forms a double-strand, and the intercalation agent 591 is intercalated with the double-strand, and indicates a peak of high current value. However, in FIG. 13, a curved line labeled with (b), corresponding to FIG. 12B, refers to the current-voltage characteristic of electrochemical current when the probe DNA 572 cannot form a double-strand with the target nucleotide sequence (sample DNA) 581, and the intercalation agent 591 cannot be intercalated and indicates a peak of low current value compared to the curved line labeled with (a). In addition, in FIG. 13, a curved line labeled with (c), corresponding to FIG. 12C, refers to the current-voltage characteristic when the negative control DNA 573 cannot form a double-strand with the target nucleotide sequence (sample DNA) 581 and the intercalation agent 591 cannot be intercalated, and indicates a peak of lower current value compared to the curved line labeled with (b). The low current value peaks observed in the curved lines labeled with (a). and (c), are the currents derived from the intercalation agent 591 slightly absorbed to the surface of electrode 552 and 553, as shown in FIGS. 12B and 12C.

After a long introduction, the nucleotide sequence determination method according to the embodiment of the present invention will now be explained with reference to the flowchart shown in FIG. 14:

(i) First, chemicals (sample solution) containing the sample DNA are injected automatically into the chip cartridge 11 using valve unit 705 provided in the fluid transport system 13 as shown in FIG. 6 so as to induce the hybridization reaction. Using the detecting system 12, the current-voltage characteristic of the electrochemical reaction derived from introducing the intercalation agent is measured for each electrode. FIG. 4 shows a schematic plot of multiple electrode units 761 on the substrate 714. Corresponding to the multiple electrode units 761, there are many SNP1 detecting electrodes 551, SNP2 detecting electrodes 552, and control electrodes 553 at which the probe DNAs 571, 572, 573 are fixed respectively as equivalent electrodes. Corresponding to those electrodes, a great deal of data can be obtained. In step S101, the noise removing module 301 removes noise by smoothing each dataset measured for each electrode at which the probe DNAs 571, 572, 573 are fixed. The smoothing, as described above, may employ the simple moving average method as shown in FIG. 15.

(ii) Next, in step S102, the current-profile judgement module 302 determines the respective slopes of the tail lines (characteristic baselines) in the current waveforms (current-voltage characteristics) measured for each electrode. Based on each baseline slope, the normality and abnormality of each detection signal (current waveform) are determined. The abnormal detection signal is excluded from the calculation. Details on the processing of the current-profile judgement module 302 in step S102 will be described below in reference to a flowchart in FIG. 16.

(iii) In step S103, the net current calculation module 310 detects peak values (peak current values) of the detection signals measured for each electrode respectively. Details on the processing of the net current calculation module 310 in step S103 will be described below in reference to a flowchart in FIG. 18A and FIG. 18B. By the processing in step S103, the net peak values of the detection signals (peak current values) can be obtained as a dataset for respective electrodes by subtracting the other background currents from the electrochemical currents derived from the intercalation agent 591 as shown in FIGS. 12A-12C.

(iv) After removing the background current components in step S103, each dataset is treated by a signal processing in step S104. Briefly, in step S104, the abnormal-data eliminating module 320 eliminates the abnormal data from each dataset. Details on the processing of the abnormal-data eliminating module 320 in step S104 will be described below in reference to a flowchart in FIG. 24.

(v) In step S105, the presence judgement module 330 determines the presence of nucleic acid, or the typing module 340 determines the type of single nucleotide polymorphisms (SNP) of nucleic acid. Details on each processing of the presence judgement module 330 and typing module 340 in step S105 will be described below in reference to a flowchart in FIG. 25A-FIG. 25D.

Figure 14:
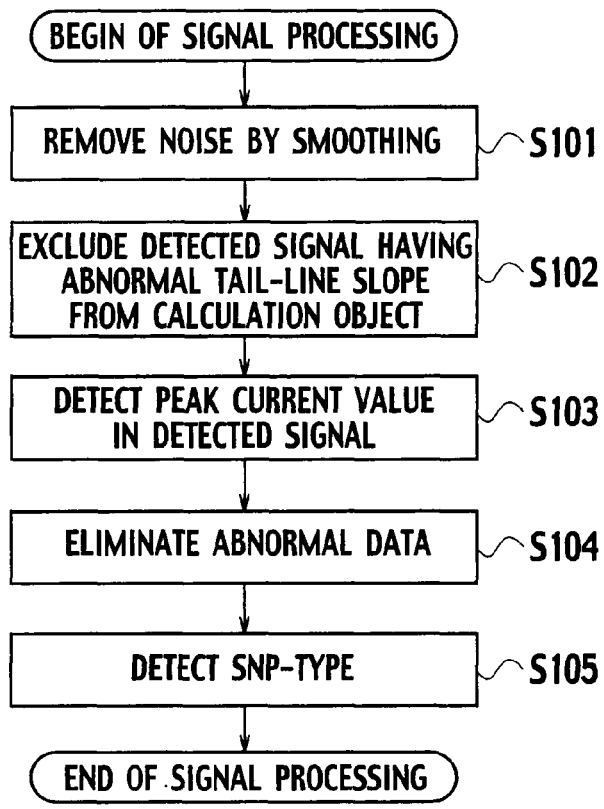
FIG. 14 is a flow chart explaining the overall process of the nucleotide sequence determination method according to the embodiment of the present invention.

According to the nucleotide sequence determination method associated with the embodiment of the present invention shown in a flowchart in FIG. 14, even when there are abnormalities in the chip cartridge 11 and the detecting system 12, and when there is dispersion in data, it is possible to precisely determine whether a certain nucleic acid exists, what the SNP type is, and whether the type is homogeneous or heterogeneous. Hereinafter, each step of the flowchart shown in FIG. 14 will be explained in detail.

Step S102

Determination of Normality/Abnormality of the Current Waveform

The electrochemical current signals (current waveforms) in the chip cartridge 11 measured by the detecting system 12 in FIG. 1 manifest waveforms of the current-voltage characteristics as shown in FIG. 17. For the voltage specific to substances (intercalation agents) that issue electrical signals, it has a waveform of the current-voltage characteristic having a peak shape as shown in FIG. 17. FIG. 17 shows two types of the current-voltage characteristics as labeled with "data 1" and "data 2". Compared to the slope of the tail line (characteristic baseline) indicated by the current-voltage characteristic labeled with "data 1", the slope of the tail line (characteristic baseline) indicated by the current-voltage characteristic labeled with "data 2" is larger. In the current-voltage characteristic labeled with "data 2", the peak shape is unclear, showing a shoulder-like variation.

Ideally, the current-voltage characteristic of the electrochemical current shows a substantially "zero" current value for voltages lower than the voltage that generates a peak current. However, when any failures occur on the substrate 714, for example, a slope of the tail line (characteristic baseline) in the current-voltage characteristic becomes larger as the current-voltage characteristic labeled with "data 2". With the current-voltage characteristic labeled with "data 2", the peak current value cannot be detected accurately. Therefore, the current-voltage characteristic having a larger slope of the tail line (characteristic baseline) must be excluded as "abnormal" in step S102 of FIG. 14.

Figure 16:
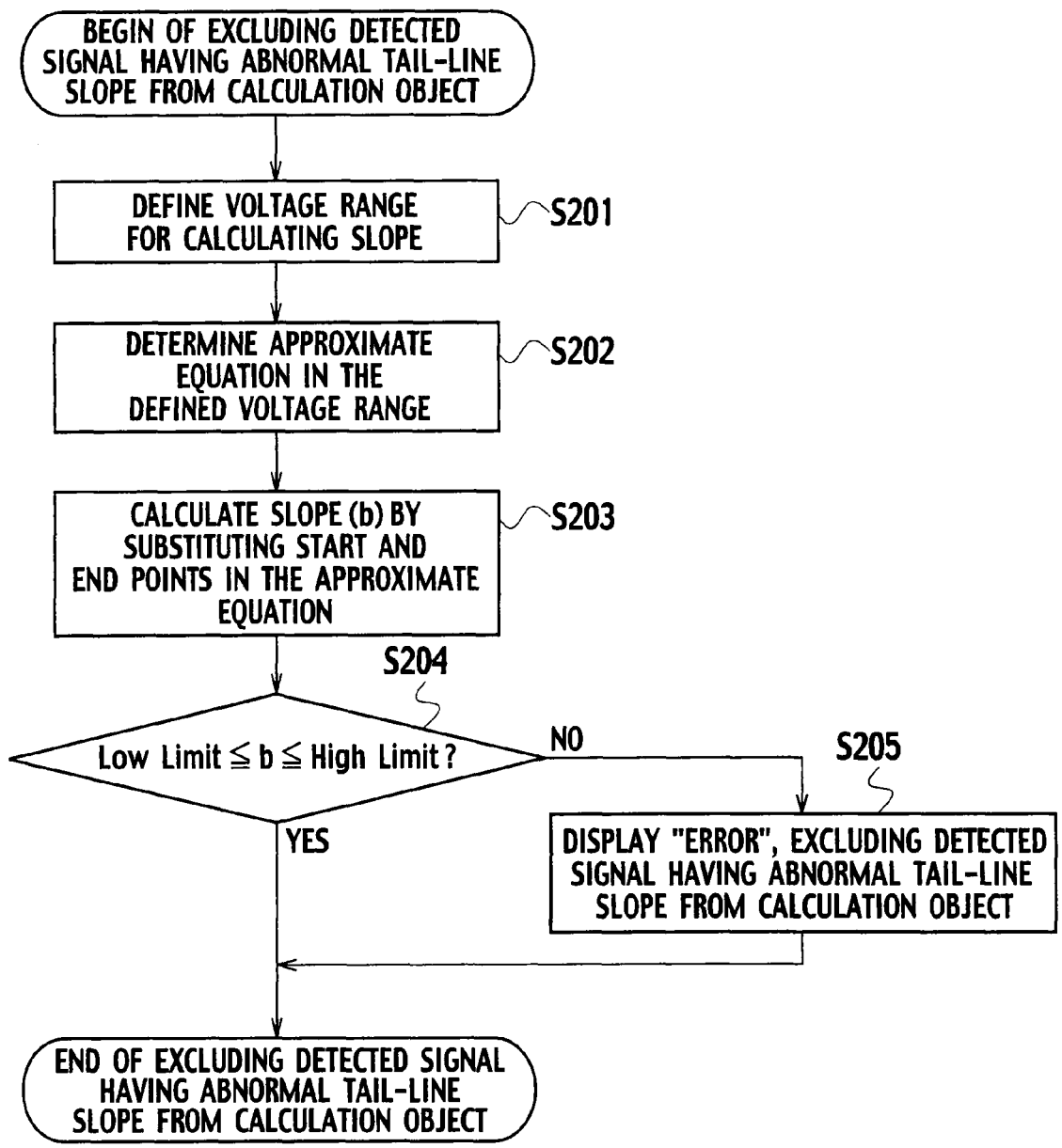
FIG. 16 is a flow chart explaining one example of the method of determination of normality or abnormality in current wave forms (current-voltage characteristics) based upon the slopes of the tail lines (characteristic baselines) of the current wave forms, using the electro-chemical currents measured by a plurality of electrodes, respectively.

Details on the procedure by the current-profile judgement module 302 in step S102 are as shown in a flowchart of FIG. 16.

(a) First, in step S201, a voltage range for calculating the slopes of the tail lines (characteristic baselines) of the currents waveform (current-voltage characteristic) measured for each electrode is extracted and determined. In the case of extraction in the voltage range, the lower limit voltage VLo and the higher limit voltage VHi (VLo<VHi) are determined as predetermined parameters, using the input unit 304, and stored in the voltage range storing unit (for waveform-judgement) 351. In addition, as a parameter for specifying the allowable slope range of the tail line (characteristic baseline), "Coefficient lower limit value (Coef Lo)" and "Coefficient higher limit value (Coef Hi)" are determined and stored in the allowable slope range storing unit 352.

(b) Next, in step S202, the current-profile judgement module 302 reads out the lower limit voltage VLo and the higher limit voltage VHi stored in the voltage range storing unit (for waveform-judgement) 351, and derives an approximation expression for the slope of the tail line (characteristic baseline) in the determined voltage range. The lower limit voltage VLo and the higher limit voltage VHi are parameters to specify the voltage range for calculating the slope of the tail line (characteristic baseline). The straight line (preliminary baseline) is obtained by a least squares approximation to the current-voltage characteristic waveform measured for each electrode, using the voltage range between the lower limit voltage VLo and the higher limit voltage VHi.

(c) In step S203, the current-profile judgement module 302 calculates the slope (b) of the tail line (characteristic baseline) of the current waveform (current-voltage characteristic) measured for each electrode by setting the read lower limit voltage VLo and higher limit voltage VHi as a starting point and an ending point respectively for each current waveform (current-voltage characteristic) measured for each electrode.

(d) Thereafter, in step S204, the current-profile judgement module 302 reads out the "coefficient lower limit value (Coef Lo)" and the "coefficient higher limit value (Coef Hi)" from the allowable slope range storing unit 352, and determines if the slope of the tail line (characteristic baseline) calculated for each electrode exists between the "coefficient lower limit value (Coef Lo)" and the "coefficient higher limit value (Coef Hi)" respectively.

(e) In step S204, when the slope of the tail line (characteristic baseline) for the current waveform (current-voltage characteristic) measured by a certain electrode exists between the "coefficient lower limit value (Coef Lo)" and "coefficient higher limit value (Coef Hi)", it is determined as a "normal waveform". Then, proceed to step S103 shown in FIG. 14. In step S204, the current waveform (current-voltage characteristic) measured by a certain electrode is determined to be out of the slope range between the "coefficient lower limit value (Coef Lo)" and the "coefficient higher limit value (Coef Hi)", the current waveform (current-voltage characteristic) measured by the electrode is determined to be an "abnormal waveform". In step S205, the current-profile judgement module 302 issues "error determination" to the current waveform (current-voltage characteristic) measured by the electrode, and makes the display unit 306 display "error" or makes the output unit 305 transfer the "error determination" to an external device.

The sequence of process-steps shown in FIG. 16 is executed for all electrode units 761 on the substrate 714 shown in FIG. 4.

Step S103

Detection of the Peak Current Value

Details on the procedure by the net current calculation module 310 in step S103 will be explained in reference to a flowchart in FIG. 18A and FIG. 18B.

In step S103, the procedure for detecting respective net peak current value from the waveform of the current-voltage characteristic by each of electrode units 761 measured by the detecting system 12 is implemented by a sequence of:

calculating the voltage value that gives a current peak in steps S221-S223 (see differential current value vs. voltage characteristic shown in FIG. 19);

approximating the baseline (background baseline) in steps S224-S228 (see differential current value vs. voltage characteristic and current-voltage characteristics shown in FIG. 20 and FIG. 21); and calculating the peak current value in steps S229-S230 (see current-voltage characteristics shown in FIG. 22) for respective current-voltage characteristics measured by the plurality of electrode units 761.

(a) A current peak indicated by the current-voltage characteristic of the electrochemical current measured by the chip cartridge 11 appears in a substantially constant voltage range. Therefore, in step S221, using the input unit 304 shown in FIG. 8, the peak-current-searching voltage range [V1, V2] is preliminary stored in the voltage range storing unit (for peak-current searching) 353 as a predetermined parameter. Briefly, as shown in FIG. 19, the peak current search of the electrochemical current is conducted in a voltage range between the lower limit value V1 and the upper limit value V2. First, in step S222, the voltage calculation unit 311 of the net current calculation module 310 differentiates current (i), which represents the waveform of the current (i)-voltage (v) characteristic of the electrochemical current, with respect to the voltage value (v) so as to obtain differential curves of each of the current-voltage characteristics. Then, in step S223, the voltage calculation unit 311, in a voltage range between the lower limit value V1 and the upper limit value V2, the voltage value (zero-cross voltage value) $V_{pk1}$ and the current value (zero-cross current value) $I_{pk1}$ at the point where each of the differential curves of the electrochemical currents (di/dv) "zero-crosses" (see FIG. 19). The point to "zero-cross" refers to the point at which each of the differential curves (di/dv) of the electrochemical currents varies from positive to negative, or alternatively from negative to positive, which corresponds to the voltage value $V_{pk1}$ and the current value $I_{pk1}$ that gives a current peak. FIG. 19 shows the voltage value $V_{pk1}$ and the current value $I_{pk1}$ at the point at which representative one of the differential curves (di/dv) varies from negative to positive as the voltage value increases. When there is an odd number of "zero-cross values," the center value is adopted as the voltage value $V_{pk1}$. When there is an even number of "zero-cross values," the most approximate value to the center value is adopted as the voltage value $V_{pk1}$. The zero-cross value memory 354 sorts to a specified order and stores the "zero-cross value (zero-cross voltage value $V_{pk1}$, zero-cross current value $I_{pk1}$)" in each of all electrode units 761 on the substrate 714 shown in FIG. 4.

Figure 22:
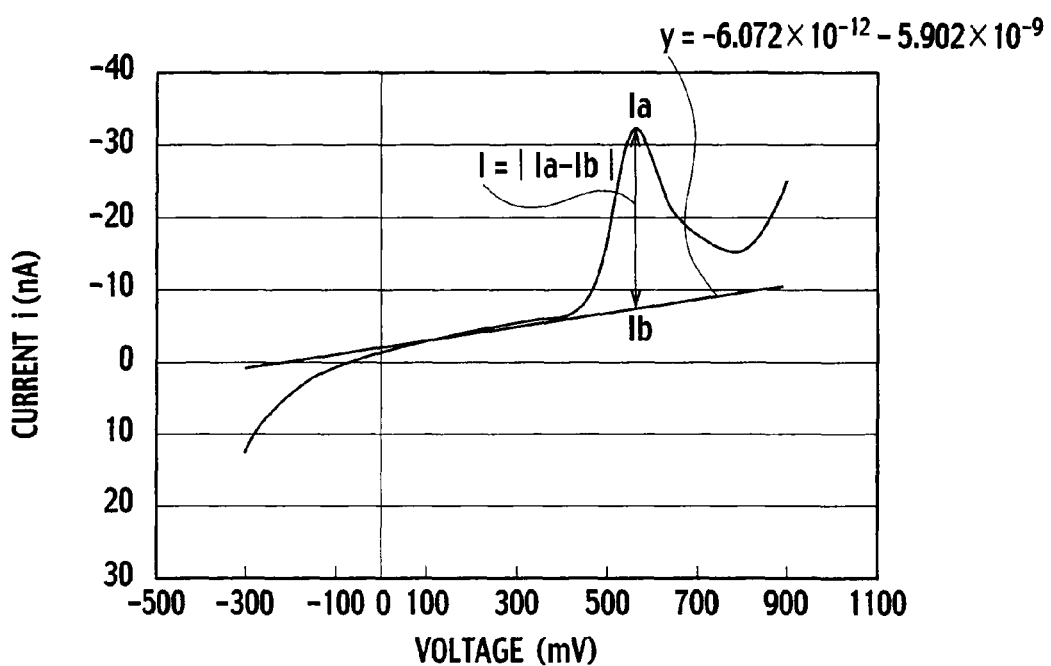
FIG. 22 is a schematic plot explaining the method for obtaining the net detected signal (peak current value) from the peak current at the zero-cross voltage, subtracting the corresponding background current, in the nucleotide sequence determination method according to the embodiment of the present invention.

(b) In step S224, the baseline approximation unit 312 of the net current calculation module 310, define an inflection point voltage $V_{ifp}$ as shown in FIG. 20. The "inflection point voltage $V_{ifp}$" is the voltage at which each of the differential curves is minimized, by tracing the voltage from the zero-cross voltage value $V_{pk1}$ that gives the current peak, in a negative direction (by decreasing the voltage). The inflection point voltage $V_{ifp}$ is sorted and stored in the inflection point memory 355. Then, in step S225, the baseline approximation unit 312 reads out the zero-cross voltage $V_{ifp}$ and the inflection point voltage $V_{ifp}$ from the zero-cross value memory 354 and the inflection point memory 355 respectively. Furthermore, in step S225, the baseline approximation unit 312 approximates the following linear expression of each of the current-voltage characteristic curves:

$$y = ax + b \quad (3)$$

between the zero-cross voltage value $V_{pk1}$ and the inflection point voltage $V_{ifp}$ so as to obtain an original point of the baseline (background baseline). The linear expression represented by Eq. (3) approximates the slope of the shoulder in the peaking portion of the current-voltage characteristic curve as shown in FIGS. 20 and 21. For example, the waveform data of the current-voltage characteristic between the zero-cross voltage value $V_{pk1}$ and the inflection point voltage $V_{ifp}$ is approximated by a least square approximation. In an example of FIG. 20, the resulting coefficient "a" and constant "b" of the linear expression are:

$$a = -1397 \times 10^{-10}; \text{ and}$$

$$b = 3.396 \times 10^{-9}$$

respectively. In an example shown in FIG. 21, the resulting coefficient "a" and constant "b" of the linear expression are:

$$a = -2.899 \times 10^{-11}; \text{ and}$$

$$b = 4.504 \times 10^{-9}$$

respectively. Furthermore, the baseline approximation unit 312, in step S226, calculates the intersection-point voltage $V_{crs}$ at an intersection-point of each of the current-voltage characteristic waveforms and the corresponding approximation line of Eq. (3) as shown in FIG. 21, and each of the intersection-point voltages $V_{crs}$ is sorted and stored in the intersection-point voltage memory 356. The baseline approximation unit 312, in step S227, defines each of the offset voltages $V_{ofs}$ by tracing the voltage starting from the corresponding intersection-point voltage value $V_{crs}$, as much as the offset value defined as a predetermined parameter, in a negative direction (by decreasing the voltage) in each of the current-voltage characteristic waveforms. The obtained offset voltage $V_{ofs}$ is sorted and stored in the offset voltage memory 357. In addition, the baseline approximation unit 312 reads out the offset voltage $V_{ofs}$ from the offset voltage memory 357 and the intersection-point voltage $V_{crs}$ from the intersection-point voltage memory 356. In step S228, the approximate linear expression serving as a tangential line (reference baseline) to the background of each of the waveform data for the current-voltage characteristics, between the offset voltage $V_{ofs}$ and the intersection-point voltage $V_{crs}$, is obtained by method of least squares as shown in FIG. 22. The approximate linear expression can be expressed in a similar format to Eq. (3). In the linear approximation shown in FIG. 22, the resulting coefficient "a" and constant "b" of the linear expression are:

$$a = -6.072 \times 10^{-12}; \text{ and}$$

$$b = 5.902 \times 10^{-9}$$

respectively.

(c) Thereafter, the net-current-value calculation unit 313 of the net current calculation module 310 reads out the zero-cross voltage value $V_{pk1}$ from the zero-cross value memory 354. Then, in step S229, the net-current-value calculation unit 313 substitutes the corresponding zero-cross voltage value $V_{pk1}$ to each of the approximate linear expressions of the baselines (background baselines) obtained in step S228 to obtain a plurality of background current values $I_{bg}$ on the baselines (background baselines) serving as reference backgrounds. The background current values $I_{bg}$ on the baselines (background baselines) are sorted and stored in the baseline-current value memory 358. Furthermore, the net-current-value calculation unit 313 reads out the zero-cross current value $I_{pk1}$ that shows a peak of the waveform for the current-voltage characteristic from the zero-cross value memory 354. In step S230, by applying Eq. (4):

$$I_{pk2} = \text{abs}(I_{pk1} - I_{bg}) \quad (4)$$

at which each of the current values of the baselines (background baselines) $I_{bg}$ serving as reference backgrounds is subtracted from the corresponding zero-cross current value $I_{pk1}$ as shown in Eq. (4). The subtraction of Eq. (4) is executed to each of the current-voltage characteristics, each of which is measured by corresponding SNP1 detecting electrode (SNP="G" detecting electrode) 551, corresponding SNP2 detecting electrode (SNP="T" detecting electrode) 552, and corresponding control electrode 553 in each of electrode units 761. Then, a plurality of net current values $I_{pk2}$ are calculated for the plurality of electrodes 551, 552, 553 in each of the plurality of electrode units 761.

Step S104

Elimination of Abnormal Data

As described above, in step S103 in FIG. 14, the net current calculation module 310 subtracts the background current value $I_{bg}$ of the baseline (background baseline) from the zero-cross current value $I_{pk1}$ that shows a peak of respective current-voltage characteristic derived from each of electrode units 761 measured by the detecting system 12. As a result, the respective net current values $I_{pk2}$ for a plurality of SNP1 detecting electrodes (SNP="G" detecting electrodes) 551, a plurality of SNP2 detecting electrodes (SNP="T" detecting electrodes) 552, and a plurality of control electrodes 553 are calculated and sorted for each of electrode units 761, with various determination modes. Modes A-F shown in FIGS. 23A-23C and FIGS. 23D-23F are representative examples of such determination modes. In FIGS. 23A-23C and FIGS. 23D-23F, a plurality of detection signals are classified into collective bar graphs with modes A-F. In respective bar graphs showing modes A-F, a group of bars showing the current values $I_{pk2}$ labeled with "control" at the left end are values measured by the plurality of control electrodes 553. A group of bars showing the current values $I_{pk2}$ labeled with "T" at the center are values measured by the plurality of SNP2 detecting electrodes (SNP="T" detecting electrode) 552. A group of bars showing the current values $I_{pk2}$ labeled with "G" at the right end are values measured by the plurality of SNP1 detecting electrodes (SNP="G" detecting electrode) 551.

However, in the nucleotide sequence determination method according to the embodiment of the present invention, the classification into modes A-F shown in FIGS. 23A-23C and FIGS. 23D-23F is not always immediately possible. For example, when a specific value is abnormally high or low for only one electrode within the plurality of equivalent SNP1 detecting electrodes (SNP="G" detecting electrode) 551, or, when a specific value is abnormally high or low for only one electrode within the plurality of equivalent SNP2 detecting electrodes (SNP="T" detecting electrode) 552, the determination algorithm is disrupted unless these abnormal values are excluded. Briefly, in the process-step S105 shown in FIG. 14, when all of the peak current values $I_{pk2}$ obtained from the plurality of equivalent electrode units 761 arranged on the substrate 714 as shown in FIG. 4 are employed so as to determine whether a certain nucleic acid exists, which of two the SNP type is, and whether it is homo-type or hetero-type, problems might occur.

Accordingly, in step S104 of FIG. 14, prior to going to step S105, the abnormal-data eliminating module 320 execute a sequence of process-steps prescribed by the flowchart shown in FIG. 24 so as to eliminate a specific data with abnormal values under certain criterion from subject group, the sequence of process-steps being executed respectively in every groups of the current values $I_{pk2}$, which are obtained from all of electrode units 761 arranged on the substrate 714 shown in FIG. 4 until all of the abnormal data are eliminated from all of the groups.

(a) In step S301, the abnormal-data eliminating module 320 adopts a plurality of current values $I_{pk2}$ obtained from all electrodes, the current values being divided into a plurality of groups, each of the group implements unit dataset. Each of group is defined for a combination of equivalent electrodes. Briefly, each of the groups is defined for a combination of corresponding SNP1 detecting electrodes (SNP="G" detecting electrode) 551, corresponding SNP2 detecting electrodes (SNP="T" detecting electrode) 552, and corresponding control electrodes 553 in every electrode units 761.

(b) For the first group, the abnormal-data eliminating module 320 calculates the standard deviation and the mean-value of the current values $I_{pk2}$ obtained from all electrodes defined in the first group. Then, in step S302, the first CV value CV (0) is calculated by dividing the standard deviation for the first group by the mean-value for the first group. The abnormal-data eliminating module 320 reads out the standard CV value CV (%) specified as a predetermined parameter from the CV-value memory 361, and compares the standard CV value CV (%) to the first CV value CV (0) in step S303. When the first CV value CV (0) is smaller than the standard CV value CV (%), determining all current values $I_{pk2}$ have normal values, respectively, the abnormal-data eliminating module 320 goes to the next determination algorithm (step S105 in FIG. 14). For the other group as well, a sequence of process-steps from step S302 to step S303 are repeated for all groups to eliminate a group (or a plurality of groups) with the abnormal value.

(c) In step S303, if the first CV value CV (0) is equal to or larger than the standard CV value CV (%), after storing the first CV value CV (0) in the CV-value memory 361, the abnormal-data eliminating module 320 goes to step S304, eliminates data of the minimum value from a dataset of the subject group, and calculates the standard deviation and the mean-value of the current values $I_{pk2}$ obtained from all other electrodes defined in the subject group again. In step S304, the abnormal-data eliminating module 320 calculates the second CV value CV (1) by dividing the standard deviation of a new dataset, from which data of the minimum value is eliminated, by the mean-value of the new dataset, from which data of the minimum value is eliminated, and goes to step S305.

(d) In step S305, the abnormal-data eliminating module 320 reads out the first CV value CV (0) and the CV value correction coefficient dCV/CV from the CV-value memory 361 to compare the size between the corrected (multiplied) value in which the first CV value CV (0) is multiplied by the CV value correction coefficient dCV/CV and the second CV value CV (1):

$$(CV(0))*(dCV/CV) > CV(1) \tag{5}$$

(e) In step S305, when the corrected (multiplied) value in which the first CV value CV (0) is multiplied by the CV value correction coefficient dCV/CV is determined to be smaller than the second CV value CV (1), the result means the elimination of the data of the minimum value was inappropriate; therefore, the determination procedure goes to step S321. The abnormal-data eliminating module 320, in step S321, recovers the data of the minimum value eliminated from the dataset for the subject group and this time eliminates data of the maximum value from the dataset for the subject group to calculate the standard deviation and the mean-value of the current values $I_{pk2}$ obtained from all other electrodes defined in the subject group again. In step S321, the abnormal-data eliminating module 320 calculates the third CV value CV (2) by dividing the standard deviation of the dataset from which data of the maximum value is eliminated by the mean-value of the dataset from which data of the maximum value is eliminated, and goes to step S322.

(f) In step S322, the abnormal-data eliminating module 320 reads out the first CV value CV (0) and the CV value correction coefficient dCV/CV from the CV-value memory 361 to compare the size between the corrected (multiplied) value in which the first CV value CV (0) is multiplied by the CV value correction coefficient dCV/CV and the third CV value CV (2):

$$(CV(0))*(dCV/CV) > CV(2) \tag{6}$$

(g) When the corrected (multiplied) value in which the first CV value CV (0) is multiplied by the CV value correction coefficient dCV/CV in step S322 is smaller than the third CV value CV (2), since the eliminated data can be determined that the eliminated data has an abnormal value, the determination procedure goes to step 325 and performs a process of "error set", defining the data of the maximum value eliminated in step S321 to be "data out of calculation object." In the succeeding determination flow (step S105 in FIG. 14), data of the maximum value is eliminated from the determination procedure.

(h) When the corrected (multiplied) value in which the first CV value CV (0) is multiplied by the CV value correction coefficient dCV/CV in step S322 is not smaller than the third CV value CV (2), since the subject dataset can be determined that there are some other data to be eliminated, the determination procedure goes to step 323, defines the dataset from which data of the maximum value is eliminated in step S321 to be a new dataset, and goes to step S324. In step S324, the abnormal-data eliminating module 320 performs a process of "error set", defining the data of the maximum value eliminated in step S321 as "data out of calculation object," returns to step S302, and repeats the above-mentioned sequence of process-steps.

(i) Similarly, in step S305, when the corrected (multiplied) value in which the first CV value CV (0) is multiplied by the CV value correction coefficient dCV/CV is not smaller than the second CV value CV (1), the determination procedure goes to step S306, defines the dataset from which data of the minimum value is eliminated in step S304 as a new dataset, and goes to step S307. In step S324, the abnormal-data eliminating module 320 performs a process of "error set", defining the data of the minimum value eliminated in step S304 to be "data out of calculation object," returns to step S302, and repeats the above-mentioned sequence of process-steps.

After repeating the above-mentioned routines for all groups, data with abnormal value are eliminated. The abnormal-data eliminating module 320 executes an "error determination" when a specific data of the current value $I_{pk2}$ obtained from electrodes is determined as data out of the calculation object, and the display unit 306 displays "error", and the output unit 305 provide information of the "error determination" to an external device. In the succeeding steps, the calculation is subject to the net current value $I_{pk2}$; therefore, if not otherwise specified, a "net current value $I_{pk2}$" is hereinafter described as a "current value."

Step S105

Two Genotyping Algorithms

Step S105 in FIG. 14 contains two genotyping algorithms as shown in FIG. 25A. Therefore, first in step S332, it is decided which flow of genotyping algorithm to be employed: one for determining the presence of a certain nucleic acid and another for determining which of two the SNP type is, and whether it is G/G homo-type, G/T hetero-type, or T/T homo-type.

[Step S105-1: Presence Determination of Nucleic Acid]

In step S332 of FIG. 25A, when it is decided to employ the flow of genotyping algorithm for determining the presence of a certain nucleic acid, the presence judgement module 330 determines according to the procedure of the flowchart shown in FIG. 25B. When the determination procedure is executed by eliminating abnormal data, for example, symbol "#" may be labeled in the final determination result in order to show that the determination was done after eliminating abnormal data.

FIG. 2 shows an electrode unit in which a plurality of SNP1 detecting electrodes 551, a plurality of SNP2 detecting electrodes 552, a plurality of control electrodes 553, reference electrodes 561, 562, and opposite electrode 502 are arranged on the detection chip. However, for the case of a genotyping algorithm to determine the presence of a certain nucleic acid, one of either the set of SNP1 detecting electrodes 551 or the set of SNP2 detecting electrodes 552 may be arranged. That is, on the substrate 714 shown in FIG. 4, the plurality of electrode units 761 that contain either the set of SNP1 detecting electrodes 551 or the set of SNP2 detecting electrodes 552 as a subject set of detecting electrodes (active electrodes) are arranged. Wherein, it is explained assuming that the set of detecting electrodes (active electrodes) for detection a genotype 1 is the set of SNP1 detecting electrodes 551 shown in FIG. 2.

(a) In step S341, the presence judgement module 330 calculates the mean current value ($X_1$) measured from the plurality of detecting electrodes (active electrodes) 551, which serve as subject electrodes, which serve as subject electrodes to be determined, and the mean current value ($X_{nc}$) measured from the corresponding plurality of control electrodes 553, and then stores the mean current values ($X_1$, $X_{nc}$) in the mean-value/standard deviation memory 360.

(b) Furthermore, in step S342, the presence judgement module 330 calculates the standard deviation ($\sigma_1$) of the current values measured from the plurality of detecting electrodes (active electrodes) 551, which serve as subject electrodes, which serve as subject electrodes to be determined, and the standard deviation ($\sigma_{nc}$) of the current values measured from the corresponding control electrode 553, and then stores the standard deviation ($\sigma_1$, $\sigma_{nc}$) in the mean-value/standard deviation memory 360.

(c) Next, in step S343, it is determined if there are any data abnormalities due to device (hardware) failure. That is, the presence judgement module 330 reads out the predetermined parameter MSL from the MSL memory 365. The parameter MSL, as shown with horizontal dashed lines in FIGS. 23A-23C and FIGS. 23D-23F, is determined to be a relatively small value, for example, a current value in a range of 0-100 nA. The parameter MSL is predetermined and stored in the MSL memory 365. In step S343, the presence judgement module 330 reads out the mean current value $X_1$ measured by the plurality of detecting electrodes 551, which serve as subject electrodes to be determined, and the mean current value $X_{nc}$ of the corresponding control electrodes 553 from the mean-value/standard deviation memory 360 in order to confirm if each value is larger than the parameter MSL. In step S343, if at least one of the mean current value $X_1$ measured by the plurality of detecting electrodes 551, which serve as subject electrodes to be determined, and the mean current value $X_{nc}$ of the corresponding control electrodes 553 is lower than the parameter MSL, it is determined as a measurement abnormality due to device (hardware) failure. Therefore, the presence judgement module 330 does not determine the type. As shown in FIG. 25D, in step S435, the determination result is sorted and stored in the classified result storing unit 369, the display unit 306 displays "not determined (hardware error)" to show that the type cannot be determined. FIG. 23F shows, as a mode F, a distribution of the equivalent current values $I_{pk2}$ when the mean current value $X_1$ of the SNP1 detecting electrode (SNP="G" detecting electrode) 551 is smaller than the parameter MSL. The SNP1 detecting electrode (SNP="G" detecting electrode) 551 of FIG. 23F can replace the plurality of detecting electrodes 551, which serve as subject electrodes for determining the presence of a certain nucleic acid by the flowchart shown in FIG. 25B.

(d) In step S343, if both the mean current value $X_1$ measured by the plurality of detecting electrodes 551, which serve as subject electrodes to be determined, and the mean current value $X_{nc}$ of the corresponding control electrodes 553 are more than the parameter MSL, the determination procedure goes to step S344. The presence judgement module 330 next reads out the standard deviation ($\sigma_{nc}$) of the current values measured by the control electrodes 553 corresponding to the standard deviation ($\sigma_1$) of the current values measured by the detecting electrodes (active electrodes) 551 from the mean-value/standard deviation memory 360 to calculate the sum ($\sigma_1+\sigma_{nc}$) of the standard deviation ($\sigma_1$) of the current values measured by the detecting electrodes (active electrodes) 551 and the standard deviation ($\sigma_{nc}$) of the current values measured by the control electrodes 553. Then in step S344, the presence judgement module 330 confirms if the sum of the standard deviation $(\sigma_1+\sigma_{nc})$ is "zero". When the sum of the standard deviation $(\sigma_1+\sigma_{nc})$ is "zero," the calculation for the next step S345 cannot be performed. Therefore, in step S351, the determination result is sorted and stored in the classified result storing unit 369, and the subject nucleic acid shows that it is "not automatically determined" in the display unit 306. In step S341, when the sum of the standard deviation $(\sigma_1+\sigma_{nc})$ is not "zero," the presence judgement module 330 stores the difference in the mean-values $(X_1-X_{nc})$ and the sum of the standard deviation $(\sigma_1+\sigma_{nc})$ in the mean-value/standard deviation memory 360, and goes to step S345.

(e) In step S345, the presence judgement module 330 reads out the mean current value $(X_1)$ measured by the plurality of detecting electrodes 551, which serve as subject electrodes to be determined, and the mean current value $(X_{nc})$ of the corresponding control electrodes 553 from the mean-value/standard deviation memory 360 to calculate the difference $(X_1-X_{nc})$ of the mean current value $(X_1)$ of the detecting electrodes 551, which serve as subject electrodes to be determined, from the mean current value $(X_{nc})$ of the control electrodes 553. Furthermore, the presence judgement module 330, in step S345, reads out the sum of the standard deviation $(\sigma_1+\sigma_{nc})$ from the mean-value/standard deviation memory 360 to calculate the ratio $(X_1-X_{nc})/(\sigma_1+\sigma_{nc})$ of the difference in the mean-values $(X_1-X_{nc})$ to the sum of the standard deviation $(\sigma_1+\sigma_{nc})$. Then, the presence judgement module 330 stores the ratio $Y_1$ of the difference in the mean-values to the sum of the standard deviation:

$$Y_1=(X_1-X_{nc})/(\sigma_1+\sigma_{nc}) \qquad (7)$$

in the mean-value/standard deviation memory 360, and goes to step S346.

(f) In step S346, the presence judgement module 330 reads out the difference in the mean-values $(X_1-X_{nc})$ from the mean-value/standard deviation memory 360 as well as the signal-increment criterion SLL (+/−) from the SLL memory 362. Next, in step S346, the size is compared between the difference in the mean-values $(X_1-X_{nc})$ and the signal-increment criterion SLL (+/−). When the difference in the mean-values $(X_1-X_{nc})$ is lower than the signal-increment criterion SLL (+/−) in step S346, it is determined that the current values of the electrochemical currents for the subject nucleic acid were not observed from the detecting electrodes (active electrodes) 551. In step S350, the determination result is sorted and stored in the classified result storing unit 369, and the display unit 306 displays the determination of "−(none)" or "−(under the detection sensitivity)". On the other hand, in step S346, when the difference in the mean-values $(X_1-X_{nc})$ is larger than the signal-increment criterion SLL (+/−), the determination procedure goes to step S347.

(g) In step S347, the presence judgement module 330 reads out the ratio of the difference in the mean-values and the sum of the standard deviation $Y_1=(X_1-X_{nc})/(\sigma_1+\sigma_{nc})$ from the mean-value/standard deviation memory 360 as well as the effective scale factor ESLL from the ESLL memory 363. In step S347, the size is compared between the ratio $Y_1=(X_1-X_{nc})/(\sigma_1+\sigma_{nc})$ of the difference in the mean-values and the sum of the standard deviation to the effective scale factor ESLL. When the ratio $Y_1$ is determined to be smaller than the effective scale factor ESLL, the presence of the subject nucleic acid is determined to be "not clear." In step S349, the determination result is sorted and stored in the classified result storing unit 369, and the display unit 306 displays a determination of "not clear." On the other hand, in step S347, when the ratio $Y_1$ is larger than the effective scale factor ESLL, the subject nucleic acid is determined to be "clearly" present. In step S348, the determination result is sorted and stored in the classified result storing unit 369, and the display unit 306 displays "+(OK)." In step S346, when the difference in the mean-values $(X_1-X_{nc})$ is larger than the signal-increment criterion SLL (+/−), the determination is estimated as "+(OK)"; however, the indication "+(OK)" is not immediately shown. In step S347, it is determined whether there are dispersion in the current data.

[Step S105-2: Determination of SNP Type]

In step S332 of FIG. 25A, when it is determined to go to the flow of genotyping algorithm for determining which of two, SNP="G" or SNP="T" the SNP type is; furthermore for determining whether it is G/G homo-type, G/T hetero-type, or T/T homo-type, the typing module 340 makes a determination according to the procedure of a flowchart shown in FIG. 25C and FIG. 25D.

Figure 23A:
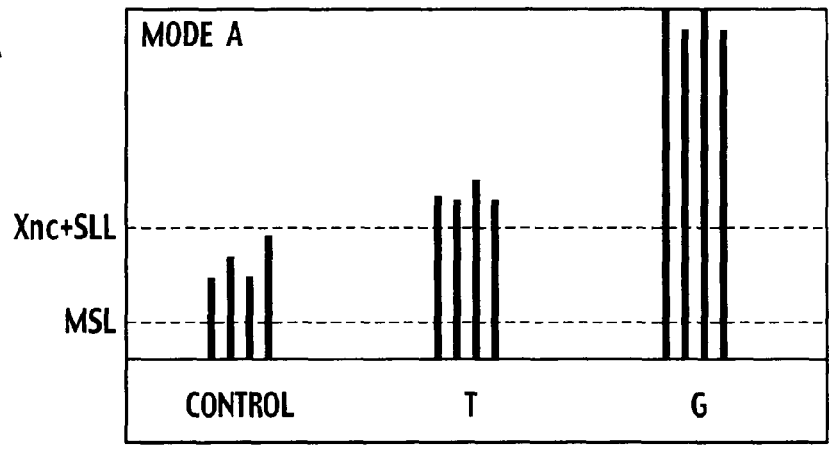
FIG. 23A is a collective bar graph showing mode A, as one of the sorted determination modes of the net detected signals (peak current values) obtained by the method shown in FIG. 22, sorted with multiple control electrodes, multiple SNP2 detecting electrodes (SNP="T" detecting electrodes) and multiple SNP1 detecting electrodes (SNP="G" detecting electrodes) respectively, mode A is a standard detection mode.
Figure 23B:
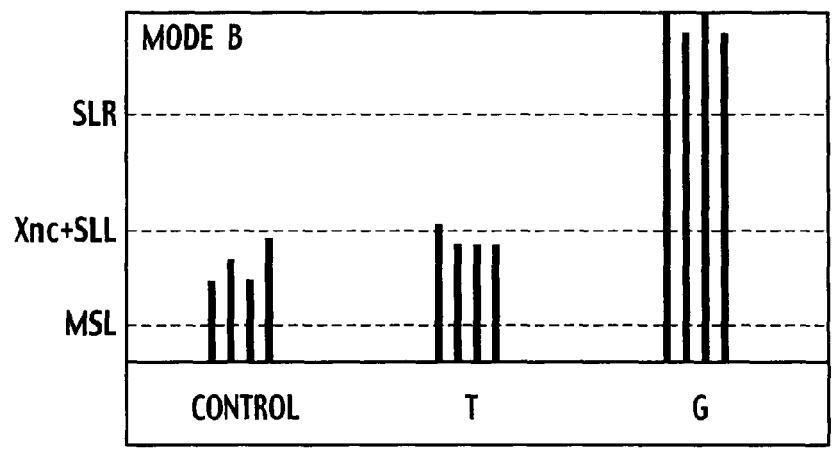
FIG. 23B is a collective bar graph showing mode B, as one of the sorted determination modes of the net detected signals (peak current values) obtained by the method shown in FIG. 22, sorted with multiple control electrodes, multiple SNP2 detecting electrodes (SNP="T" detecting electrodes) and multiple SNP1 detecting electrodes (SNP="G" detecting electrodes) respectively, mode B is an example of a detection mode in the case where there is an unusually weak signal from detecting electrodes SNP2.
Figure 23C:
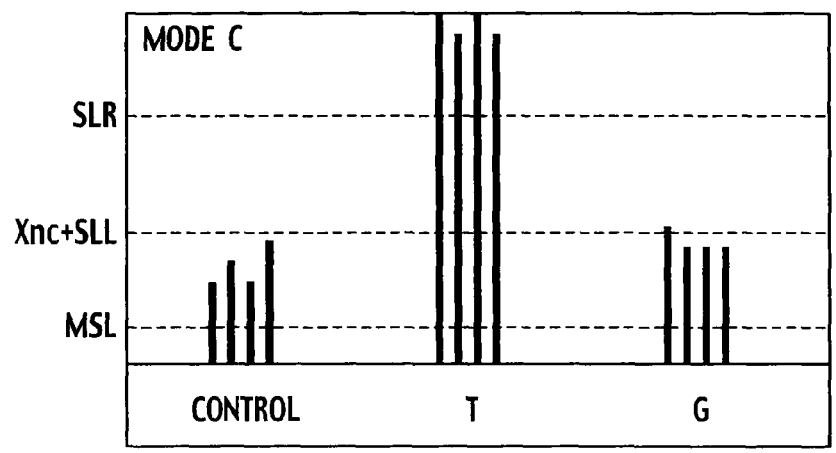
FIG. 23C is a collective bar graph showing mode C, as one of the sorted determination modes of the net detected signals (peak current values) obtained by the method shown in FIG. 22, sorted with multiple control electrodes, multiple SNP2 detecting electrodes (SNP="T" detecting electrodes) and multiple SNP1 detecting electrodes (SNP="G" detecting electrodes) respectively, mode C is an example of a detection mode in the case where there is an unusually weak signal from detecting electrodes SNP1.
Figure 23D:
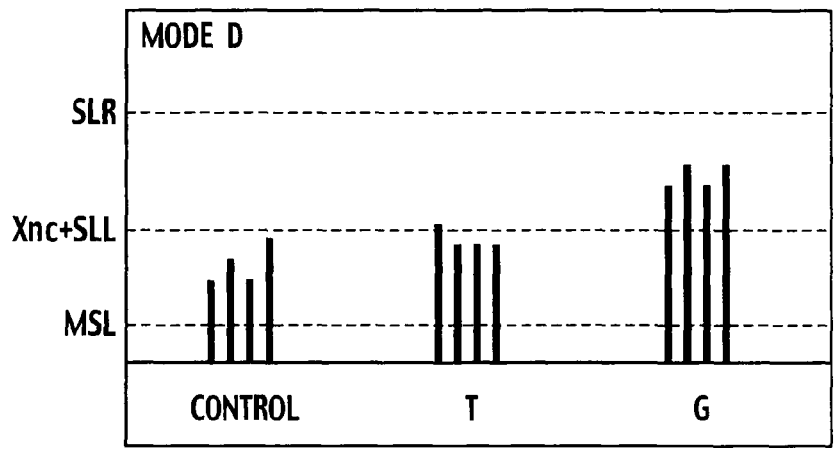
FIG. 23D is a collective bar graph showing mode D, as one of the sorted determination modes of the net detected signals (peak current values) obtained by the method shown in FIG. 22, classified into multiple control electrodes, multiple SNP2 detecting electrodes and multiple SNP1 detecting electrodes respectively, the data of mode D are excluded as abnormal data, because the signal from detecting electrodes SNP1 and detecting electrodes SNP2 are too weak and cannot be employed for determine the nucleotide sequence, the detecting electrodes SNP1 and SNP2 serve as subject electrodes to be determined.
Figure 23E:
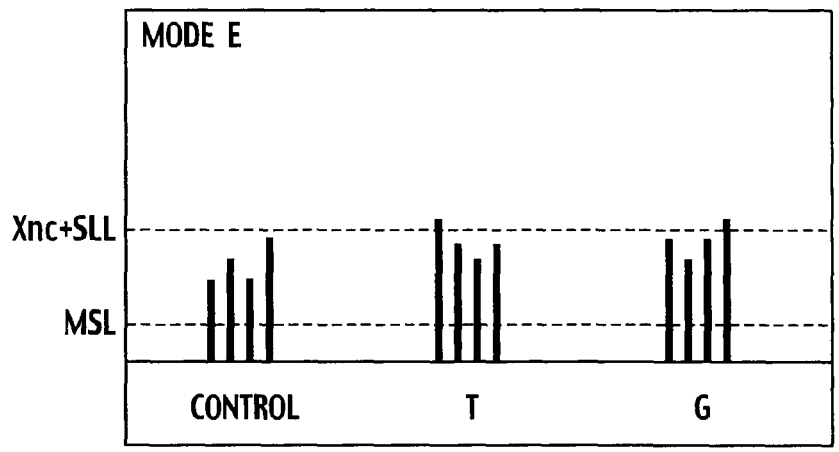
FIG. 23E is a collective bar graph showing mode E, as one of the sorted determination modes of the net detected signals (peak current values) obtained by the method shown in FIG. 22, classified into multiple control electrodes, multiple SNP2 detecting electrodes and multiple SNP1 detecting electrodes respectively, the data of mode E are excluded as abnormal data, because the signal from detecting electrodes SNP1 and detecting electrodes SNP2 are even weaker than in mode D, and, at the biological level, cannot be employed for determine the nucleotide sequence, the detecting electrodes SNP1 and SNP2 serve as subject electrodes to be determined.
Figure 23F:
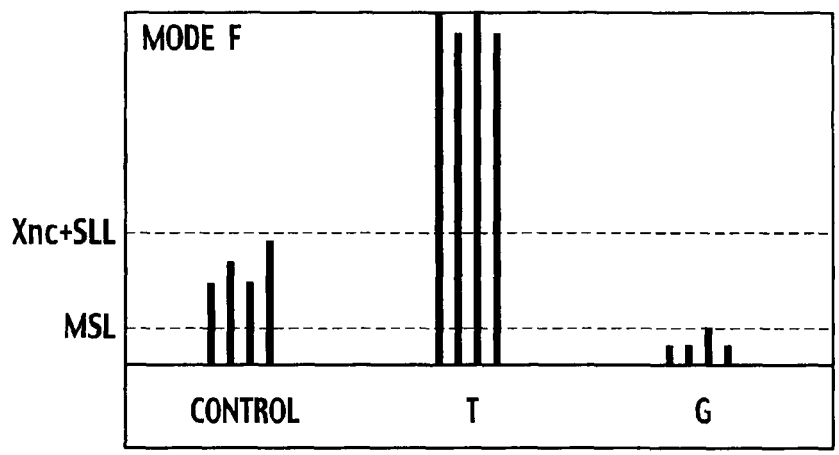
FIG. 23F is a collective bar graph showing mode F, as one of the sorted determination modes of the net detected signals (peak current values) obtained by the method shown in FIG. 22, classified into multiple control electrodes, multiple SNP2 detecting electrodes and multiple SNP1 detecting electrodes respectively, the data of mode F are excluded as abnormal data, because the signal from detecting electrodes SNP1 is too weak and is assumed to be under hardware problems.

Modes A-F shown in FIGS. 23A-23C and FIGS. 23D-23F, show classifications of representative examples (modes) of detection signals determined by the typing module 340 according to the procedure of a flowchart shown in FIG. 25C and FIG. 25D. Mode A shown in FIG. 23A is a standard detection mode, while mode B shown in FIG. 23B is a detection mode showing a sample in which intentional signal increase cannot be expected, since the signals from the SNP2 detecting electrodes (SNP="T" detecting electrodes) 552 are too small. On the other hand, mode C shown in FIG. 23C is a detection mode showing a sample in which intentional signal increase cannot be expected, since the signals from the SNP1 detecting electrodes (SNP="G" detecting electrodes) 551 are too small, the detecting electrodes 551 serve as subject electrodes to be determined, at a biological level.

In addition, mode D shown in FIG. 23D is a detection mode to be eliminated as abnormal data, since both the signals from the SNP1 detecting electrodes (SNP="G" detecting electrodes) 551 and the signals from the SNP2 detecting electrodes (SNP="T" detecting electrodes) 552 are too small, the detecting electrodes 551 and 552 serve as subject electrodes to be determined. In addition, mode E shown in FIG. 23E is a detection mode to be eliminated as abnormal data, since both the signals from the SNP1 detecting electrodes (SNP="G" detecting electrodes) 551 and the signals from the SNP2 detecting electrodes (SNP="T" detecting electrodes) 552 are smaller than mode D and, thus, are not determined at a biological level. In addition, mode F shown in FIG. 23F is a detection mode to be eliminated as abnormal data, since the signals from the SNP1 detecting electrodes (SNP="G" detecting electrodes) 551 are abnormally small; on the other hand, the signals from the SNP2 detecting electrodes (SNP="T" detecting electrodes) 552 are abnormally large, which is assumed to be a hardware problem.

The typing module 340, for example, determines whether the base at a certain SNP position is G/G homo-type, G/T hetero-type, or T/T homo-type, while classifying in modes A-F and the like shown in FIGS. 23A-23C and FIGS. 23D-23F.

(a) First, the typing module 340, in step S361, determines whether the target number is two pieces or not. In this case, it intends to determine between the two types of SNP="G" and SNP="T". Therefore, if the target number is zero, a single piece, three pieces, and the like, it means that the initial setting itself is wrong. In that case, as shown in FIG. 25D, in step S436, the determination result is sorted and stored in the classified result storing unit 369, and the display unit 306 displays "setting error."

(b) In step S361, when the target number is determined to be two pieces, the typing module 340 goes to step S362. In step S362, the typing module 340 calculates the mean current value $X_1$ of the SNP1 detecting electrodes (SNP="G" detecting electrodes) 551, the mean current value $X_{nc1}$ of the control electrodes (NC1) 553 corresponding to the SNP1 detecting electrodes 551, the mean current value $X_2$ of the SNP2 detecting electrodes 552, and the mean current value $X_{nc2}$ of the control electrodes (NC2) 553 corresponding to the SNP2 detecting electrodes 552.

FIG. 2 shows the common control electrodes 553 corresponding to both the SNP1 detecting electrodes 551 and the SNP2 detecting electrodes 552. However, it is possible to set a control electrodes (NC1) corresponding to the SNP1 detecting electrodes 551 and a control (NC2) corresponding to the SNP2 detecting electrodes 552 separately. The mean current value $X_1$ calculated from measurement by the SNP 1 detecting electrodes 551, the mean current value $X_{nc1}$ calculated from measurement by the control electrodes (NC1) 553 corresponding to the SNP1 detecting electrodes 551, the mean current value $X_2$ calculated from measurement by the SNP2 detecting electrodes 552, and the mean current value $X_{nc2}$ calculated from measurement by the control (NC2) electrodes 553 corresponding to the SNP2 detecting electrodes 552 are sorted and stored in the mean-value/standard deviation memory 360.

(c) In step S363, the typing module 340 calculates the standard deviation $\sigma_1$ of the current values measured from the SNP1 detecting electrodes 551, the standard deviation $\sigma_{nc1}$ of the control electrodes (NC1) 553 corresponding to the current values for the SNP1 detecting electrodes 551, the standard deviation $\sigma_2$ of the current values measured from the SNP2 detecting electrodes 552, and the standard deviation $\sigma_{nc2}$ from the control electrodes (NC2) 553 corresponding to the current values for the SNP2 detecting electrodes 552.

(d) Next, the typing module 340 reads out the parameter MSL from the MSL memory 365. The parameter MSL, as shown with a dashed line in FIGS. 23A-23C and FIGS. 23D-23F, is to be set as a current value at a relatively small value, for example, within a range of 0-100 nA. The parameter MSL is predetermined and stored in the MSL memory 365. In step S364, the typing module 340 reads out the mean current value $X_1$ from the SNP1 detecting electrodes 551, the mean current value $X_{nc1}$ from the control electrodes (NC1) 553 corresponding to the SNP1 detecting electrodes 551, the mean current value $X_2$ from the SNP2 detecting electrodes 552, and the mean current value $X_{nc2}$ from the control (NC2) electrodes 553 corresponding to the SNP2 detecting electrodes 552 in order, and confirms if each value is larger than the parameter MSL. In step S364, when at least one of the mean current value $X_1$ from the SNP1 detecting electrodes 551, the mean current value $X_{nc1}$ from the control electrodes (NC1) 553 corresponding to the SNP1 detecting electrodes 551, the mean current value $X_2$ from the SNP2 detecting electrodes 552, and the mean current value $X_{nc2}$ from the control (NC2) electrodes 553 corresponding to the SNP2 detecting electrodes 552, is lower than the parameter MSL, it is considered as a measurement abnormality due to device (hardware) failure. Therefore, a determination of type is not conducted. As shown in FIG. 25D, in step S435, the determination result is sorted and stored in the classified result storing unit 369, and the display unit 306 displays "Not determined (hardware error)" to indicate that the type cannot be determined. FIG. 23F shows an example of mode F, in which the distribution of the equivalent current values $I_{pk2}$ corresponds to a case that the mean current value $X_1$ of the SNP1 detecting electrodes (SNP="G" detecting electrodes) is smaller than the parameter MSL.

(e) Next, the typing module 340 reads out the signal-increment criterion SLL from the SLL memory 362. The SLL (M) is a predetermined parameter that provides selection criterion for the determination genotyping algorithm of the signal increase to the control electrodes 553. The typing module 340, in step S365, from the mean-value/standard deviation memory 360, reads out the mean current value $X_{nc1}$ from the control electrodes (NC1) 553 corresponding to the mean current value $X_1$ calculated from measurement by the SNP1 detecting electrodes 551, the difference ($X_1-X_{nc1}$) of the mean current value $X_1$ calculated from measurement by the SNP1 detecting electrodes 551, and the mean-value $X_{nc1}$ calculated from measurement by the control electrodes (NC1) 553. Then, the size is compared to that of the signal-increment criterion SLL (M), and the difference ($X_1-X_{nc1}$) of the mean current values measured by the SNP1 detecting electrodes 551 side is sorted and stored in the mean-value/standard deviation memory 360. In addition, the typing module 340, in step S365, reads out the mean current value $X_{nc2}$ calculated from measurement by the control electrodes (NC2) 553 corresponding to the mean current value $X_2$ calculated from measurement by the SNP2 detecting electrodes 552 from the mean-value/standard deviation memory 360 to calculate the difference ($X_2-X_{nc2}$) between the mean current value $X_2$ calculated from measurement by the SNP2 detecting electrodes 552 and the mean current value $X_{nc2}$ calculated from measurement by the control electrodes (NC2) 553. The size is compared to that of the signal-increment criterion SLL (M), and the difference ($X_2-X_{nc2}$) in the mean-values measured by the SNP1 detecting electrodes 551 side is sorted and stored in the mean-value/standard deviation memory 360. In step S365, when both the difference ($X_2-X_{nc2}$) in the mean-values measured by the SNP1 detecting electrodes 551 side (signal increase) and the difference ($X_2-X_{nc2}$) in the mean-values measured by the SNP2 detecting electrodes 552 side are smaller than the criterion SLL (M), some abnormalities may occur in the chip or the sample (biological sample). As shown in FIG. 25D, in step S434, the determination result is sorted and stored in the classified result storing unit 369, and the display unit 306 displays "Not determined (bio sample error)" to indicate that the type cannot be determined. FIG. 23E, as mode E, shows a distribution of the equivalent current values $I_{pk2}$ when both the difference ($X_2-X_{nc2}$) in the mean-values measured by the SNP1 detecting electrodes 551 side (signal increase) and the difference ($X_2-X_{nc2}$) in the mean-values measured by the SNP2 detecting electrodes 552 side are smaller than the criterion SLL (M). In step S365, when at least one of the difference ($X_2-X_{nc2}$) in the mean-values measured by the SNP1 detecting electrodes 551 side (signal increase) and the difference ($X_2-X_{nc2}$) in the mean-values measured by the SNP2 detecting electrodes 552 side is larger than the criterion SLL (M), the determination procedure goes to step S366.

(f) The typing module 340, in step S366, reads out the signal-increment criterion SLL (M) from the SLL memory 362 to compare the difference in the mean-values ($X_2-X_{nc2}$) as well as the size with the signal-increment criterion SLL (M). When the difference in the mean-values ($X_2-X_{nc2}$) at the SNP2 detecting electrodes 552 side is smaller than the signal-increment criterion SLL (M), it means that only the difference in the mean-values ($X_2-X_{nc2}$) at the SNP1 detecting electrodes 551 side is larger than the criterion SLL (M), and it is a candidate to be a homo-type of the SNP1 base (G). Therefore, the determination procedure goes to step S371. In step S366, when the difference in the mean-values ($X_2-X_{nc2}$) at the SNP2 detecting electrodes 552 side is larger than the signal-increment criterion SLL (M), the determination procedure goes to step S367.

(g) The typing module 340, in step S367, reads out the difference in the mean-values ($X_1-X_{nc1}$) at the SNP1 detecting electrodes 551 side from the mean-value/standard deviation memory 360 to compare the difference in the mean-values ($X_1-X_{nc1}$) as well as the size relation to the signal-increment criterion SLL (M). When the difference in the mean-values ($X_1-X_{nc1}$) is smaller than the signal-increment criterion SLL (M), it means that only the difference in the mean-values measured by the SNP2 detecting electrodes 552 side ($X_2-X_{nc2}$) is larger than the criterion SLL (M) and it is a candidate for the homo-type of SNP2 base (T). Therefore, the determination procedure goes to step S373. In step S367, when the difference in the mean-values ($X_2-X_{nc2}$) is larger than the signal-increment criterion SLL (M), it means that both the difference in the mean-values ($X_1-X_{nc1}$) at the SNP1 detecting electrodes 551 side and the difference in the mean-values ($X_2-X_{nc2}$) at the SNP2 detecting electrodes 552 side are larger than the criterion SLL (M). Therefore, the determination procedure goes to step S368 to determine if it is homo-type or hetero-type.

(h) The typing module 340 reads out the difference in the mean-values ($X_2-X_{nc2}$) at the SNP2 detecting electrodes 552 side from the mean-value/standard deviation memory 360, and in step S368, calculates the ratio ($X_1-X_{nc1}$)/($X_2-X_{nc2}$) of the difference in the mean-values ($X_1-X_{nc1}$) at the SNP1 detecting electrodes 551 side to the difference in the mean-values ($X_2-X_{nc2}$) at the SNP2 detecting electrodes 552 side. Furthermore, in step S368, the typing module 340 calculates R-value, the R-value is defined as a $\text{Log}_{10}$ of the absolute value for the ratio ($X_1-X_{nc1}$)/($X_2-X_{nc2}$) as follows:

$$R=\text{Log}_{10}(\text{abs}((X_1-X_{nc1})/(X_2-X_{nc2}))) \qquad (8)$$

The typing module 340 stores the calculated R-value in the logarithm-of-absolute-value memory 367, and goes step S368.

(i) The typing module 340, in step S369, the mean current value $Xnc_1$ calculated from measurement by the control electrodes (NC1) 553 corresponding to the SNP1 detecting electrodes 551 is defined as $X_{cmp1}$, the mean current value $Xnc_2$ calculated from measurement by the control electrodes (NC2) 553 corresponding to the SNP2 detecting electrodes 552 is defined as $X_{cmp2}$. The typing module 340 stores the mean current value $Xnc_1$ and $Xnc_2$ in the mean-value/standard deviation memory 360. Furthermore, the standard deviation $\sigma nc_1$ of the current values, which is calculated from measurement by the control electrodes (NC1) 553 corresponding to the SNP1 detecting electrodes 551, is defined as $\sigma_{cmp1}$, and the standard deviation $\sigma nc_2$ of the current values, which is calculated from measurement by the control electrodes (NC2) 553 corresponding to the SNP2 detecting electrodes 552, is defined as $\sigma_{cmp2}$. The typing module 340 stores each value $\sigma nc_1$ and $\sigma nc_2$ in the mean-value/standard deviation memory 360, and goes to step S401. The typing module 340 reads out the first homo-typing criterion (+HLL) with respect to the logarithm of signal ratio from the HLL memory 368, and compares the size relation between the R-value and the first homo-typing criterion (+HLL) with respect to the logarithm of signal ratio in step S401. When the R-value is larger than the first homo-typing criterion (+HLL) with respect to the logarithm of signal ratio in step S401 (when it is determined to lie in an upper triangular area between the upper slashed line labeled as +HLL and ordinate in FIG. 26), SNP1 base (G) homo-type is estimated. Therefore, the determination procedure goes to step S402. In step S401, when the R-value is smaller than the first homo-typing criterion (+HLL) with respect to the logarithm of signal ratio, the determination procedure goes to step S411. In step S411, the size relation between the R-value and the second homo-typing criterion (−HLL) with respect to the logarithm of signal ratio is compared. When the R-value is determined to be smaller than the second homo-typing criterion (−HLL) with respect to the logarithm of signal ratio (when it is determined to lie in lower triangular area between the lower slashed line labeled as −HLL and abscissa in FIG. 26), SNP2 base (T) homo-type is estimated. Therefore, the determination procedure goes to step S412. In step S411, the R-value is larger than the second homo-typing criterion (−HLL) with respect to the logarithm of signal ratio, that is, the R-value is determined to be between the second homo-typing criterion (−HLL) and the first homo-typing criterion (+HLL), it will be a candidate for SNP1/SNP2, that is, G/T hetero-type. Therefore, the determination procedure goes to step S421. In step S421, the hetero-typing criterion HUL with respect to the logarithm signal ratio is read out from the HUL memory 364 to compare the size relation between the absolute value of the R-value and the hetero-typing criterion HUL with respect to the logarithm signal ratio. In step S421, when the absolute value of the R-value is determined to be lower than the hetero-typing criterion HUL with respect to the logarithm signal ratio (when it is determined to lie in the central rhombic area between two slash lines labeled with HULs in FIG. 26), a hetero-type of SNP1/SNP2 is estimated. Therefore, the determination procedure goes to step S422. In step S421, when the absolute value of the R-value is determined to be larger than the hetero-typing criterion HUL with respect to the logarithm signal ratio (when it is determined to be outside of the central rhombic area between two slash lines labeled with HULs in FIG. 26), as shown in FIG. 25D, in step S430, the determination result is sorted and stored in the classified result storing unit 369, and the display unit 306 displays "not automatically determined (homo or hetero)" to indicate that the type cannot be determined.

(j) Now step S371 will be explained. As mentioned above, in step S366, when the difference in the mean-values measured by the SNP2 detecting electrodes 552 side ($X_2-X_{nc2}$) is smaller than the signal-increment criterion SLL (M), a homo-type of the SNP1 base (G) is a candidate. Therefore, the determination procedure goes to step S371. The typing module 340, in step S371, defines the mean current value $X_2$ calculated from measurement by the SNP2 detecting electrodes 552 as $X_{cmp1}$ and the standard deviation $\sigma_2$ of the current values measured by the SNP2 detecting electrodes 552 as $\sigma_{cmp1}$. The typing module 340 stores each value in the mean-value/standard deviation memory 360, and goes to step S372. In step S372, the typing module 340 reads out the purposive scale-factor SLR. Furthermore, the typing module 340 reads out the mean-value $X_1$ of the current values measured from the SNP1 detecting electrodes 551 and $X_{cmp1}$ from the mean-value/standard deviation memory 360, and the ratio of the mean-value $X_1$ and the mean-value $X_{cmp1}$ (=magnification $X_1/X_{cmp1}$) is calculated to compare with the purposive scale-factor SLR. When the ratio of the mean-value $X_1/X_{cmp1}$ is lower than the purposive scale-factor SLR in step S372, the current increase in the SNP1 detecting electrodes 551 is determined to be insufficient. As shown in FIG. 25D, in step S433, the determination result is sorted and stored in the classified result storing unit 369, and the display unit 306 displays "not determined (small signal)" to indicate that the type cannot be determined. FIG. 23D shows an example of mode D, in which the distribution of the equivalent current values $I_{pk2}$ corresponds to a case that the current increase in the SNP1 detecting electrodes (SNP="G" detecting electrodes) 551 is insufficient. In step S372, when the ratio of the mean-value $X_1/X_{cmp1}$ is larger than the purposive scale-factor SLR, a homo-type of the SNP1 base (G) is estimated. Therefore, the determination procedure goes to step S402. It is also significant to compare with the mean current value $X_{nc1}$ calculated from measurement by the control electrodes (NC1) 553. Briefly, in the case of SNP1 base (G) homo-type, the size of $X_1/X_{nc1}$ can be compared with that of the purposive scale-factor SLR.

(k) Next, step S373 will be explained. As mentioned above, in step S367, when the difference $(X_1-X_{nc1})$ in the mean-values measured by the SNP1 detecting electrodes 551 side is smaller than the signal-increment criterion SLL (M), it will be a candidate for SNP2 base (T) homo-type. Therefore, the determination procedure goes to step S373. In step S373, the mean current value $X_1$ calculated from measurement by the SNP1 detecting electrodes 551 is defined as $X_{cmp2}$, and the standard deviation $\sigma_1$ of the current values measured from the SNP1 detecting electrodes 551 is defined as $\sigma_{cmp2}$. The typing module 340 stores each value in the mean-value/standard deviation memory 360, and goes to step 374. In step S374, the typing module 340 reads out the purposive scale-factor SLR from the SLR memory 366. In addition, the typing module 340 reads out the mean current value $X_2$ calculated from measurement by the SNP2 detecting electrodes 552 and $X_{cmp2}$ determined in step S371 so as to calculate the ratio (=magnification) of the mean-value $X_2$ against to the mean-value $X_{cmp2}$ ($X_2/X_{cmp2}$) to compare with the purposive scale-factor SLR. In step S374, when the ratio $X_2/X_{cmp2}$ of the mean-values is smaller than the purposive scale-factor SLR in step S374, the current increase in the SNP2 detecting electrodes 552 is determined to be insufficient. As shown in FIG. 25D, in step S433, the determination result is sorted and stored in the classified result storing unit 369, and the display unit 306 displays "not determined (small signal)" to show that the type cannot be determined. When the ratio $X_2/X_{cmp2}$ of the mean-values is larger the purposive scale-factor SLR in step S374, a homo-type of SNP2 base (T) is estimated. Therefore, the determination procedure goes to step S412. In step S372, the mean current value $X_2$ calculated from measurement by the SNP2 detecting electrodes 552 is compared with $X_{cmp2}$ ($X_1$); however, it is significant to compare with the mean current value $X_{nc2}$ calculated from measurement by the control electrodes (NC2) 553. That is, in the case of SNP2 base (T) homo-type candidate, the size of $X_2/X_{cmp2}$ can be compared with that of the purposive scale-factor SLR.

(l) Now, step S402 will be explained. For the typing module 340, in step S402, the sum of the standard deviation $(\sigma_1)$ of the current values measured from the SNP1 detecting electrodes 551 and the standard deviation $(\sigma_{cmp1})$ of the current values to be compared $(\sigma_1+\sigma_{cmp1})$ is calculated. Furthermore, in step S402, the typing module 340 confirms whether the sum of the standard deviations $(\sigma_1+\sigma_{cmp1})$ is not "zero." When the sum of the standard deviations $(\sigma_1+\sigma_{cmp1})$ is "zero," the calculation in the next step S403 cannot be conducted. Therefore, in step S406, the determination result is sorted and stored in the classified result storing unit 369, and the display unit 306 displays "not automatically determined." In step S402, if the sum of the standard deviations $(\sigma_1+\sigma_{cmp1})$ is not "zero", the determination procedure goes to step S403.

(m) In step S403, the typing module 340 reads out the difference of the mean-values $(X_1-X_{cmp1})$ from the mean-value/standard deviation memory 360 to calculate the ratio $(X_1-X_{cmp1})/(\sigma_1+\sigma_{cmp1})$ of the difference in the mean-values $(X_1-X_{cmp1})$ to the sum of the standard deviations $(\sigma_1+\sigma_{cmp1})$. The typing module 340 stores the ratio $Y_1$ of the difference in the mean-values to the sum of the standard deviations:

$$Y_1=(X_1-X_{cmp1})/(\sigma_1+\sigma_{cmp1}) \tag{9}$$

in the mean-value/standard deviation memory 360, and goes to step S404.

(n) In step S404, the typing module 340 reads out the ratio of the difference in the mean-values to the sum of the standard deviations $Y_1=(X_1-X_{cmp1})/(\sigma_1+\sigma_{cmp1})$ from the mean-value/standard deviation memory 360 as well as the effective scale factor ESLL from the ESLL memory 363. Then, in step S404, the ratio of the difference in the mean-values to the sum of the standard deviations $Y_1=(X_1-X_{cmp1})/(\sigma_1+\sigma_{cmp1})$ is compared with the effective scale factor ESLL regarding the size. In step S404, when the ratio is smaller than the effective scale factor ESLL, the presence of SNP1 base homo-type is determined to be "not clear." In step S407, the determination result is sorted and stored in the classified result storing unit 369, and the display unit 306 displays the determination of "G/G homo not clear". On the other hand, in step S404, when the ratio is larger than the effective scale factor ESLL, the homo-type of SNP1 base (G) is determined to "clearly" exist. In step S405, the determination result is sorted and stored in the classified result storing unit 369, and the display unit 306 displays an indication of "G/G homo OK".

(o) Next, step S412 will be explained. The typing module 340, in step S412, reads out the standard deviation $(\sigma_2)$ of the current values measured by the SNP2 detecting electrodes 552 and the standard deviation $(\sigma_{cmp2})$ of the corresponding current values to be compared that is determined in step S369 from the mean-value/standard deviation memory 360. The sum $(\sigma_2+\sigma_{cmp2})$ of the standard deviation $(\sigma_2)$ of the current values measured by the SNP2 detecting electrodes 552 and the standard deviation $(\sigma_{cmp2})$ of the current values to be compared is then calculated. Furthermore, in step S412, when the sum of the standard deviation $(\sigma_2+\sigma_{cmp2})$ is "zero," the calculation in the next step S413 cannot be conducted. Therefore, in step S416, the determination result is sorted and stored in the classified result storing unit 369, and the display unit 306 displays that it is "not automatically determined." In step S412, if the sum of the standard deviation $(\sigma_2+\sigma_{cmp2})$ is not "zero," the determination procedure goes to step S413.

(p) In step S413, the typing module 340 reads out the difference in the mean-values $(X_2-X_{cmp2})$ from the mean-value/standard deviation memory 360 to calculate the ratio $(X_2-X_{cmp2})/(\sigma_2+\sigma_{cmp2})$ of the difference in the mean-values $(X_2-X_{cmp2})$ to the sum of the standard deviations $(\sigma_2+\sigma_{cmp2})$. The typing module 340 stores the ratio $Y_2$ of the difference in the mean-values and the sum of the standard deviations:

$$Y_2=(X_2-X_{cmp2})/(\sigma_2+\sigma_{cmp2}) \tag{10}$$

in the mean-value/standard deviation memory 360, and goes to step S414.

(q) In step S414, the typing module 340 reads out the ratio of the difference in the mean-values to the sum of the standard deviations $Y_2=(X_2-X_{cmp2})(\sigma_2+\sigma_{cmp2})$ from the mean-value/standard deviation memory 360 as well as the effective scale factor ESLL from the ESLL memory 363. In step S414, the ratio of the difference in the mean-values to the sum of the standard deviations $Y_2=(X_2-X_{cmp2})/(\sigma_2+\sigma_{cmp2})$ is compared with the effective scale factor ESLL regarding the size. When the ratio is determined to be smaller than the effective scale factor ESLL in step S414, the determination result is sorted and stored in the classified result storing unit 369, and the display unit 306 displays the determination of "T/T homo not clear". On the other hand, in step S414, when the ratio is larger than the effective scale factor ESLL, a homo-type for the SNP2 base (T) is determined to exist. In step S415, the determination result is sorted and stored in the classified result storing unit 369, and the display unit 306 displays "T/T homo OK".

(r) Step S422 will be explained here. The typing module 340, in step S422, reads out the standard deviation $(\sigma_1)$ of the current values measured by the SNP1 detecting electrodes 551 and the standard deviation ($\sigma_{cmp1}$) of the corresponding current values to be compared that is determined in step S369 from the mean-value/standard deviation memory 360 to calculate the sum ($\sigma_1+\sigma_{cmp1}$) of the standard deviation ($\sigma_1$) of the peak current values measured from the SNP1 detecting electrodes 551 and the standard deviation ($\sigma_{cmp1}$) to be compared. Furthermore, in step S422, the typing module 340 confirms if the sum of the standard deviations ($\sigma_1+\sigma_{cmp1}$) is not "zero." When the sum of the standard deviations ($\sigma_1+\sigma_{cmp1}$) is "zero," the calculation in the next step S423 cannot be conducted. Therefore, in step S432, the determination result is sorted and stored in the classified result storing unit 369, and the display unit 306 displays that it is "not automatically determined." In step S422, if the sum of the standard deviations ($\sigma_1+\sigma_{cmp1}$) is not "zero", the determination procedure goes to step S423.

(s) In step S423, the typing module 340 reads out the difference in the mean-values ($X_1-X_{cmp1}$) from the mean-value/standard deviation memory 360 to calculate the ratio ($X_1-X_{cmp1}$)/($\sigma_1+\sigma_{cmp1}$) of the difference in the mean-values ($X_1-X_{cmp1}$) to the sum of the standard deviations ($\sigma_1+\sigma_{cmp1}$) (see Eq. (9)). The typing module 340 stores the ratio $Y_1$ of the difference in the mean-values to the sum of the standard deviations in the mean-value/standard deviation memory 360, and goes to step S424.

(t) In step S424, the typing module 340 reads out the standard deviation ($\sigma_2$) of the current values measured by the SNP2 detecting electrodes 552 and the standard deviation ($\sigma_{cmp2}$) of the corresponding current values to be compared that is determined in step S369 from the mean-value/standard deviation portion 360. The sum ($\sigma_2+\sigma_{cmp2}$) of the standard deviation ($\sigma_2$) of the current values measured by the SNP2 detecting electrodes 552 and the standard deviation ($\sigma_{cmp2}$) of the corresponding current values to be compared is then calculated. In step S424, the typing module 340 confirms if the sum of the standard deviations ($\sigma_2+\sigma_{cmp2}$) is not "zero." When the sum of the standard deviation is ($\sigma_2+\sigma_{cmp2}$) is "zero," the calculation in the next step S425 is not conducted. Therefore, in step S428, the determination result is sorted and stored in the classified result storing unit 369, and the display unit 306 displays that it is "not automatically determined." In step S424, if the sum ($\sigma_2+\sigma_{cmp2}$) of the standard deviation is not "zero," the determination procedure goes to step S425.

(u) In step S425, the typing module 340 reads out the difference in the mean-values ($X_2-X_{cmp2}$) from the mean-value/standard deviation memory 360 to calculate the ratio ($X_2-X_{cmp2}$)/($\sigma_2+\sigma_{cmp2}$) of the difference in the mean-values ($X_2-X_{cmp2}$) to the sum of the standard deviations ($\sigma_2+\sigma_{cmp2}$). The typing module 340 stores the ratio $Y_2$ of the difference in the mean-values and the sum of the standard deviation (see Eq. (10)) in the mean-value/standard deviation memory 360, and goes to step S426.

(v) In step S426, the typing module 340 reads out the ratio of the difference in the mean-values to the sum of the standard deviation $Y_1=(X_1-X_{cmp1})(\sigma_1+\sigma_{cmp1})$ from the mean-value/standard deviation memory 360 and the effective scale factor ESLL from the ESLL memory 363. Then, in step S426, the ratio of the difference in the mean-values to the sum of the standard deviation $Y_1=(X_1-X_{cmp1})/(\sigma_1+\sigma_{cmp1})$ is compared with the effective scale factor ESLL regarding the size. Furthermore, in step 426, the typing module 340 reads out the ratio of the difference in the mean-values and the sum of the standard deviations $Y_2=(X_2-X_{cmp2})/(\sigma_2+\sigma_{cmp2})$ from the mean-value/standard deviation memory 360. In step S426, the ratio of the difference in the mean-values and the sum of the standard deviation $Y_2=(X_2-X_{cmp2})/(\sigma_2+\sigma_{cmp2})$ is compared with the effective scale factor ESLL regarding the size relation. In step S426, when either $Y_1$ or $Y_2$ is determined to be smaller than the effective scale factor ESLL, the presence of the G/T hetero-type is determined to be "not clear." In step S429, the determination result is sorted and stored in the classified result storing unit 369, and the display unit 306 displays the determination of "G/T hetero not clear". On the other hand, in step S426, when both $Y_1$ and $Y_2$ are simultaneously more than the effective variant coefficient, the G/T hetero-type is determined to be "clearly" present, in step S427, the determination result is sorted and stored in the classified result memory 369, and the display unit 306 displays "G/T hetero OK"

As understood from above-mentioned explanation, according to the nucleotide sequence method associated with the embodiment of the present invention, even when there are abnormalities in the chip cartridge 11 and the detecting system 12, and when there is dispersion in data, it can be determined with high accuracy if a certain nucleic acid is present by excluding such abnormal data. In addition, according to the nucleotide sequence method associated with the embodiment of the present invention, if the initial setting has an error, it is determined to be a "setting error." If the chip or the sample (biological sample) has an abnormality, it is determined to be "not determined (bio sample error)." If there is a device (hardware) failure, these abnormal data can be eliminated by processing, such as determining as "not determined (hardware error)." In addition, when a determination cannot be made due to the dispersion in signals, when the signal strength is weak, or when it is unclear for other reasons, it is possible to make a determination depending on the conditions, such as "not clear," "not automatically determined (homo or hetero)," "not determined (small signal)," "not automatically determined," "'1/1 homo' not clear," "'2/2 homo' not clear," "'12 hetero' not clear" and the like. Therefore, according to the nucleotide sequence method associated with the embodiment of the present invention, it can be highly accurately determined what the SNP type is, such as "'1/1 homo' OK", "'2/2 homo' OK", "'12 hetero' OK" and the like, corresponding so as to be eligible to various measurement environments and situations (actual condition). Wherein, convenient descriptions such as "1" or "2" are shown as "A", "T", "G", "C" and the like in actuality.

Nucleotide Sequence Determination Program

A series of determination operations shown in FIG. 14, FIG. 16, FIGS. 18A-18B, FIGS. 23A-23F, FIG. 24, and FIGS. 25A-25D, by the program for genotyping algorithm equivalent to the FIG. 14, FIG. 16, FIGS. 18A-18B, FIGS. 23A-23F, FIG. 24, and FIGS. 25A-25D, the nucleotide sequence determination system shown in FIG. 8 can be controlled and executed. The program may be stored in the program memory (not shown) of a computer system that implements the nucleotide sequence determination system of the present invention. In addition, the program can perform a sequence of determination operations of the present invention. Wherein, "computer-readable recording medium" means a medium that can record programs, such as a computer external memory, semiconductor memory, magnetic disk, optical disk, magnet-optical (MO) disk, magnetic tape, and the like. More particularly, the "computer readable recording medium" contains a flexible disk, compact disk (CD)-read-only memory (ROM), cassette tape, open reel tape, memory card, hard disk, removable disk, and the like.

For example, the main body of the nucleotide sequence determination system can be implemented by a flexible disk drive and a optical disk drive or to externally connect with them. A flexible disk for the flexible disk drive and a CD-ROM for the optical disk drive are inserted from the insertion port. By performing a specific read-out operation, the program stored in these recording mediums can be installed in the program memory that implements the nucleotide sequence determination system. In addition, by connecting a specific drive unit, it is possible to use ROM as a memory that has been utilized for a game pack and the like or a cassette tape as a magnetic tape device. Furthermore, via an information-processing network including the internet and the like, the program can be stored in the program memory.

Other Embodiments

Various modifications will become possible for those skilled in the art after receiving the teaching of the present disclosure without departing from the scope thereof.

Figure 27A:
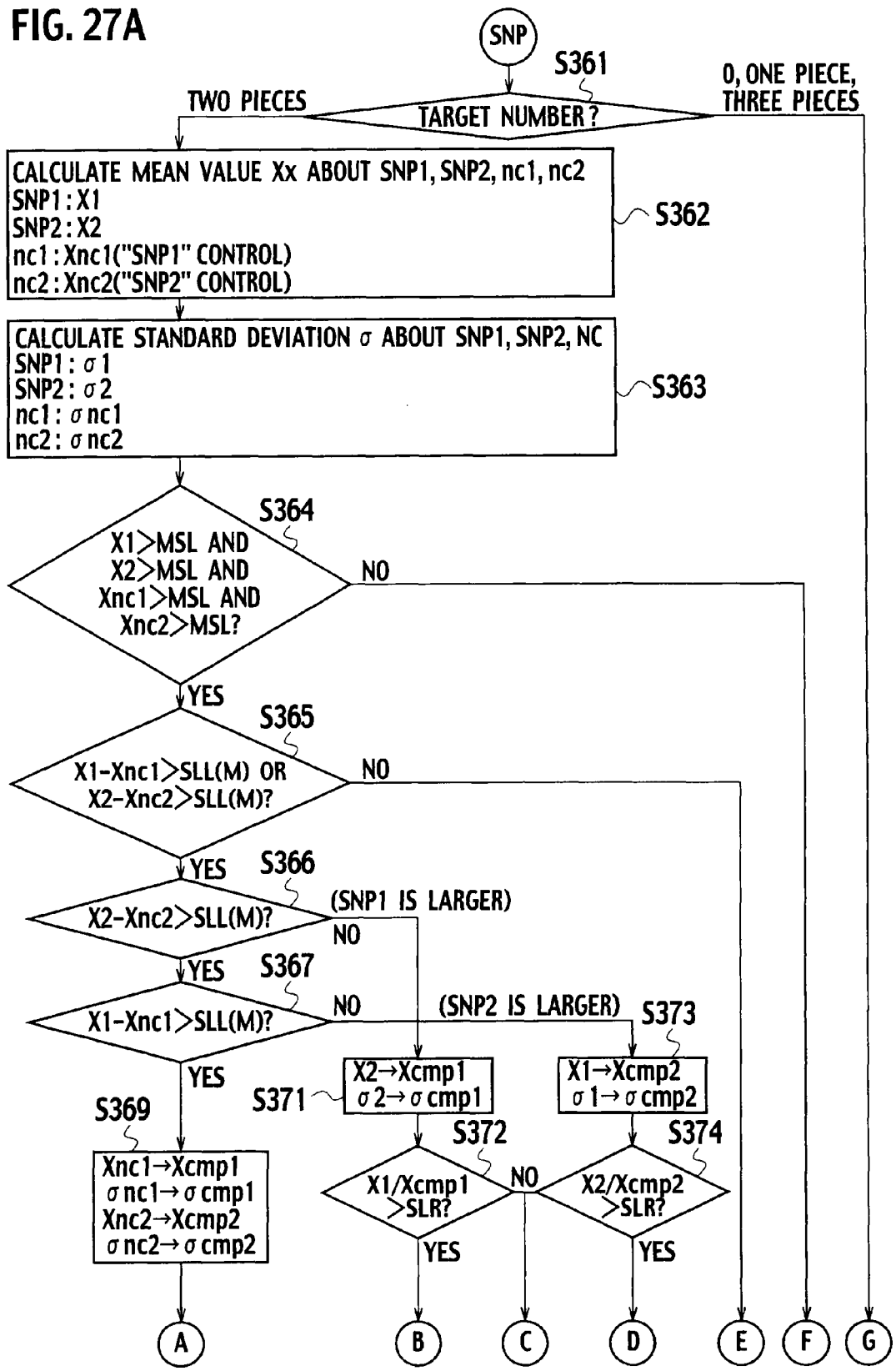
FIG. 27A is a flow chart explaining a second example of the algorithm for determining which of the two kinds of SNP type, the SNP="G" or the SNP="T", is present, or whether the SNP type is the homo-type or the hetero-type, in the nucleotide sequence determination method according to the embodiment of the present invention.

In the step S367 of FIG. 25C, when both the difference in the mean-values $(X_1-X_{nc1})$ at the SNP1 detecting electrodes 551 side is larger than the criterion SLL (M), the determination procedure goes to step S368 to determine if it is homo-type or hetero-type. However, there is a case that the hetero-type can be identified without going through the step S368 as shown in FIG. 27A. Referring to a flowchart shown in FIGS. 27A and 27B, another nucleotide sequence determination method according to a modification of the embodiment of the present invention will be explained. From the step S361 to the step S367, the procedure is similar to the flowchart shown in FIG. 25C, overlapping or redundant description may be omitted in the flowchart shown in FIGS. 27A and 27B.

(a) When the difference in the mean-values $(X_1-X_{nc1})$ is smaller than the criterion SLL (M), the determination procedure goes to step S373, and when the difference in the mean-values $(X_1-X_{nc1})$ at the SNP1 detecting electrodes 551 side is larger than the criterion SLL (M), the determination procedure goes to step S369 (overlapping description of the step S371 and subsequent step after the step S371 will be omitted).

Figure 27B:
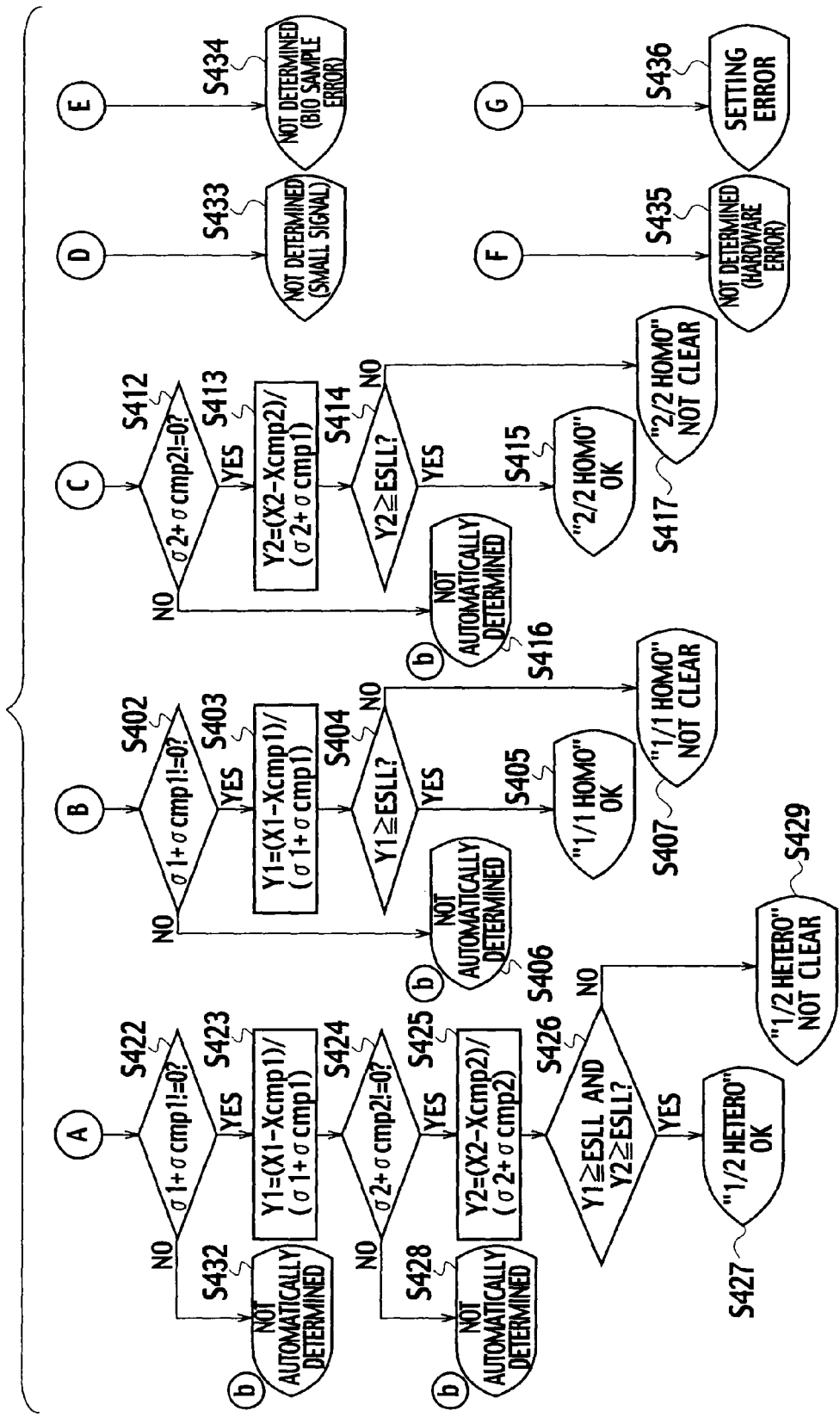
FIG. 27B is a flow chart succeeding to FIG. 27A, explaining the second example of the algorithm for determining which of the two kinds of SNP type, the SNP="G" or the SNP="T", is present, or whether the SNP type is the homo-type or the hetero-type, in the nucleotide sequence determination method according to the embodiment of the present invention.

(b) In step S369, the mean current value $Xnc_1$ calculated from measurement by the control electrodes (NC1) 553 corresponding to the SNP1 detecting electrodes 551 is defined as $X_{cmp1}$, the mean current value $X_{nc2}$ calculated from measurement by the control electrodes (NC2) 553 corresponding to the SNP2 detecting electrodes 552 is defined as $X_{cmp2}$. The mean current value $Xnc_1$ and $X_{nc2}$ are sorted and stored in the mean-value/standard deviation memory 360. Furthermore, the standard deviation $\sigma nc_1$ of the current values, which is calculated from measurement by the control electrodes (NC1) 553 corresponding to the SNP1 detecting electrodes 551, is defined as $\sigma_{cmp1}$, and the standard deviation $\sigma nc_2$ of the current values, which is calculated from measurement by the control electrodes (NC2) 553 corresponding to the SNP2 detecting electrodes 552, is defined as $\sigma_{cmp2}$. The values $\sigma nc_1$ and $\sigma nc_2$ are sorted and stored in the mean-value/standard deviation memory 360, and goes to step S422 as shown in FIG. 27B.

(c) In step S422, the standard deviation $(\sigma_1)$ of the current values measured by the SNP1 detecting electrodes 551 and the standard deviation $(\sigma_{cmp1})$ of the corresponding current values are read out from the mean-value/standard deviation memory 360 to calculate the sum $(\sigma_1+\sigma_{cmp1})$ of the standard deviation ($\sigma$1) and the standard deviation $(\sigma_{cmp1})$. Furthermore, in step S422, the typing module 340 confirms if the sum of the standard deviations $(\sigma_1+\sigma_{cmp1})$ is not "zero." When the sum of the standard deviations $(\sigma_1+\sigma_{cmp1})$ is "zero," the calculation in the next step S423 cannot be conducted. Therefore, in step S432, the determination result is sorted and stored in the classified result storing unit 369, and the display unit 306 displays that it is "not automatically determined." In step S422, if the sum of the standard deviations $(\sigma_1+\sigma_{cmp1})$ is not "zero", the determination procedure goes to step S423.

(d) In step S423, the difference in the mean-values $(X_1-X_{cmp1})$ is read out from the mean-value/standard deviation memory 360 to calculate the ratio $(X_1-X_{cmp1})/(\sigma_1+\sigma_{cmp1})$ of the difference in the mean-values $(X_1-X_{cmp1})$ to the sum of the standard deviations $(\sigma_1+\sigma_{cmp1})$ (see Eq. (9)). The typing module 340 stores the ratio $Y_1$ of the difference in the mean-values to the sum of the standard deviations in the mean-value/standard deviation memory 360, and goes to step S424.

(e) In step S424, the standard deviation $(\sigma_2)$ and the standard deviation $(\sigma_{cmp2})$ are read out from the mean-value/standard deviation portion 360 so as to calculate the sum $(\sigma_2+\sigma_{cmp2})$. In step S424, the typing module 340 confirms if the sum of the standard deviations $(\sigma_2+\sigma_{cmp2})$ is not "zero." When the sum of the standard deviation is $(\sigma_2+\sigma_{cmp2})$ is "zero," the calculation in the next step S425 is not conducted. Therefore, in step S428, the determination result is sorted and stored in the classified result storing unit 369, and the display unit 306 displays that it is "not automatically determined." In step S424, if the sum $(\sigma_2+\sigma_{cmp2})$ of the standard deviation is not "zero," the determination procedure goes to step S425.

(f) In step S425, the difference in the mean-values $(X_2-X_{cmp2})$ is read out from the mean-value/standard deviation memory 360 to calculate the ratio $(X_2-X_{cmp2})/(\sigma_2+\sigma_{cmp2})$ of the difference in the mean-values $(X_2-X_{cmp2})$ to the sum of the standard deviations $(\sigma_2+\sigma_{cmp2})$. The typing module 340 stores the ratio $Y_2$ of the difference in the mean-values and the sum of the standard deviation (see Eq. (10)) in the mean-value/standard deviation memory 360, and goes to step S426.

(g) In step S426, the ratio of the difference in the mean-values to the sum of the standard deviation $Y_1=(X_1-X_{cmp1})/(\sigma_1+\sigma_{cmp1})$ is read out from the mean-value/standard deviation memory 360 and the effective scale factor ESLL is read out from the ESLL memory 363 so that the ratio of the difference in the mean-values to the sum of the standard deviation $Y_1=(X_1-X_{cmp1})/(\sigma_1+\sigma_{cmp1})$ can be compared with the effective scale factor ESLL. Furthermore, in step 426, the ratio of the difference in the mean-values and the sum of the standard deviations $Y_2=(X_2-X_{cmp2})/(\sigma_2+\sigma_{cmp2})$ is read out from the mean-value/standard deviation memory 360 so that the ratio of the difference in the mean-values and the sum of the standard deviation $Y_2=(X_2-X_{cmp2})/(\sigma_2+\sigma_{cmp2})$ can be compared with the effective scale factor ESLL. In step S426, when either $Y_1$ or $Y_2$ is determined to be smaller than the effective scale factor ESLL, the presence of the G/T hetero-type is determined to be "not clear." In step S429, the determination result is sorted and stored in the classified result storing unit 369, and the display unit 306 displays the determination of "G/T hetero not clear". On the other hand, in step S426, when both $Y_1$ and $Y_2$ are simultaneously more than the effective variant coefficient, the G/T hetero-type is determined to be "clearly" present, in step S427, the determination result is sorted and stored in the classified result memory 369, and the display unit 306 displays "G/T hetero OK"

The above-mentioned descriptions of the embodiment are procedures for determining one type among G type, T type, or G/T type. However, it is may be applied to the determination of two types among them or the determination of whether they are hetero of the two types. In addition, as understood by descriptions of above-mentioned embodiment, it is not necessary to acquire the measurement data for four types of A type, G type, C type, and T type groups. Obtaining only two groups for two possible bases of SNP may be sufficient.

Thus, the present invention of course includes various embodiments and modifications and the like which are not detailed above. Therefore, the scope of the present invention will be defined in the following claims.

What is claimed is:

1. A method for determining a nucleotide sequence comprising:
    injecting a solution containing a sample DNA into a chip cartridge provided with a detecting electrode, to which a probe DNA is immobilized;
    introducing an intercalator solution containing an intercalator into the chip cartridge;
    obtaining a current-voltage characteristic curve by measuring current values in the solution due to an electrochemical reaction of the intercalator through the detecting electrode by applying voltages to the detecting electrode;
    obtaining a differential curve of the current-voltage characteristic curve, with respect to voltage;
    defining a peak voltage value as a voltage value at which the differential curve zero-crosses in a voltage range between predetermined lower and upper limit values;
    defining a peak current point as a point on the current-voltage characteristic curve at the peak voltage value;
    defining a peak current value obtained from the current-voltage characteristic curve at the peak current point;
    determining a linear expression approximating the current-voltage characteristic curve between the peak current point and an inflection point, wherein the inflection point is at a value of voltage less than the peak voltage value;
    obtaining an intersection-point voltage value at an intersection-point of the current-voltage characteristic curve and the linear expression, in a voltage range which is less than the voltage of the inflection point;
    defining an offset voltage by subtracting a predetermined offset value from the intersection-point voltage value;
    obtaining a baseline by linearly approximating the current-voltage characteristic curve between the offset voltage and the intersection-point voltage value;
    obtaining a baseline current value, by assigning the peak voltage value for the baseline;
    obtaining a net current value by subtracting from the peak current value, the baseline current value; and
    identifying a nucleotide sequence in the sample DNA, using the net current value.

2. The method of claim 1, wherein before the step of obtaining the baseline by linearly approximating the current-voltage characteristic curve, the method further comprises:
    obtaining a tail line by linearly approximating the current-voltage characteristic curve, in a voltage range between a predetermined lower limit voltage and a predetermined higher limit voltage;
    calculating a slope of the tail line;
    determining whether the current-voltage characteristic curve is a normal profile or an abnormal profile, using the slope of the tail line; and
    excluding the current-voltage characteristic curve which is assigned as the abnormal profile.

3. The method of claim 2, wherein the step of determining whether the current-voltage characteristic curve is the normal profile or abnormal profile comprises:
    determining whether the slope of the tail line lies in a slope range between a predetermined lower limit slope value and a predetermined higher limit slope value; and
    assigning the normal profile to the current-voltage characteristic curve having the slope of the tail line lying in the slope range, and the abnormal profile to the current-voltage characteristic curve having the slope of the tail line lying out of the slope range.

4. The method of claim 2, wherein
    determining whether the current-voltage characteristic curve is a normal profile or an abnormal profile comprises using the chip cartridge with a plurality of the detecting electrodes, wherein for a plurality of net current values, each net current value corresponds to each detecting electrode, and the method further comprises:
    dividing the plurality of the net current values into a plurality of datasets;
    evaluating whether one of the datasets satisfies a certain criterion; and
    excluding an abnormal data that is contained in the evaluated dataset, when the evaluated dataset satisfies the criterion.

5. The method of claim 4, wherein the excluding step comprises:
    selecting a first net current value which is one of the net current values in the evaluated dataset and removing temporarily the first net current value from the dataset to obtain a first detecting dataset;
    evaluating the first detecting dataset whether the first detecting dataset satisfies a first criterion;
    eliminating the first net current value from the evaluated dataset when the first detecting dataset satisfies the first criterion;
    returning the first net current value to the first detecting dataset when the first detecting dataset does not satisfy the first criterion;
    re-selecting a second net current value from the evaluated dataset, when the first detecting dataset does not satisfy the first criterion and removing temporarily the second net current value from the evaluated dataset to obtain a second detecting dataset, the second net current value being different from the first net current value;
    evaluating the second detecting dataset whether the second detecting dataset satisfies a second criterion;
    eliminating the second net current value from the dataset when the second detecting dataset satisfies the second criterion; and
    returning the second net current value to the second detecting dataset when the second detecting dataset does not satisfy the second criterion.

6. The method of claim 5, wherein the first net current value is a minimum value of the net current values of the dataset.

7. The method of claim 5, wherein the second net current value is a maximum value of the net current values of the dataset.

8. The method of claim 5, wherein the step of evaluating whether one of the datasets satisfies a certain criterion comprises:
    calculating a standard deviation and a mean-value of the net current values of the dataset;
    calculating a coefficient of variance value, by dividing the standard deviation by the mean-value; and
    comparing the coefficient of variance value with a predetermined standard coefficient of variance value,
    wherein the dataset does satisfy the criterion, when the coefficient of variance is equal to or larger than the predetermined standard coefficient of variance value.

9. The method of claim 8, wherein the step of evaluating the first detecting dataset comprises:
    calculating a first standard deviation and a first mean-value of the net current values of the first detecting dataset;
    calculating a first coefficient of variance value by dividing the first standard deviation by the first mean-value; and comparing the first coefficient of variance value with the coefficient of variance value multiplied by a predetermined coefficient of variance value correction coefficient, wherein the first detecting dataset satisfies the first criterion, when the first coefficient of variance value is smaller than the coefficient of variance value multiplied by the predetermined coefficient of variance value correction coefficient, and the first detecting dataset does not satisfy the first criterion, when the first coefficient of variance value is equal to or larger than the coefficient of variance value multiplied by the predetermined coefficient of variance value correction coefficient.

10. The method of claim 8, wherein the step of evaluating the second detecting dataset comprises:

calculating a second standard deviation and a second mean-value of the net current values of the second detecting dataset;

calculating a second coefficient of variance value by dividing the second standard deviation by the second mean-value; and comparing the second coefficient of variance value with the coefficient of variance value multiplied by the predetermined coefficient of variance value correction coefficient, wherein the second detecting dataset satisfies a second criterion when the second coefficient of variance value is smaller than the coefficient of variance value multiplied by the predetermined coefficient of variance value correction coefficient.

* * * * *